(12) United States Patent
Bei

(10) Patent No.: US 12,398,181 B2
(45) Date of Patent: Aug. 26, 2025

(54) METHODS AND COMPOSITIONS FOR DELIVERY OF AGENTS ACROSS THE BLOOD-BRAIN BARRIER

(71) Applicant: The Brigham and Women's Hospital, Inc., Boston, MA (US)

(72) Inventor: Fengfeng Bei, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 974 days.

(21) Appl. No.: 17/258,846

(22) PCT Filed: Jul. 11, 2019

(86) PCT No.: PCT/US2019/041386
§ 371 (c)(1),
(2) Date: Jan. 8, 2021

(87) PCT Pub. No.: WO2020/014471
PCT Pub. Date: Jan. 16, 2020

(65) Prior Publication Data
US 2021/0277066 A1    Sep. 9, 2021

Related U.S. Application Data

(60) Provisional application No. 62/696,422, filed on Jul. 11, 2018.

(51) Int. Cl.
| | |
|---|---|
| C07K 14/005 | (2006.01) |
| A61K 31/522 | (2006.01) |
| A61K 35/761 | (2015.01) |
| A61K 38/45 | (2006.01) |
| A61K 48/00 | (2006.01) |
| A61K 49/00 | (2006.01) |
| A61P 35/00 | (2006.01) |
| C07K 14/00 | (2006.01) |
| A61K 38/00 | (2006.01) |

(52) U.S. Cl.
CPC .......... *C07K 14/005* (2013.01); *A61K 31/522* (2013.01); *A61K 35/761* (2013.01); *A61K 38/45* (2013.01); *A61K 48/0008* (2013.01); *A61K 49/0045* (2013.01); *A61K 49/0097* (2013.01); *A61P 35/00* (2018.01); *C07K 14/001* (2013.01); *A61K 38/00* (2013.01); *C07K 2319/00* (2013.01); *C12N 2750/14122* (2013.01); *C12N 2750/14143* (2013.01)

(58) Field of Classification Search
CPC .............. C07K 14/005; C07K 14/001; C07K 2319/00; A61K 31/522; A61K 35/761; A61K 38/45; A61K 48/0008; A61K 49/0045; A61K 49/0097; A61K 38/00; A61P 35/00; C12N 2750/14122; C12N 2750/14143
See application file for complete search history.

(56) References Cited

U.S. PATENT DOCUMENTS

| | | | |
|---|---|---|---|
| 4,522,811 A | 6/1985 | Eppstein et al. | |
| 8,008,449 B2 | 8/2011 | Korman et al. | |
| 8,299,215 B2 | 10/2012 | Davidson et al. | |
| 8,591,900 B2 | 11/2013 | Barrett et al. | |
| 8,927,514 B2 | 1/2015 | Chatterjee et al. | |
| 9,073,994 B2 | 7/2015 | Honjo et al. | |
| 9,102,949 B2 | 8/2015 | Gao et al. | |
| 9,585,971 B2 | 3/2017 | Deverman et al. | |
| 10,370,432 B2 | 8/2019 | Esteves et al. | |
| 10,577,627 B2 | 3/2020 | Kotin et al. | |
| 11,518,787 B2 | 12/2022 | Bei | |
| 11,981,705 B2 | 5/2024 | Bei | |
| 2003/0082143 A1 | 5/2003 | Larocca et al. | |
| 2003/0165499 A1 | 9/2003 | Chu et al. | |
| 2004/0120948 A1 | 6/2004 | Mikayama et al. | |
| 2007/0148163 A1 | 6/2007 | Takahashi et al. | |
| 2011/0271358 A1 | 11/2011 | Freeman et al. | |
| 2011/0294218 A1 | 12/2011 | Chatterjee et al. | |
| 2012/0066783 A1 | 3/2012 | Kay et al. | |
| 2013/0011405 A1 | 1/2013 | Long et al. | |
| 2014/0142160 A1 | 5/2014 | Lee et al. | |
| 2015/0079038 A1 | 3/2015 | Deverman et al. | |
| 2015/0297742 A1 | 10/2015 | Strieker et al. | |
| 2016/0280748 A1 | 9/2016 | Liu et al. | |

(Continued)

FOREIGN PATENT DOCUMENTS

| | | |
|---|---|---|
| CA | 3049237 A1 | 10/2011 |
| CA | 3011939 A1 | 8/2017 |

(Continued)

OTHER PUBLICATIONS

McMahon et al., "Differences in polyadenylation site choice between somatic and male germ cells," BMC Molecular Biology, Dec. 2006, 7:1, 11 pages.

O'Carroll et al., "AAV targeting of glial cell types in the central and peripheral nervous system and relevance to human gene therapy," Frontiers in Molecular Neuroscience, Jan. 2021, 13:618020, 19 pages.

Wang et al., "Astrocytic expression of transgene in the rat brain mediated by baculovirus vectors containing an astrocyte-specific promoter," Gene Therapy, Oct. 2006, 13(20):1447-56.

Zanta-Boussif et al., "Validation of a mutated PRE sequence allowing high and sustained transgene expression while abrogating WHV-X protein synthesis: application to the gene therapy of WAS," Gene Therapy, May 2009, 16(5):605-19.

(Continued)

*Primary Examiner* — Robert S Cabral
(74) *Attorney, Agent, or Firm* — Fish & Richardson P.C.

(57) ABSTRACT

The present invention is based on the development of artificial targeting sequences that enhance permeation of agents into cells and across the blood brain barrier, compositions comprising the sequences, and methods of use thereof. Provided herein is an AAV comprising a capsid protein comprising a targeting sequence and a transgene, preferably a therapeutic or diagnostic transgene. Further, provided herein are methods of delivering a transgene to a cell, the method comprising contacting the cell with an AAV or fusion protein described herein.

11 Claims, 33 Drawing Sheets
Specification includes a Sequence Listing.

(56) References Cited

U.S. PATENT DOCUMENTS

| | | |
|---|---|---|
| 2016/0376325 A1 | 12/2016 | McFadden et al. |
| 2017/0058033 A1 | 3/2017 | Ludwig et al. |
| 2017/0130245 A1 | 5/2017 | Kotin et al. |
| 2017/0166926 A1 | 6/2017 | Deverman et al. |
| 2018/0030429 A1 | 2/2018 | King et al. |
| 2018/0141998 A1 | 5/2018 | Nguyen et al. |
| 2019/0367562 A1 | 12/2019 | Asokan et al. |
| 2020/0325456 A1 | 10/2020 | Li et al. |
| 2021/0163985 A1 | 6/2021 | Sah et al. |
| 2021/0301024 A1 | 9/2021 | Yu et al. |
| 2022/0089650 A1 | 3/2022 | Bei |
| 2023/0048492 A1 | 2/2023 | Bei |
| 2023/0053817 A1 | 2/2023 | Bei et al. |
| 2023/0077490 A1 | 3/2023 | Bei |
| 2024/0285804 A1 | 8/2024 | Bei |

FOREIGN PATENT DOCUMENTS

| | | |
|---|---|---|
| CN | 102170900 A | 8/2011 |
| CN | 105408486 A | 3/2016 |
| CN | 112703198 A | 4/2021 |
| JP | 2016145189 | 8/2016 |
| JP | 2018510215 A | 4/2018 |
| WO | WO 2002/088186 | 11/2002 |
| WO | WO 2005/000220 | 1/2005 |
| WO | WO 2007/124299 | 11/2007 |
| WO | WO 2011/123489 | 10/2011 |
| WO | WO 2012/087983 | 6/2012 |
| WO | WO 2012/111762 | 8/2012 |
| WO | WO 2012/145601 | 10/2012 |
| WO | WO 2012/149356 | 11/2012 |
| WO | WO 2013/079174 | 6/2013 |
| WO | WO 2014/060109 | 4/2014 |
| WO | WO 2014052789 | 4/2014 |
| WO | WO 2014/070934 | 5/2014 |
| WO | WO 2014/086835 | 6/2014 |
| WO | WO 2014/195852 | 12/2014 |
| WO | WO 2015038958 | 3/2015 |
| WO | WO 2015/060722 A1 | 4/2015 |
| WO | WO 2015/127094 | 8/2015 |
| WO | WO 2015/138628 | 9/2015 |
| WO | WO 2015191508 | 12/2015 |
| WO | WO 2016/007235 | 1/2016 |
| WO | WO 2016/061142 | 4/2016 |
| WO | WO 2016054554 | 4/2016 |
| WO | WO 2016/138525 | 9/2016 |
| WO | WO 2017/008336 | 1/2017 |
| WO | WO 2017/083368 | 5/2017 |
| WO | WO 2017/100671 | 6/2017 |
| WO | WO 2017/118321 | 7/2017 |
| WO | WO 2017/136536 | 8/2017 |
| WO | WO 2019/012176 | 1/2019 |
| WO | WO 2019/028306 | 2/2019 |
| WO | WO 2019126356 | 6/2019 |
| WO | WO 2019/222329 | 11/2019 |
| WO | WO 2019/222441 | 11/2019 |
| WO | WO 2020/006274 | 1/2020 |
| WO | WO 2020/014471 | 1/2020 |
| WO | WO 2020/028751 | 2/2020 |
| WO | WO 2020/068990 | 4/2020 |
| WO | WO 2020/072683 | 4/2020 |
| WO | WO 2020/077165 | 4/2020 |
| WO | WO 2020/160337 | 8/2020 |
| WO | WO 2020/210655 | 10/2020 |
| WO | WO 2020/223279 | 11/2020 |
| WO | WO 2021/025995 | 2/2021 |

OTHER PUBLICATIONS

EP Extended Search Report in European Appln. No. 19833958.2, dated Mar. 21, 2022, 9 pages.
JP Office Action in Japanese Appln. No. 2021-500538, mailed on Feb. 6, 2024, 19 pages (with English translation).
PCT International Search Report and Written Opinion in International Appln. No. PCT/US2021/012746, dated Jul. 1, 2021, 17 pages.
Wang et al., "A rationally engineered capsid variant of AAV9 for systemic CNS-directed and peripheral tissue-detargeted gene delivery in neonates," Molecular Therapy—Methods & Clinical Development, Jun. 15, 2018, 9:234-46.
Bryan et al., "Implications of protein fold switching," Current Opinion in Structural Biology, Feb. 2013, 2(23):314-6.
Bulcha et al., "Viral vector platforms within the gene therapy landscape," Signal Transduction and Targeted Therapy, Feb. 2021, 6(1):53.
Cruz et al., "Protein function prediction," Functional Genomics: Methods and Protocols, Sep. 2017:55-75.
Kotterman et al., "Engineering adeno-associated viruses for clinical gene therapy," Nature Reviews Genetics, Jul. 2014, 15(7):445-51.
Lenzi et al., "Oversight and Review of Clinical Gene Transfer Protocols: Assessing the Role of the Recombinant DNA Advisory Committee," Committee on the Independent Review and Assessment of the Activities of the NIH Recombinant DNA Advisory Committee, Mar. 2014.
Maqbool et al., "The substrate-binding protein in bacterial ABC transporters: dissecting roles in the evolution of substrate specificity," Biochemical Society Transactions, Oct. 2015, 43(5):1011-7.
Shim et al., "Nonviral delivery systems for cancer gene therapy: strategies and challenges," Current Gene Therapy, Feb. 2018, 18(1):3-20.
Batista et al., "Ly6a differential expression in blood-brain barrier is responsible for strain specific central nervous system transduction profile of AAV-PHP. B," Human Gene Therapy, Jan. 1, 2020, 31(1-2):90-102.
Deverman et al., "Gene therapy for neurological disorders: progress and prospects," Nature Reviews Drug Discovery, Sep. 2018, 17(9):641-59.
Engeland et al., "CTLA-4 and PD-L1 checkpoint blockade enhances oncolytic measles virus therapy," Molecular Therapy, Nov. 1, 2014, 22(11):1949-59.
Gomez et al., "Bax-inhibiting peptides derived from Ku70 and cell-penetrating pentapeptides," Biochemical Society Transactions, Aug. 1, 2007, 35(4):797-801.
Gomez et al., "Cell-penetrating penta-peptides (CPP5s): measurement of cell entry and protein-transduction activity," Pharmaceuticals, Dec. 2010, 3(12):3594-613.
Gomez, "Development of Cell Penetrating Bax Inhibiting Peptides (BIP), Doctoral dissertation," Case Western Reserve University, Jan. 2010, 189 pages.
Hordeaux et al., "The GPI-linked protein LY6A drives AAV-PHP. B transport across the blood-brain barrier." Molecular Therapy, May 8, 2019, 27(5):912-21.
Hordeaux et al., "The neurotropic properties of AAV-PHP. B are limited to C57BL/6J mice," Molecular Therapy, Mar. 7, 2018, 26(3):664-8.
Huang et al., "Delivering genes across the blood-brain barrier: LY6A, a novel cellular receptor for AAV-PHP. B capsids," PloS one, Nov. 14, 2019, 14(11):e0225206.
Hudry et al., "Therapeutic AAV gene transfer to the nervous system: a clinical reality," Neuron, Mar. 6, 2019, 101(5):839-62.
Matsuzaki et al., "Intravenous administration of the adeno-associated virus-PHP. B capsid fails to upregulate transduction efficiency in the marmoset brain," Neuroscience Letters, Feb. 5, 2018, 665:182-8.
Milletti, "Cell-penetrating peptides: classes, origin, and current landscape," Drug Discovery Today, Aug. 1, 2012, 17(15-16):850-60.
PCT International Preliminary Report on Patentability in International Appln. No. PCT/US2019/041386, dated Jan. 12, 2021, 7 pages.
PCT International Search Report and Written Opinion in International Appln. No. PCT/US2019/041386, dated Oct. 17, 2019, 15 pages.
Reul et al., "Tumor-specific delivery of immune checkpoint inhibitors by engineered AAV vectors," Frontiers in Oncology, Feb. 14, 2019, 9:52.

(56) References Cited

OTHER PUBLICATIONS

Wolfe et al., "Pentelute BL. Machine learning to predict cell-penetrating peptides for antisense delivery," ACS Central Science, Apr. 5, 2018, 4(4):512-20.
Alexandrescu et al., "Immunotherapy for melanoma: current status and perspectives," Journal of Immunotherapy (Hagerstown, Md.: 1997), Jul. 2010, 33(6):570.
Avan et al., "Peptidomimetics via modifications of amino acids and peptide bonds," Chemical Society Reviews, Mar. 2014, 43(10):3575, 1 page (abstract only).
Barash et al., "Human secretory signal peptide description by hidden Markov model and generation of a strong artificial signal peptide for secreted protein expression," Biochemical and Biophysical Research Communications, Jun. 21, 2002, 294(4):835, 1 page (abstract only).
Brennan et al., "The somatic genomic landscape of glioblastoma," Cell, Oct. 10, 2013, 155(2):462-77.
Chen et al., "Molecular signatures of disease brain endothelia provide new sites for CNS-directed enzyme therapy," Nature Medicine, Oct. 2009, 15(10):1215-8.
Cho et al., "Blood-brain-barrier spheroids as an in vitro screening platform for brain-penetrating agents," Nature Communications, Jun. 6, 2017, 8(1):1-4.
Eggermont et al., "Anti-CTLA-4 antibody adjuvant therapy in melanoma," Seminars in Oncology, Oct. 1, 2010, 37(5):455-59.
Farhadi et al., "Computer-aided design of amino acid-based therapeutics: A review," Drug Design, Development and Therapy, 2018, 12:1239.
Flotte et al., "Expression of the cystic fibrosis transmembrane conductance regulator from a novel adeno-associated virus promoter," Journal of Biological Chemistry, Feb. 15, 1993, 268(5):3781-90.
Ganesan et al., "Systemic therapy for melanoma," National Medical Journal of India, Jan. 1, 2010, 23(1):21.
Geisler et al., "MicroRNA-regulated viral vectors for gene therapy," World Journal of Experimental Medicine, May 20, 2016, 6(2):37.
Golovina et al., "T cells: overcoming suppression of T-cell immunity," The Cancer Journal, Jul. 1, 2010, 16(4):342, 2 pages (abstract only).
Gray et al., "Vector design and considerations for CNS applications," Gene Vector Design and Application to Treat Nervous System Disorders, Jan. 2011, 1-9.
Hermonat et al., "Use of adeno-associated virus as a mammalian DNA cloning vector: transduction of neomycin resistance into mammalian tissue culture cells," Proceedings of the National Academy of Sciences, Oct. 1984, 81(20):6466-70.
Herrlinger et al., "Lomustine-temozolomide combination therapy versus standard temozolomide therapy in patients with newly diagnosed glioblastoma with methylated MGMT promoter (CeTeG/NOA-09): a randomised, open-label, phase 3 trial," The Lancet, Feb. 16, 2019, 393(10172):678-88.
Jain et al., "Angiogenesis in brain tumours," Nature Reviews Neuroscience, Aug. 2007, 8(8):610-22.
Klinke, "A multiscale systems perspective on cancer, immunotherapy, and Interleukin-12," Molecular Cancer, Dec. 2010, 9(1):1-8.
Kober et al., "Optimized signal peptides for the development of high expressing CHO cell lines," Biotechnology and Bioengineering, Apr. 2013, 110(4):1164-73.
Krüger et al., "Immune based therapies in cancer," Histology and Histopathology, Jun. 2007, 22(6): 687-96.
Li et al., "A mini-review for cancer immunotherapy: molecular understanding of PD-1/PD-L1 pathway & translational blockade of immune checkpoints," International Journal of Molecular Sciences, Jul. 18, 2016, 17(7):1151, 22 pages.
Lim et al., "Current state of immunotherapy for glioblastoma," Nature Reviews Clinical Oncology, Jul. 2018, 15(7):422, 1 page (abstract only).
Mayo et al., "Design of a partial peptide mimetic of anginex with antiangiogenic and anticancer activity," Journal of Biological Chemistry, Nov. 14, 2003, 278(46):45746-52.

Moschella et al., "Combination strategies for enhancing the efficacy of immunotherapy in cancer patients," Annals of the New York Academy of Sciences, May 2010, 1194(1):169, 1 page (abstract only).
Nakashima et al., "Modeling tumor immunity of mouse glioblastoma by exhausted CD8+ T cells," Scientific Reports, Jan. 2018, 8(1):1-0.
NCBI Accession No. NP_001241.1, "tumor necrosis factor receptor superfamily member 5 isoform 1 precursor [Homo sapiens]," dated Oct. 11, 2019, 4 pages.
NCBI Accession No. NP_001254635.1, "programmed cell death 1 ligand 1 isoform b precursor [Homo sapiens]," dated Dec. 8, 2019, 3 pages.
NCBI Accession No. NP_001289682.1, "tumor necrosis factor receptor superfamily member 5 isoform 3 precursor [Homo sapiens]," Oct. 11, 2019, 3 pages.
NCBI Accession No. NP_001300958.1, "programmed cell death 1 ligand 1 isoform c [Homo sapiens]," dated Dec. 8, 2019, 3 pages.
NCBI Accession No. NP_001309350.1, "tumor necrosis factor receptor superfamily member 5 isoform 4 precursor [Homo sapiens]," dated Oct. 10, 2019, 4 pages.
NCBI Accession No. NP_001309351.1, "tumor necrosis factor receptor superfamily member 5 isoform 5 precursor [Homo sapiens]," dated Oct. 10, 2019, 3 pages.
NCBI Accession No. NP_005009.2, "programmed cell death protein 1 precursor [Homo sapiens]," dated Dec. 4, 2019, 4 pages.
NCBI Accession No. NP_054862.1, "programmed cell death 1 ligand 1 isoform a precursor [Homo sapiens]," dated Dec. 8, 2019, 4 pages.
NCBI Accession No. NP_690593.1, "tumor necrosis factor receptor superfamily member 5 isoform 2 precursor [Homo sapiens]," dated Oct. 10, 2019, 3 pages.
Ostrom et al., CBTRUS statistical report: primary brain and other central nervous system tumors diagnosed in the United States in 2010-2014, Neuro-oncology, Nov. 6, 2017, 19(suppl_5):v1-88.
Pathak et al., "Review on peptidomimetics: a drug designing tool," American Journal of Pharmaceutical Research, Dec. 2015, 5(12).
PCT International Preliminary Report on Patentability in International Appln. No. PCT/US2021/012746, dated Jul. 12, 2022, 10 pages.
PCT International Search Report and Written Opinion in International Appln. No. PCT/US2022/073051, dated Dec. 28, 2022, 14 pages.
Perry et al., "Histologic classification of gliomas," Handbook of Clinical Neurology, Jan. 1, 2016, 134:71, 1 pages (abstract only).
Pulicherla et al., "Engineering liver-detargeted AAV9 vectors for cardiac and musculoskeletal gene transfer," Molecular Therapy, Jun. 1, 2011, 19(6):1070-8.
Qvit et al., "Peptidomimetic therapeutics: scientific approaches and opportunities," Drug Discovery Today, Feb. 2017, 22(2):454-62.
Stupp et al., "Radiotherapy plus concomitant and adjuvant temozolomide for glioblastoma," New England Journal of Medicine, Mar. 10, 2005, 352(10):987-96.
Sun et al., "Enhanced efficacy of an AAV vector encoding chimeric, highly secreted acid α-glucosidase in glycogen storage disease type II," Molecular Therapy, Dec. 1, 2006, 14(6):822-30.
Tratschin et al., "A human parvovirus, adeno-associated virus, as a eucaryotic vector: transient expression and encapsidation of the procaryotic gene for chloramphenicol acetyltransferase," Molecular and Cellular Biology, Oct. 1984, 4(10):2072-81.
Tratschin et al., "Adeno-associated virus vector for high-frequency integration, expression, and rescue of genes in mammalian cells," Molecular and Cellular Biology, Nov. 1985, 5(11):3251-60.
Tratschin et al., "Genetic analysis of adeno-associated virus: properties of deletion mutants constructed in vitro and evidence for an adeno-associated virus replication function," Journal of Virology, Sep. 1984, 51(3):611-9.
Tsuchiya et al., "Gene design of signal sequence for effective secretion of protein," Nucleic Acids Symposium Series, Sep. 2003, 3(1):261-62.
Von Heijne, "Signal sequences: the limits of variation," Journal of Molecular Biology, Jul. 1985, 184(1):99, 1 page (abstract only).
Wen et al., "Malignant gliomas in adults," New England Journal of Medicine, Jul. 31, 2008, 359(5):492-507.

(56) References Cited

OTHER PUBLICATIONS

Wondisford et al., "Cloning of the human thyrotropin β-subunit gene and transient expression of biologically active human thyrotropin after gene transfection," Molecular Endocrinology, Januar 1988, 2(1):32-9.
Xu et al., "A combination of mutations enhances the neurotropism of AAV-2," Virology, Oct. 25, 2005, 341(2):203-14.
Deverman et al., "Cre-dependent selection yields AAV variants for widespread gene transfer to the adult brain," Nature Biotechnology, Feb. 2016, 34(2):204-9.
CN Office Action in Chinese Appln. No. 201980059342.1, mailed on Jul. 18, 2024, 9 pages (with English translation).
EP Office Action in European Appln. No. 19833958.2, mailed on Jun. 3, 2024, 4 pages.
Ma et al., "Biodistribution of adeno-associated virus 9-mediated gene expression with a CAR promoter in mice," Chinese Journal of Virology, May 2019, 35(3), 8 pages (with English Abstract).
Chao et al., "Gene therapy for human lung adenocarcinoma using a suicide gene driven by a lung-specific promoter delivered by JC virus-like particles," PLoS One, Jun. 2016, 11(6):e0157865, 12 pages.
Doerfler et al., "Copackaged AAV9 vectors promote simultaneous immune tolerance and phenotypic correction of Pompe disease," Human Gene Therapy, Jan. 2016, 27(1):43-59.
Gam et al., "A mixed antagonistic/synergistic miRNA repression model enables accurate predictions of multi-input miRNA sensor activity," Nature Communications, Jun. 2018, 9(1):2430, 12 pages.
Nyon et al., "Engineering a stable CHO cell line for the expression of a MERS-coronavirus vaccine antigen," Vaccine, Mar. 2018, 36(14):1853-62.
snapgene.com, "GAM hsa-mi R-1-5p target sequence," Jun. 3, 22, 2018, 1 page.
snapgene.com, "GAM lsb hsa miR-200c-5p target sequence," Jun. 22, 2018, 1 page.
Trepel et al., "Treatment of multifocal breast cancer by systemic delivery of dual-targeted adeno-associated viral vectors," Gene Therapy, Oct. 2015, 22(10):840-7.
Wu et al., "AAV2/5-mediated NGF gene delivery protects septal cholinergic neurons following axotomy," Brain Research, Nov. 2005, 1061(2):107-13.
Xie et al., "MicroRNA-regulated, systemically delivered rAAV9: a step closer to CNS-restricted transgene expression," Molecular Therapy, Mar. 2011, 19(3):526-35.
CN Office Action in Chinese Appln. No. 201980059342.1, mailed on Oct. 10, 2023, 22 pages (with English translation).
Gomez et al., "Cell-penetrating penta-peptides and BAX-inhibiting peptides: Protocol for their application," Cell-Penetrating Peptides: Methods and Protocols, Jan. 2011, 683:465, 6 pages.
Zhang et al., "Blood-brain barrier shuttle peptides enhance AAV transduction in the brain after systemic administration," Biomaterials, Sep. 2018, 176:71, 27 pages.
JP Japanese Office Action in Japanese Appln. No. 2021-500538, dated Jun. 6, 2023, 11 pages (with English translation).

```
                         V  IV III    II      I
                         ╷──╷──╷──────╷───────╷
                         575                582
Human Ku70      ··· K F T V P M L K ···
(609 aa)
                         573                580
Mouse Ku70      ··· K L T V P T L K ···
(608 aa)
                         573                580
Rat Ku70        ··· K F T V P A L R ···
(608 aa)
```

| AAV | Insert |
|---|---|
| AAV-CPP.11 | V P A L R |
| AAV-CPP.12 | V S A L K |
| AAV-CPP.15 | T V P A L R |
| AAV-CPP.16 | T V S A L K |
| AAV-CPP.17 | F T V S A L K |
| AAV-CPP.18 | L T V S A L K |
| AAV-CPP.19 | K F T V S A L K |
| AAV-CPP.20 | T F V S A L K |
| AAV-CPP.21 | T V S A L F K |

FIG. 3A

C57BL/6J, $1 \times 10^{12}$ vg

BALB/cJ, $1 \times 10^{12}$ vg

AAV.CPP.16

Cortex
NeuN        RFP

Midbrain
NeuN        RFP

Hippocampus
NeuN        RFP

AAV.CPP. 21
Cortex
NeuN | RFP
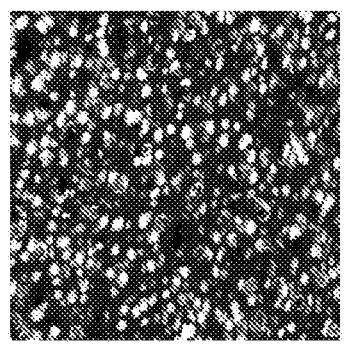 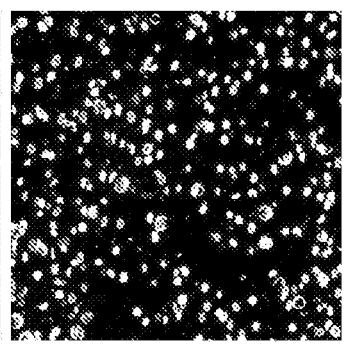
Midbrain
NeuN | RFP
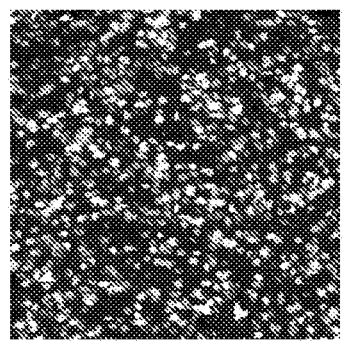 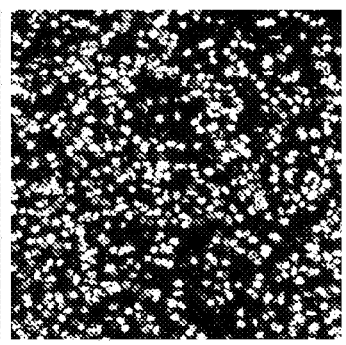
Hippocampus
NeuN | RFP
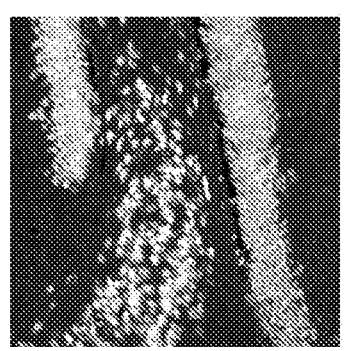 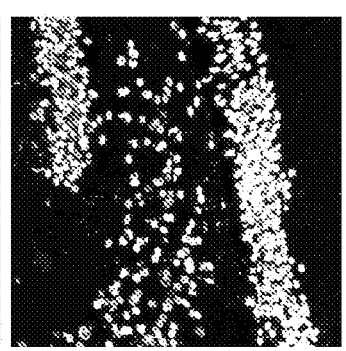
*FIG. 8A, continued*

Primary visual cortex

AAV9

AAV.CPP.16

AAV.CPP.21

Cerebellum

AAV9

AAV.CPP.16

AAV.CPP.21

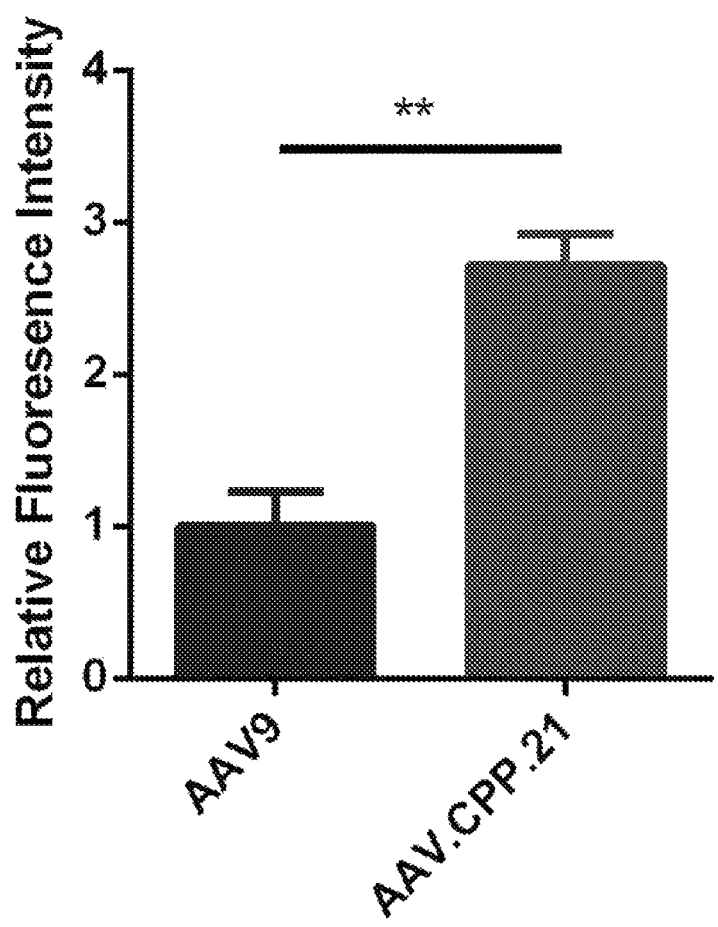
FIG. 13, continued

SEQUENCE LISTING

```
<160> NUMBER OF SEQ ID NOS: 104

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Pro Ala Leu Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ser Ala Leu Lys
1               5

<210> SEQ ID NO 3
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 3

Thr Val Pro Ala Leu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Val Ser Ala Leu Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Thr Val Ser Ala Leu Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Thr Val Ser Ala Leu Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Val Ser Ala Leu Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Val Ser Ala Leu Phe Lys
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Val Pro Ala Leu Phe Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Val Pro Met Leu Phe Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Val Pro Thr Leu Phe Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Val Pro Met Leu Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Val Pro Thr Leu Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 14

Val Pro Met Leu Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Pro Thr Leu Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Pro Met Leu Lys Glu
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Pro Thr Leu Lys Asp
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Pro Ala Leu Arg Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ser Ala Leu Lys Glu
1               5

<210> SEQ ID NO 20
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ser Ala Leu Lys Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ala Val Ser Leu Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Ala Leu Val Ser Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Val Leu Ser Ala Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Leu Val Ser Ala Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Thr Met Val Pro Leu Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Met Leu Val Pro Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Val Leu Pro Met Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Leu Val Pro Met Lys
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Thr Val Pro Leu Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Thr Leu Val Pro Lys
1               5

<210> SEQ ID NO 31
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Val Leu Pro Thr Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Leu Val Pro Thr Lys
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ala Val Pro Leu Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Ala Leu Val Pro Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Val Leu Pro Ala Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 36

Thr Leu Val Pro Ala Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Val Ser Leu Lys Glu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ala Leu Val Ser Lys Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Val Leu Ser Ala Lys Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Leu Val Ser Ala Lys Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Met Val Pro Leu Lys Glu
1               5

<210> SEQ ID NO 42
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Met Leu Val Pro Lys Glu
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Val Leu Pro Met Lys Glu
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Leu Val Pro Met Lys Glu
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Thr Val Pro Leu Lys Asp
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Thr Leu Val Pro Lys Asp
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Thr Val Leu Pro Thr Lys Asp
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Leu Val Pro Thr Lys Asp
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Ala Val Pro Leu Arg Asp
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ala Leu Val Pro Arg Asp
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Val Leu Pro Ala Arg Asp
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Leu Val Pro Ala Arg Asp
1               5

<210> SEQ ID NO 53
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ala Val Ser Leu Phe Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Ala Leu Val Ser Phe Lys
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Val Leu Ser Ala Phe Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Leu Val Ser Ala Phe Lys
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Met Val Pro Leu Phe Lys
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Thr Met Leu Val Pro Phe Lys
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Val Leu Pro Met Phe Lys
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Leu Val Pro Met Phe Lys
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Thr Val Pro Leu Phe Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Thr Leu Val Pro Phe Lys
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Val Leu Pro Thr Phe Lys
1               5

<210> SEQ ID NO 64
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Leu Val Pro Thr Phe Lys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Ala Val Pro Leu Phe Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ala Leu Val Pro Phe Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Val Leu Pro Ala Phe Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Leu Val Pro Ala Phe Arg
1               5

<210> SEQ ID NO 69
<211> LENGTH: 8
<212> TYPE: PRT
<213> ORGANISM: Homo sapiens

<400> SEQUENCE: 69

Lys Phe Thr Val Pro Met Leu Lys
1               5
```

```
<210> SEQ ID NO 70
<211> LENGTH: 8
<212> TYPE: PRT
<213> ORGANISM: Mus sp.

<400> SEQUENCE: 70

Lys Leu Thr Val Pro Thr Leu Lys
1               5

<210> SEQ ID NO 71
<211> LENGTH: 8
<212> TYPE: PRT
<213> ORGANISM: Rattus sp.

<400> SEQUENCE: 71

Lys Phe Thr Val Pro Ala Leu Arg
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Phe Thr Val Ser Ala Leu Lys
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<223> OTHER INFORMATION: See specification as filed for detailed
      description of substitutions and preferred embodiments

<400> SEQUENCE: 73

Xaa Xaa Xaa Xaa Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: V, A, L, I, G, P, S, T, or M
<220> FEATURE:
<221> NAME/KEY: MOD_RES
<222> LOCATION: (6)..(6)
<223> OTHER INFORMATION: K, R, H, D, or E
<220> FEATURE:
<223> OTHER INFORMATION: See specification as filed for detailed
      description of substitutions and preferred embodiments
```

```
<400> SEQUENCE: 74

Thr Xaa Xaa Xaa Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<221> NAME/KEY: MOD_RES
<222> LOCATION: (6)..(6)
<223> OTHER INFORMATION: E or D
<220> FEATURE:
<223> OTHER INFORMATION: See specification as filed for detailed
      description of substitutions and preferred embodiments

<400> SEQUENCE: 75

Xaa Xaa Xaa Xaa Xaa Xaa
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, L, W, or Y
<220> FEATURE:
<221> NAME/KEY: MOD_RES
<222> LOCATION: (3)..(6)
<223> OTHER INFORMATION: V, A, L, I, G, P, S, T, or M
<220> FEATURE:
<221> NAME/KEY: MOD_RES
<222> LOCATION: (7)..(7)
<223> OTHER INFORMATION: K, R, H, D, or E
<220> FEATURE:
<223> OTHER INFORMATION: See specification as filed for detailed
      description of substitutions and preferred embodiments

<400> SEQUENCE: 76

Xaa Thr Xaa Xaa Xaa Xaa Xaa
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: V, A, L, I, G, P, S, T, or M
<220> FEATURE:
<221> NAME/KEY: MOD_RES
<222> LOCATION: (6)..(6)
```

```
<223> OTHER INFORMATION: K, R, H, D, or E
<220> FEATURE:
<221> NAME/KEY: MOD_RES
<222> LOCATION: (7)..(7)
<223> OTHER INFORMATION: E or D
<220> FEATURE:
<223> OTHER INFORMATION: See specification as filed for detailed
      description of substitutions and preferred embodiments

<400> SEQUENCE: 77

Thr Xaa Xaa Xaa Xaa Xaa Xaa
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<221> NAME/KEY: MOD_RES
<222> LOCATION: (6)..(6)
<223> OTHER INFORMATION: E or D
<220> FEATURE:
<221> NAME/KEY: MOD_RES
<222> LOCATION: (7)..(7)
<223> OTHER INFORMATION: A or I
<220> FEATURE:
<223> OTHER INFORMATION: See specification as filed for detailed
      description of substitutions and preferred embodiments

<400> SEQUENCE: 78

Xaa Xaa Xaa Xaa Xaa Xaa Xaa
1               5

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: S or P
<220> FEATURE:
<221> NAME/KEY: MOD_RES
<222> LOCATION: (3)..(3)
<223> OTHER INFORMATION: A, M, or T
<220> FEATURE:
<223> OTHER INFORMATION: See specification as filed for detailed
      description of substitutions and preferred embodiments

<400> SEQUENCE: 79

Val Xaa Xaa Leu
1

<210> SEQ ID NO 80
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T
<220> FEATURE:
<223> OTHER INFORMATION: See specification as filed for detailed
      description of substitutions and preferred embodiments

<400> SEQUENCE: 80

Thr Val Xaa Xaa Leu
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T
<220> FEATURE:
<223> OTHER INFORMATION: See specification as filed for detailed
      description of substitutions and preferred embodiments

<400> SEQUENCE: 81

Thr Val Xaa Xaa Leu Lys
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T
<220> FEATURE:
<223> OTHER INFORMATION: See specification as filed for detailed
      description of substitutions and preferred embodiments

<400> SEQUENCE: 82

Thr Val Xaa Xaa Leu Phe Lys
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 83

Lys Leu Ala Ser Val Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Phe Leu Ala Ser Val Thr
1               5

<210> SEQ ID NO 85
<211> LENGTH: 736
<212> TYPE: PRT
<213> ORGANISM: Adeno-associated virus 9

<400> SEQUENCE: 85

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

```
Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685
```

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 86
<211> LENGTH: 609
<212> TYPE: PRT
<213> ORGANISM: Homo sapiens

<400> SEQUENCE: 86

Met Ser Gly Trp Glu Ser Tyr Tyr Lys Thr Glu Gly Asp Glu Ala
1               5                   10                  15

Glu Glu Glu Gln Glu Asn Leu Glu Ala Ser Gly Asp Tyr Lys Tyr
                20                  25                  30

Ser Gly Arg Asp Ser Leu Ile Phe Leu Val Asp Ala Ser Lys Ala Met
            35                  40                  45

Phe Glu Ser Gln Ser Glu Asp Glu Leu Thr Pro Phe Asp Met Ser Ile
50                  55                  60

Gln Cys Ile Gln Ser Val Tyr Ile Ser Lys Ile Ile Ser Ser Asp Arg
65                  70                  75                  80

Asp Leu Leu Ala Val Val Phe Tyr Gly Thr Lys Asp Lys Asn Ser
                85                  90                  95

Val Asn Phe Lys Asn Ile Tyr Val Leu Gln Glu Leu Asp Asn Pro Gly
                100                 105                 110

Ala Lys Arg Ile Leu Glu Leu Asp Gln Phe Lys Gly Gln Gln Gly Gln
            115                 120                 125

Lys Arg Phe Gln Asp Met Met Gly His Gly Ser Asp Tyr Ser Leu Ser
130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
            180                 185                 190

Leu Arg Asp Thr Gly Ile Phe Leu Asp Leu Met His Leu Lys Lys Pro
195                 200                 205

Gly Gly Phe Asp Ile Ser Leu Phe Tyr Arg Asp Ile Ile Ser Ile Ala
210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Ile Lys Leu
            275                 280                 285

Tyr Arg Glu Thr Asn Glu Pro Val Lys Thr Lys Thr Arg Thr Phe Asn
290                 295                 300

Thr Ser Thr Gly Gly Leu Leu Leu Pro Ser Asp Thr Lys Arg Ser Gln
305                 310                 315                 320

```
Ile Tyr Gly Ser Arg Gln Ile Ile Leu Glu Lys Glu Thr Glu Glu
                325                 330                 335

Leu Lys Arg Phe Asp Asp Pro Gly Leu Met Leu Met Gly Phe Lys Pro
            340                 345                 350

Leu Val Leu Leu Lys Lys His His Tyr Leu Arg Pro Ser Leu Phe Val
            355                 360                 365

Tyr Pro Glu Glu Ser Leu Val Ile Gly Ser Ser Thr Leu Phe Ser Ala
370                 375                 380

Leu Leu Ile Lys Cys Leu Glu Lys Glu Val Ala Ala Leu Cys Arg Tyr
385                 390                 395                 400

Thr Pro Arg Arg Asn Ile Pro Pro Tyr Phe Val Ala Leu Val Pro Gln
            405                 410                 415

Glu Glu Glu Leu Asp Asp Gln Lys Ile Gln Val Thr Pro Pro Gly Phe
            420                 425                 430

Gln Leu Val Phe Leu Pro Phe Ala Asp Asp Lys Arg Lys Met Pro Phe
            435                 440                 445

Thr Glu Lys Ile Met Ala Thr Pro Glu Gln Val Gly Lys Met Lys Ala
            450                 455                 460

Ile Val Glu Lys Leu Arg Phe Thr Tyr Arg Ser Asp Ser Phe Glu Asn
465                 470                 475                 480

Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
            500                 505                 510

Ala Met Asn Lys Arg Leu Gly Ser Leu Val Asp Glu Phe Lys Glu Leu
            515                 520                 525

Val Tyr Pro Pro Asp Tyr Asn Pro Glu Gly Lys Val Thr Lys Arg Lys
            530                 535                 540

His Asp Asn Glu Gly Ser Gly Ser Lys Arg Pro Lys Val Glu Tyr Ser
545                 550                 555                 560

Glu Glu Glu Leu Lys Thr His Ile Ser Lys Gly Thr Leu Gly Lys Phe
                565                 570                 575

Thr Val Pro Met Leu Lys Glu Ala Cys Arg Ala Tyr Gly Leu Lys Ser
            580                 585                 590

Gly Leu Lys Lys Gln Glu Leu Leu Glu Ala Leu Thr Lys His Phe Gln
            595                 600                 605

Asp

<210> SEQ ID NO 87
<211> LENGTH: 608
<212> TYPE: PRT
<213> ORGANISM: Mus sp.

<400> SEQUENCE: 87

Met Ser Glu Trp Glu Ser Tyr Tyr Lys Thr Glu Gly Glu Glu Glu
1               5                   10                  15

Glu Glu Glu Glu Ser Pro Asp Thr Gly Gly Glu Tyr Lys Tyr Ser Gly
                20                  25                  30

Arg Asp Ser Leu Ile Phe Leu Val Asp Ala Ser Arg Ala Met Phe Glu
            35                  40                  45

Ser Gln Gly Glu Asp Glu Leu Thr Pro Phe Asp Met Ser Ile Gln Cys
        50                  55                  60

Ile Gln Ser Val Tyr Thr Ser Lys Ile Ile Ser Ser Asp Arg Asp Leu
65                  70                  75                  80
```

```
Leu Ala Val Val Phe Tyr Gly Thr Glu Lys Asp Lys Asn Ser Val Asn
                 85                  90                  95

Phe Lys Asn Ile Tyr Val Leu Gln Asp Leu Asp Asn Pro Gly Ala Lys
            100                 105                 110

Arg Val Leu Glu Leu Asp Gln Phe Lys Gly Gln Gly Lys Lys His
        115                 120                 125

Phe Arg Asp Thr Val Gly His Gly Ser Asp Tyr Ser Leu Ser Glu Val
    130                 135                 140

Leu Trp Val Cys Ala Asn Leu Phe Ser Asp Val Gln Leu Lys Met Ser
145                 150                 155                 160

His Lys Arg Ile Met Leu Phe Thr Asn Glu Asp Pro His Gly Arg
            165                 170                 175

Asp Ser Ala Lys Ala Ser Arg Ala Arg Thr Lys Ala Ser Asp Leu Arg
            180                 185                 190

Asp Thr Gly Ile Phe Leu Asp Leu Met His Leu Lys Lys Pro Gly Gly
            195                 200                 205

Phe Asp Val Ser Val Phe Tyr Arg Asp Ile Ile Thr Thr Ala Glu Asp
    210                 215                 220

Glu Asp Leu Gly Val His Phe Glu Glu Ser Ser Lys Leu Glu Asp Leu
225                 230                 235                 240

Leu Arg Lys Val Arg Ala Lys Glu Thr Lys Lys Arg Val Leu Ser Arg
                245                 250                 255

Leu Lys Phe Lys Leu Gly Glu Asp Val Val Leu Met Val Gly Ile Tyr
            260                 265                 270

Asn Leu Val Gln Lys Ala Asn Lys Pro Phe Pro Val Arg Leu Tyr Arg
            275                 280                 285

Glu Thr Asn Glu Pro Val Lys Thr Lys Thr Arg Thr Phe Asn Val Asn
290                 295                 300

Thr Gly Ser Leu Leu Leu Pro Ser Asp Thr Lys Arg Ser Leu Thr Tyr
305                 310                 315                 320

Gly Thr Arg Gln Ile Val Leu Glu Lys Glu Thr Glu Glu Leu Lys
                325                 330                 335

Arg Phe Asp Glu Pro Gly Leu Ile Leu Met Gly Phe Lys Pro Thr Val
            340                 345                 350

Met Leu Lys Lys Gln His Tyr Leu Arg Pro Ser Leu Phe Val Tyr Pro
            355                 360                 365

Glu Glu Ser Leu Val Ser Gly Ser Ser Thr Leu Phe Ser Ala Leu Leu
            370                 375                 380

Thr Lys Cys Val Glu Lys Glu Val Ile Ala Val Cys Arg Tyr Thr Pro
385                 390                 395                 400

Arg Lys Asn Val Ser Pro Tyr Phe Val Ala Leu Val Pro Gln Glu Glu
                405                 410                 415

Glu Leu Asp Asp Gln Asn Ile Gln Val Thr Pro Gly Gly Phe Gln Leu
            420                 425                 430

Val Phe Leu Pro Tyr Ala Asp Asp Lys Arg Lys Val Pro Phe Thr Glu
            435                 440                 445

Lys Val Thr Ala Asn Gln Glu Gln Ile Asp Lys Met Lys Ala Ile Val
450                 455                 460

Gln Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495
```

```
Glu Ser Glu Gln Val Val Asp Leu Thr Leu Pro Lys Val Glu Ala Ile
                500                 505                 510

Lys Lys Arg Leu Gly Ser Leu Ala Asp Glu Phe Lys Glu Leu Val Tyr
            515                 520                 525

Pro Pro Gly Tyr Asn Pro Glu Gly Lys Val Ala Lys Arg Lys Gln Asp
        530                 535                 540

Asp Glu Gly Ser Thr Ser Lys Lys Pro Lys Val Glu Leu Ser Glu Glu
545                 550                 555                 560

Glu Leu Lys Ala His Phe Arg Lys Gly Thr Leu Gly Lys Leu Thr Val
                565                 570                 575

Pro Thr Leu Lys Asp Ile Cys Lys Ala His Gly Leu Lys Ser Gly Pro
            580                 585                 590

Lys Lys Gln Glu Leu Leu Asp Ala Leu Ile Arg His Leu Glu Lys Asn
        595                 600                 605

<210> SEQ ID NO 88
<211> LENGTH: 608
<212> TYPE: PRT
<213> ORGANISM: Rattus sp.

<400> SEQUENCE: 88

Met Ser Glu Trp Glu Ser Tyr Tyr Lys Thr Glu Gly Glu Glu Glu Glu
1               5                   10                  15

Glu Glu Glu Gln Ser Pro Asp Thr Asn Gly Glu Tyr Lys Tyr Ser Gly
                20                  25                  30

Arg Asp Ser Leu Ile Phe Leu Val Asp Ala Ser Arg Ala Met Phe Glu
            35                  40                  45

Ser Gln Gly Glu Asp Glu Leu Thr Pro Phe Asp Met Ser Ile Gln Cys
50                  55                  60

Ile Gln Ser Val Tyr Thr Ser Lys Ile Ile Ser Ser Asp Arg Asp Leu
65                  70                  75                  80

Leu Ala Val Val Phe Tyr Gly Thr Glu Lys Asp Lys Asn Ser Val Asn
                85                  90                  95

Phe Lys Ser Ile Tyr Val Leu Gln Asp Leu Asp Asn Pro Gly Ala Lys
            100                 105                 110

Arg Val Leu Glu Leu Asp Arg Phe Lys Gly Gln Gln Gly Lys Lys His
            115                 120                 125

Phe Arg Asp Thr Ile Gly His Gly Ser Asp Tyr Ser Leu Ser Glu Val
        130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asp Pro His Gly Asn
                165                 170                 175

Asp Ser Ala Lys Ala Ser Arg Ala Arg Thr Lys Ala Ser Asp Leu Arg
            180                 185                 190

Asp Thr Gly Ile Phe Leu Asp Leu Met His Leu Lys Lys Arg Gly Gly
        195                 200                 205

Phe Asp Val Ser Leu Phe Tyr Arg Asp Ile Ile Ser Ile Ala Glu Asp
        210                 215                 220

Glu Asp Leu Gly Val His Phe Glu Glu Ser Ser Lys Leu Glu Asp Leu
225                 230                 235                 240

Leu Arg Lys Val Arg Ala Lys Glu Thr Lys Lys Arg Val Leu Ser Arg
                245                 250                 255

Leu Lys Phe Lys Leu Gly Lys Asp Val Ala Leu Met Val Gly Val Tyr
            260                 265                 270
```

Asn Leu Val Gln Lys Ala Asn Lys Pro Phe Pro Val Arg Leu Tyr Arg
            275                 280                 285

Glu Thr Asn Glu Pro Val Lys Thr Lys Thr Arg Thr Phe Asn Val Asn
        290                 295                 300

Thr Gly Ser Leu Leu Pro Ser Asp Thr Lys Arg Ser Leu Thr Phe
305                 310                 315                 320

Gly Thr Arg Gln Ile Val Leu Glu Lys Glu Thr Glu Leu Lys
                325                 330                 335

Arg Phe Asp Glu Pro Gly Leu Ile Leu Met Gly Phe Lys Pro Met Val
            340                 345                 350

Met Leu Lys Asn His His Tyr Leu Arg Pro Ser Leu Phe Leu Tyr Pro
            355                 360                 365

Glu Glu Ser Leu Val Asn Gly Ser Ser Thr Leu Phe Ser Ala Leu Leu
        370                 375                 380

Thr Lys Cys Val Glu Lys Glu Val Ile Ala Val Cys Arg Tyr Thr Ala
385                 390                 395                 400

Arg Lys Asn Val Ser Pro Tyr Phe Val Ala Leu Val Pro Gln Glu Glu
                405                 410                 415

Glu Leu Asp Asp Gln Asn Ile Gln Val Thr Pro Ala Gly Phe Gln Leu
            420                 425                 430

Val Phe Leu Pro Tyr Ala Asp Asp Lys Arg Lys Val Pro Phe Thr Glu
        435                 440                 445

Lys Val Met Ala Asn Pro Glu Gln Ile Asp Lys Met Lys Ala Ile Val
            450                 455                 460

Gln Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495

Glu Ser Glu Gln Val Val Asp Leu Thr Leu Pro Lys Val Glu Ala Ile
            500                 505                 510

Lys Lys Arg Leu Gly Ser Leu Ala Asp Glu Phe Lys Glu Leu Val Tyr
        515                 520                 525

Pro Pro Gly Tyr Asn Pro Glu Gly Lys Ile Ala Lys Arg Lys Ala Asp
            530                 535                 540

Asn Glu Gly Ser Ala Ser Lys Lys Pro Lys Val Glu Leu Ser Glu Glu
545                 550                 555                 560

Glu Leu Lys Asp Leu Phe Ala Lys Gly Thr Leu Gly Lys Leu Thr Val
                565                 570                 575

Pro Ala Leu Arg Asp Ile Cys Lys Ala Tyr Gly Leu Lys Ser Gly Pro
            580                 585                 590

Lys Lys Gln Glu Leu Leu Glu Ala Leu Ser Arg His Leu Glu Lys Asn
        595                 600                 605

<210> SEQ ID NO 89
<211> LENGTH: 742
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ala Ala Asp Gly Tyr Leu Pro Asp Trp Leu Glu Asp Asn Leu Ser
1               5                   10                  15

-continued

```
Glu Gly Ile Arg Glu Trp Trp Ala Leu Lys Pro Gly Ala Pro Gln Pro
         20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
 50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

Asp Arg Leu Met Asn Pro Leu Ile Asp Gln Tyr Leu Tyr Leu Ser
            435                 440                 445

Lys Thr Ile Asn Gly Ser Gly Gln Asn Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Arg Val Ser Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Val Ser Ala
            580                 585                 590

Leu Lys Ala Gln Ala Gln Thr Gly Trp Val Gln Asn Gln Gly Ile Leu
        595                 600                 605

Pro Gly Met Val Trp Gln Asp Arg Asp Val Tyr Leu Gln Gly Pro Ile
    610                 615                 620

Trp Ala Lys Ile Pro His Thr Asp Gly Asn Phe His Pro Ser Pro Leu
625                 630                 635                 640

Met Gly Gly Phe Gly Met Lys His Pro Pro Gln Ile Leu Ile Lys
                645                 650                 655

Asn Thr Pro Val Pro Ala Asp Pro Pro Thr Ala Phe Asn Lys Asp Lys
            660                 665                 670

Leu Asn Ser Phe Ile Thr Gln Tyr Ser Thr Gly Gln Val Ser Val Glu
        675                 680                 685

Ile Glu Trp Glu Leu Gln Lys Glu Asn Ser Lys Arg Trp Asn Pro Glu
    690                 695                 700

Ile Gln Tyr Thr Ser Asn Tyr Lys Ser Asn Asn Val Glu Phe Ala
705                 710                 715                 720

Val Asn Thr Glu Gly Val Tyr Ser Glu Pro Arg Pro Ile Gly Thr Arg
                725                 730                 735

Tyr Leu Thr Arg Asn Leu
        740

<210> SEQ ID NO 90
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

-continued

```
Gly Tyr Lys Tyr Leu Gly Pro Gly Asn Gly Leu Asp Lys Gly Glu Pro
     50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460
```

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Thr Val Ser Ala
            580                 585                 590

Leu Phe Lys Ala Gln Ala Gln Thr Gly Trp Val Gln Asn Gln Gly Ile
            595                 600                 605

Leu Pro Gly Met Val Trp Gln Asp Arg Asp Val Tyr Leu Gln Gly Pro
610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
            645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
            725                 730                 735

Arg Tyr Leu Thr Arg Asn Leu
            740

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91 ggaacccta gtgatggagt t                                           21

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 92
cggcctcagt gagcga                                                    16

<210> SEQ ID NO 93
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 93

Arg Gly Gly Arg Leu Ser Tyr Ser Arg Arg Arg Phe Ser Thr Ser Thr
1               5                   10                  15

Gly Arg

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Ala Arg Ile Lys Pro Thr Phe Arg Arg Leu Lys Trp Lys Tyr Lys
1               5                   10                  15

Gly Lys Phe Trp
            20

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Leu Ser Ser Ile Phe Ser Arg Ile Gly Asp Pro
1               5                   10

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 97

Val Arg Leu Pro Pro Pro Val Arg Leu Pro Pro Pro Val Arg Leu Pro
1               5                   10                  15

Pro Pro

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Glu Leu Pro Pro Pro Val Glu Leu Pro Pro Pro Val Glu Leu Pro
1               5                   10                  15

Pro Pro

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Gly Thr Tyr Lys Lys Lys Leu Met Arg Ile Pro Leu Lys Gly Thr
1               5                   10                  15

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Pro Pro Arg Pro Pro Arg Pro Pro Arg
1               5

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Pro Arg Pro Pro Arg Pro Pro Arg Pro Pro Arg Pro Pro Arg
1               5                   10                  15

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Arg Arg Arg Arg Arg Arg Arg
1               5
```

```
<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Arg Arg Glu Arg Gln Ser Arg Leu Arg Arg Glu Arg Gln Ser Arg
1               5                   10                  15

<210> SEQ ID NO 104
<211> LENGTH: 9
<212> TYPE: PRT
<213> ORGANISM: Human immunodeficiency virus 1

<400> SEQUENCE: 104

Arg Lys Lys Arg Arg Gln Arg Arg Arg
1               5
```

METHODS AND COMPOSITIONS FOR DELIVERY OF AGENTS ACROSS THE BLOOD-BRAIN BARRIER

CLAIM OF PRIORITY

This application is a National Stage application under 35 U.S.C. § 371 of International Application No. PCT/US2019/041386, having an International Filing Date of Jul. 11, 2019, which claims the benefit of U.S. Provisional Application Ser. No. 62/696,422, filed on Jul. 11, 2018. The entire contents of the foregoing are incorporated herein by reference.

SEQUENCE LISTING

The instant application contains a Sequence Listing which has been submitted electronically in ASCII format and is hereby incorporated by reference in its entirety. Said ASCII copy, created on Jul. 11, 2019, is named 29618-0200W01_SL.txt and is 58,834 bytes in size.

TECHNICAL FIELD

Described herein are sequences that enhance permeation of agents across the blood brain barrier, compositions comprising the sequences, and methods of use thereof.

BACKGROUND

Delivery of therapeutic agents, including gene therapy reagents, is an impediment to development of treatments for a number of conditions. The blood-brain barrier (BBB) is a key obstacle for drug delivery to the mammalian central nervous system (CNS), particularly for delivery to the human brain, to treat conditions including neurodegenerative diseases such as Parkinson's disease; Alzheimer's disease; Huntington's disease; Amyotrophic lateral sclerosis; and Multiple sclerosis.

SUMMARY

The present invention is based on the development of artificial targeting sequences that enhance permeation of agents into cells and across the blood brain barrier.

Thus provided herein is an AAV capsid protein, e.g., an engineered AAV capsid protein, comprising a targeting sequence that comprises at least four contiguous amino acids from the sequence TVSALFK (SEQ ID NO:8); TVSALK (SEQ ID NO:4); KLASVT (SEQ ID NO:83); or KFLASVT (SEQ ID NO:84). In some embodiments, the AAV capsid protein comprises a targeting sequence that comprises at least five contiguous amino acids from the sequence TVSALK (SEQ ID NO:4); TVSALFK (SEQ ID NO:8); KLASVT (SEQ ID NO:83); or KFLASVT (SEQ ID NO: 84). In some embodiments, the AAV capsid protein comprises a targeting sequence that comprises at least six contiguous amino acids from the sequence TVSALK (SEQ ID NO:4); TVSALFK (SEQ ID NO:8); KLASVT (SEQ ID NO:83); or KFLASVT (SEQ ID NO:84).

In some embodiments, the AAV is AAV9; other AAV as known in the art (e.g., AAV1, 2, 3, 4, 5, 6, 7, 8 and variants thereof and others as known in the art or described herein) can also be used.

In some embodiments, the AAV capsid protein comprises AAV9 VP1 (e.g., SEQ ID NO:85).

In some embodiments, the targeting sequence is inserted in the capsid protein at a position corresponding to between amino acids 588 and 589 of SEQ ID NO:85.

Also provided herein are nucleic acids encoding the AAV capsid proteins comprising a targeting sequence as described herein.

In addition, provided herein is an AAV comprising a capsid protein comprising a targeting sequence as described herein. In some embodiments, AAV further comprises a transgene, preferably a therapeutic or diagnostic transgene. Therapeutic transgenes can include, e.g., cDNAs that restore protein function, guide RNA for gene editing, RNA, or miRNA.

Also provided herein are targeting sequences comprising V[S/p][A/m/t/]L (SEQ ID NO:79), TV[S/p][A/m/t/]L (SEQ ID NO:80), TV[S/p][A/m/t/]LK (SEQ ID NO:81), or TV[S/p][A/m/t/]LFK. (SEQ ID NO:82). In some embodiments, the targeting sequence comprises VPALR (SEQ ID NO: 1); VSALK (SEQ ID NO:2); TVPALR (SEQ ID NO:3); TVSALK (SEQ ID NO:4); TVPMLK (SEQ ID NO: 12); TVPTLK (SEQ ID NO:13); FTVSALK (SEQ ID NO:5); LTVSALK (SEQ ID NO:6); TVSALFK (SEQ ID NO:8); TVPALFR (SEQ ID NO:9); TVPMLFK (SEQ ID NO:10) or TVPTLFK (SEQ ID NO:11). Also provided are fusion proteins comprising the targeting sequences linked to a heterologous (e.g., non-AAV VP1) sequence, and AAV capsid proteins (e.g., AAV9 VP1) comprising the targeting sequence. In some embodiments, the targeting sequence is inserted in a position corresponding to amino acids 588 and 589 of SEQ ID NO:85.

Additionally provided herein are nucleic acids encoding the targeting sequences, fusion proteins or AAV capsid proteins described herein, as well as AAV comprising the capsid proteins comprising a targeting sequence. In some embodiments, the AAV further comprises a transgene, preferably a therapeutic or diagnostic transgene. Therapeutic transgenes can include, e.g., cDNAs that restore protein function, guide RNA for gene editing, RNA, or miRNA.

Further, provided herein are methods of delivering a transgene to a cell, the method comprising contacting the cell with an AAV or fusion protein described herein. In some embodiments, the cell is in a living subject, e.g., a mammalian subject. In some embodiments, the cell is in a tissue selected from the brain, spinal cord, dorsal root ganglion, heart, or muscle, and a combination thereof. In some embodiments, the cell is a neuron (optionally a dorsal root ganglion neuron), astrocyte, cardiomyocyte, or myocyte.

In some embodiments, the subject has a neurodegenerative disease, epilepsy; stroke; spinocerebellar ataxia; Canavan's disease; Metachromatic leukodystrophy; Spinal muscular atrophy; Friedreich's ataxia; X-linked centronuclear myopathy; Lysosomal storage disease; Barth syndrome; Duchenne muscular dystrophy; Wilson's disease; or Crigler-Najjar syndrome type 1. In some embodiments, the neurodegenerative disease is Parkinson's disease; Alzheimer's disease; Huntington's disease; Amyotrophic lateral sclerosis; and Multiple sclerosis.

In some embodiments, the subject has a brain cancer, and the method includes administering an AAV encoding an anti-cancer agent. In some embodiments, the anti-cancer agent is HSV.TK1, and the method further comprises administering ganciclovir.

In some embodiments, the cell is in the brain of the subject, and the AAV is administered by parenteral delivery (e.g., via intravenous, intraarterial, subcutaneous, intraperitoneal, or intramuscular delivery); intracerebral; or intrathecal delivery (e.g., via lumbar injection, cisternal *magna* injection, or intraparenchymal injection).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a 3D model of an AAV9 virus. Individual CPP inserted into the capsid between amino acids 588 and 589 (VP1 numbering) will be displayed at the 3-fold axis where receptor binding presumably occurs. FIG. 1B illustrate the method of individual AAV production. Three plasmids including pRC (engineered or not), pHelper and pAAV are co-transfected into HEK 293T cells, with AAVs harvested and purified using iodixanol gradient.

In FIG. 2B, * P<0.05, vs. AAV9, ANOVA.

In FIG. 2D, * P<0.05, ** P<0.01, vs. AAV9, ANOVA.

FIG. 3A depicts the optimization of the BIP targeting sequence in order to further engineer AAV9 towards better brain transduction. BIP1 (VPALR, SEQ ID NO:1), which enables AAV9 to transduce brain more efficiently (as in AAV.CPP.11), is derived from the protein Ku70 in rats. Human, mouse and rat Ku70 proteins differ in their exact amino acid sequences. BIP2 (VSALK, SEQ ID NO:2) as in AAV.CPP.12 is a "synthetic" peptide related to BIP1. Further engineering focuses on the VSALK sequence in the hope of minimizing species specificity of final engineered AAV. To generate new targeting sequence, amino acids of interest are added to the VSALK sequence, and in other cases positions of individual amino acids are switched. All new BIP2-derived sequences are again inserted into the AAV9 capsid to generate new candidate AAVs for screening. Sequences appearing in order are SEQ ID NOs: 69, 70, 71, 1-6, 72, 7, and 8.

In FIG. 3C, * P<0.05,  P<0.01, * P<0.001, vs. AAV9, ANOVA.

FIG. 4A illustrates the spheroid comprising human microvascular endothelial cells, which forms a barrier at the surface, and human pericyte and astrocytes inside the spheriod. Candidate AAVs were assessed for their ability to penetrate from the surrounding medium into the inside of the spheroid and to transduce the cells inside. FIG. 4B-4D shows images of AAV9, AAV.CPP.16 and AAV.CPP.21 treated spheroids. FIG. 4E shows relative RFP intensity of different AAV treated spheroids. *** P<0.001, vs. AAV9, ANOVA.

In FIG. 5B, * P<0.05, *** P<0.001, ANOVA.

In FIG. 6B, *** P<0.001, ANOVA.

In FIG. 7B, * P<0.05, Student test.

6J mice (6 weeks old). Percentage of RFP-labeled cells relative to all DAPI-stained cells is presented. * P<0.05, Student test.

Figure 9A:
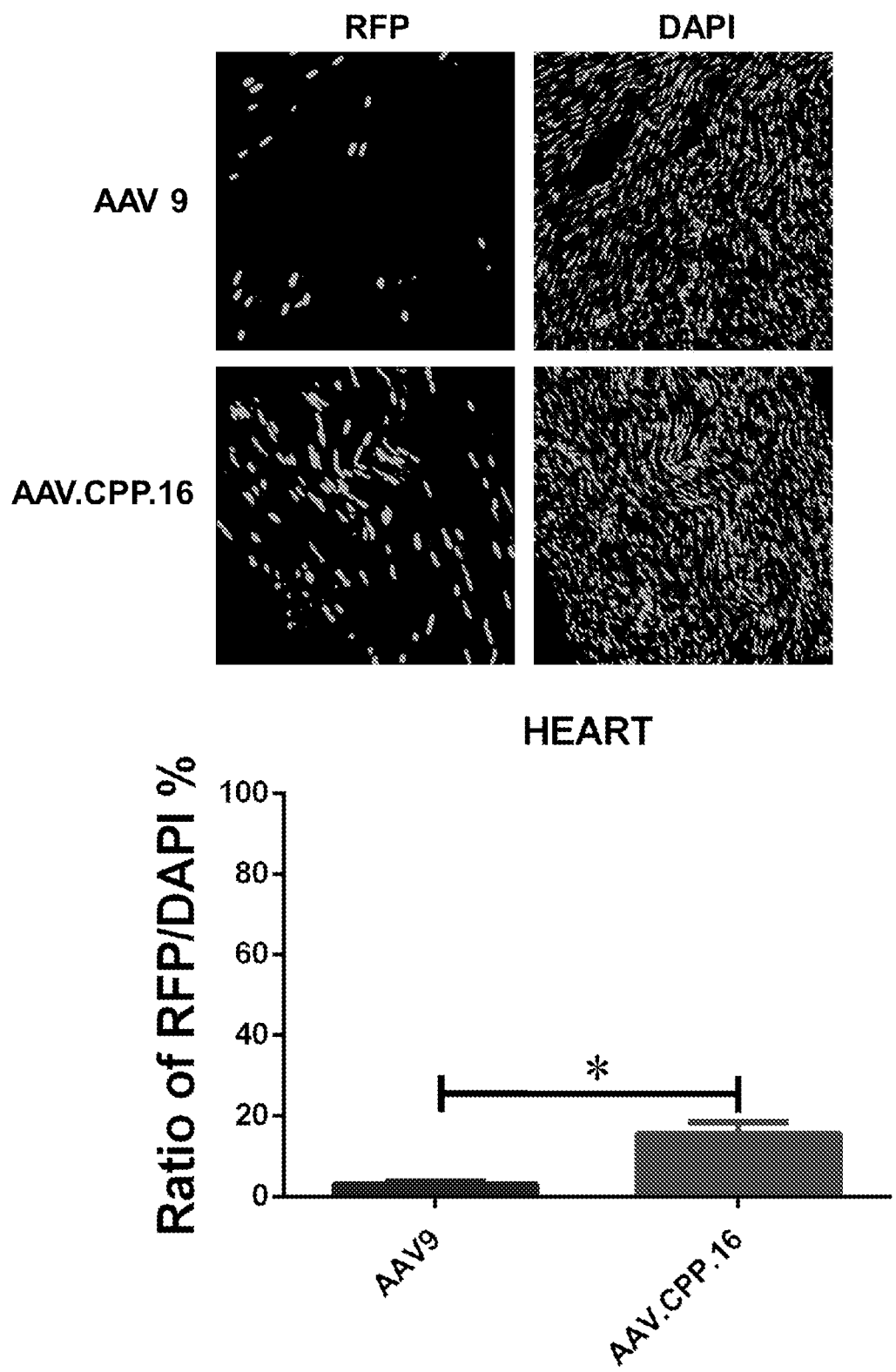
FIG. 9A depicts that AAV.CPP.16 shows enhanced ability vs. AAV9 in targeting the heart in adult mice. AAVs of $1\times10^{11}$ vg were administered intravenously in adult C57BL/
Figure 9B:
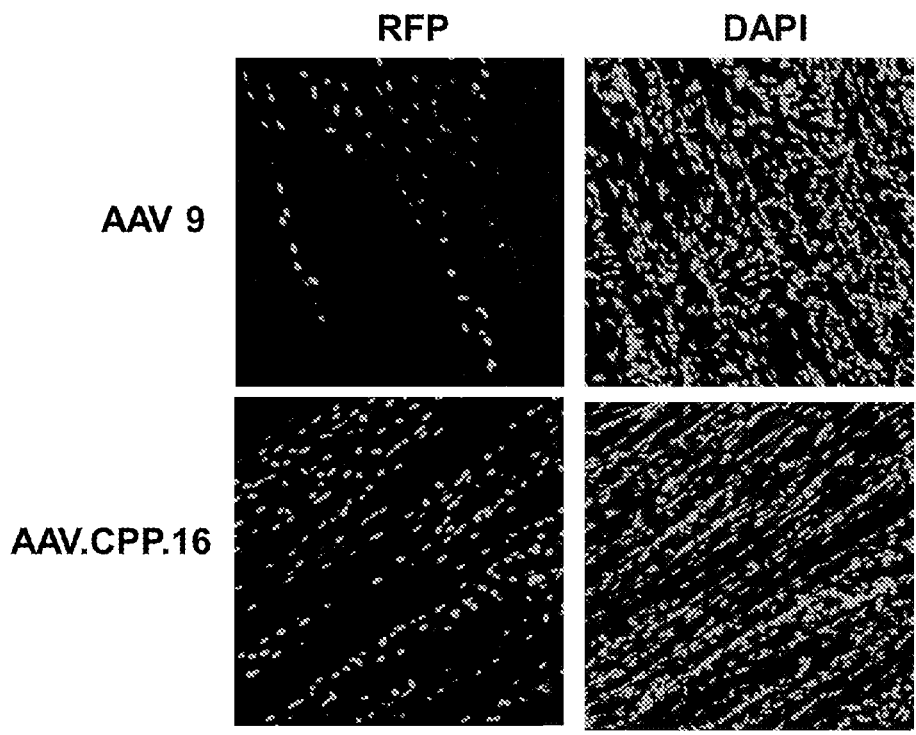
Figure 9B:
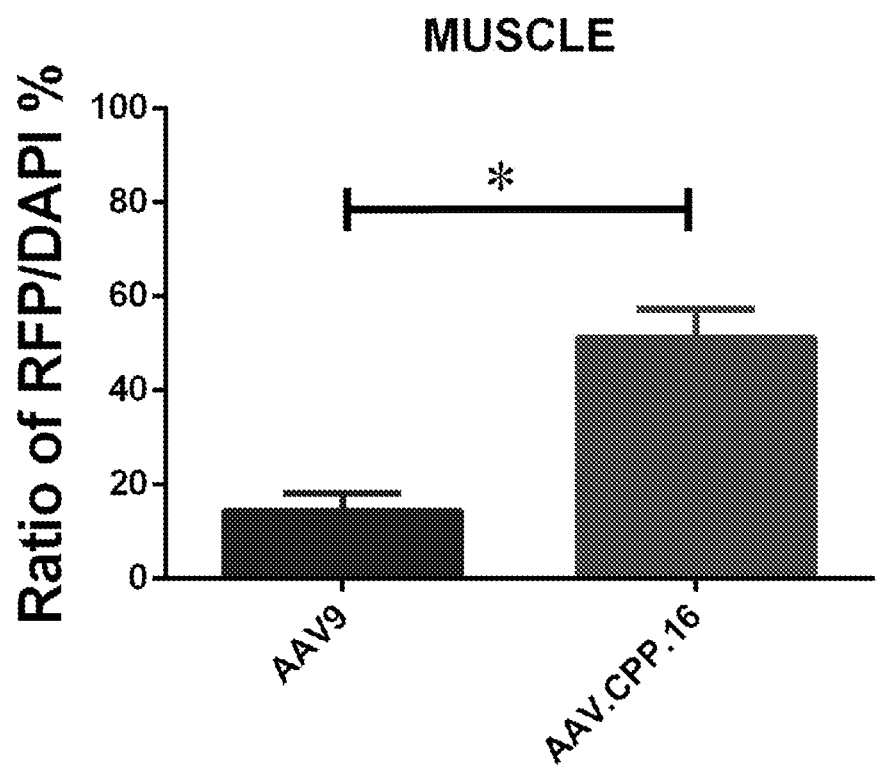

FIG. 9B depicts that AAV.CPP.16 shows enhanced ability vs. AAV9 in targeting the skeletal muscle in adult mice. AAVs of $1\times10^{11}$ vg were administered intravenously in adult C57BL/6J mice (6 weeks old). Percentage of RFP-labeled cells relative to all DAPI-stained cells is presented. * P<0.05, Student test.

Figure 9C:
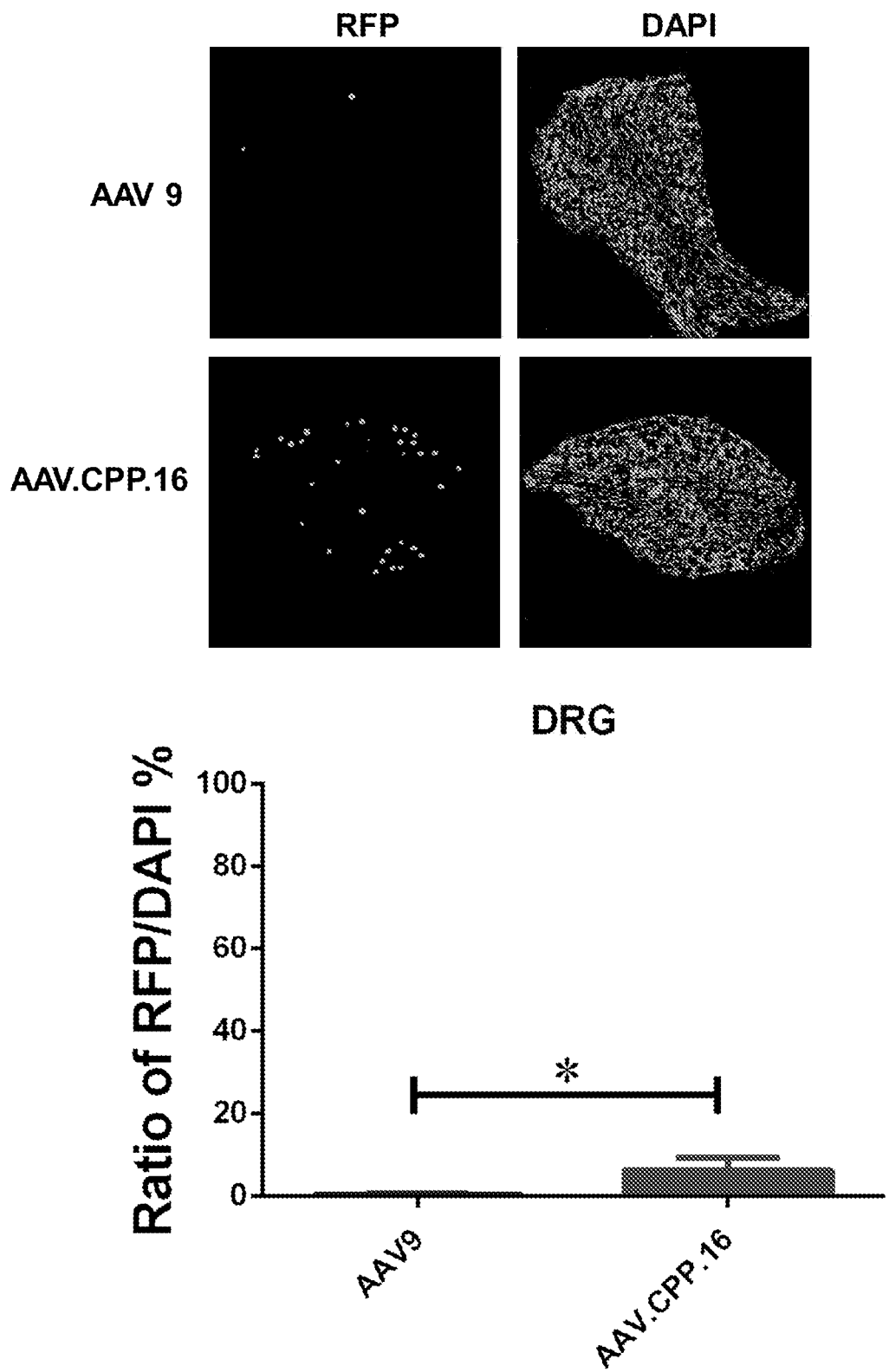

FIG. 9C depicts that AAV.CPP.16 shows enhanced ability vs. AAV9 in targeting the dorsal root ganglion (DRG) in adult mice. AAVs of $1\times10^{11}$ vg were administered intravenously in adult C57BL/6J mice (6 weeks old). Percentage of RFP-labeled cells relative to all DAPI-stained cells is presented. * P<0.05, Student test.

Figure 10A:
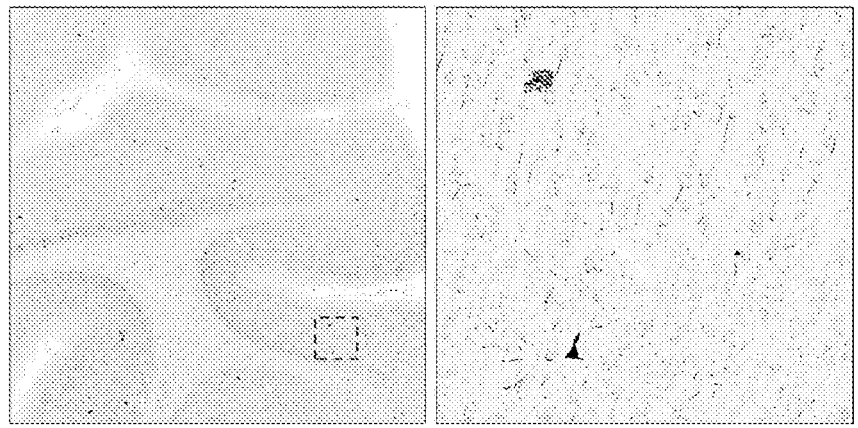
Figure 10A:
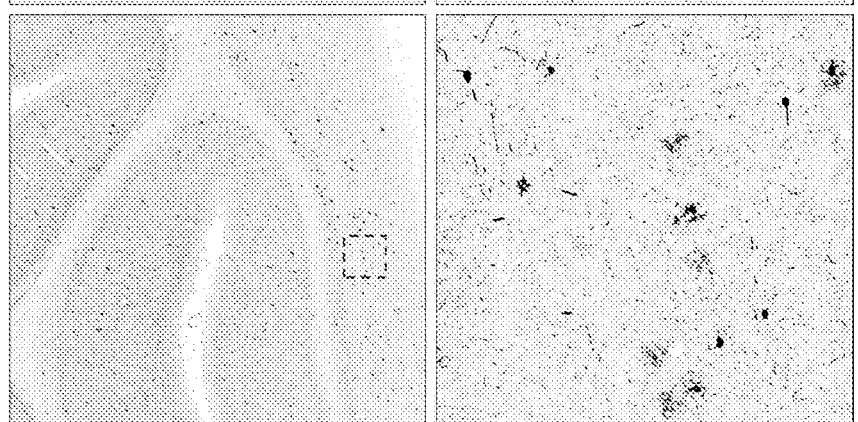
Figure 10A:
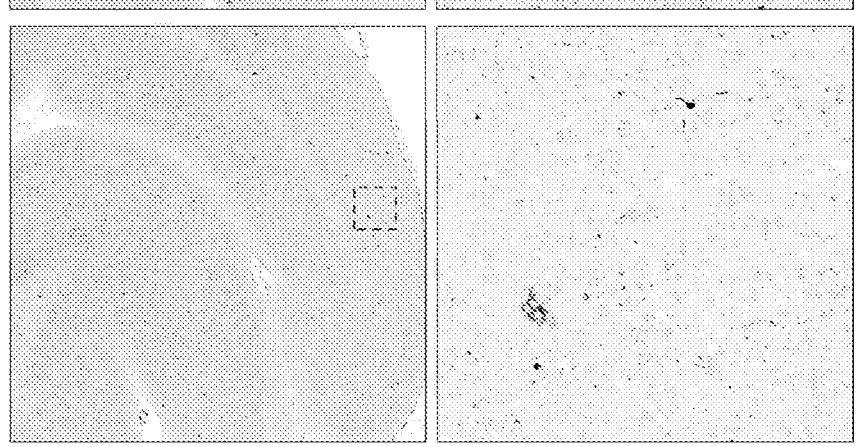

FIG. 10A depicts that AAV.CPP.16 and AAV.CPP.21 show enhanced ability vs. AAV9 to transduce brain cells in primary visual cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10B:
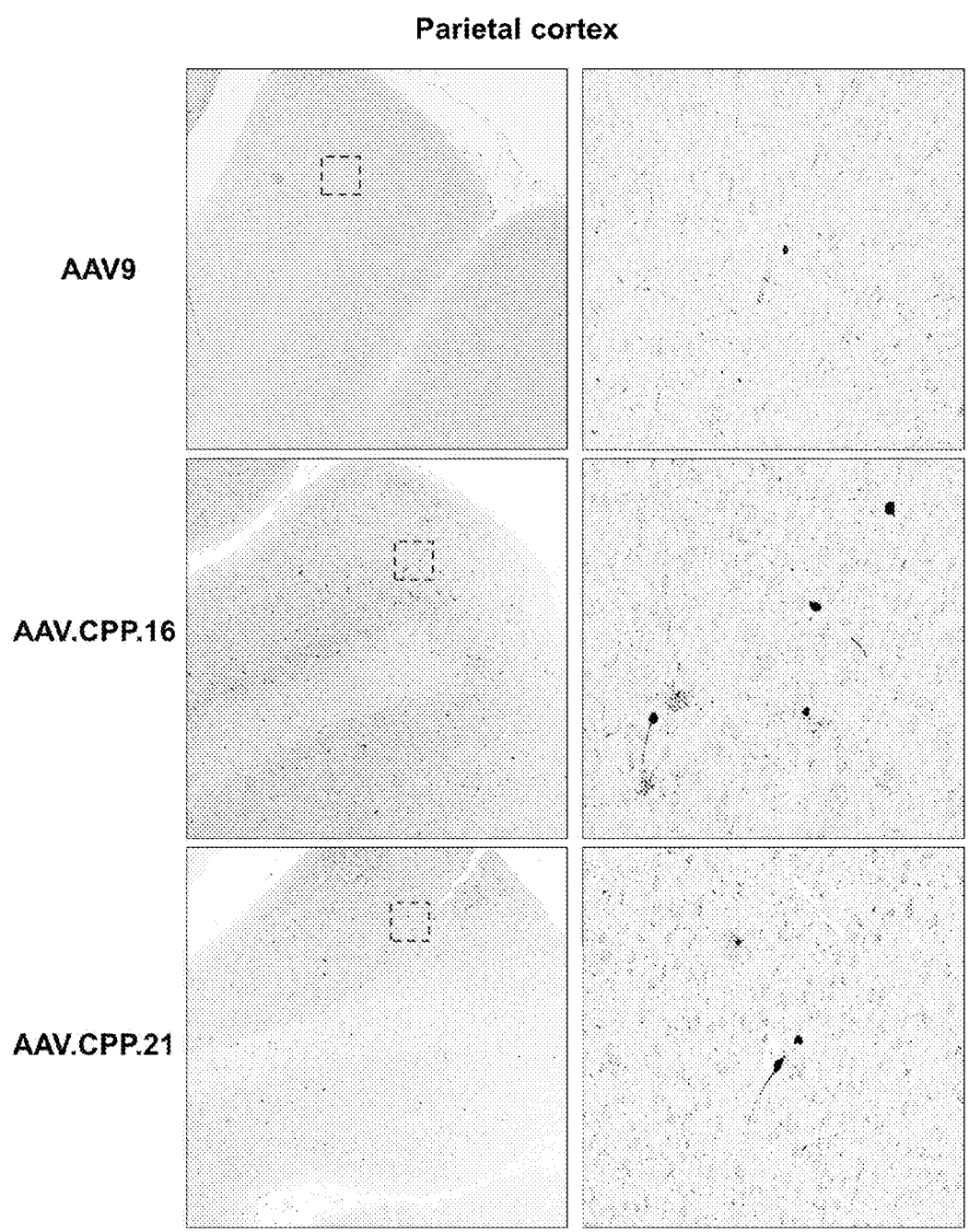

FIG. 10B depicts that AAV.CPP.16 and AAV.CPP.21 show enhanced ability vs. AAV9 to transduce brain cells in parietal cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10C:
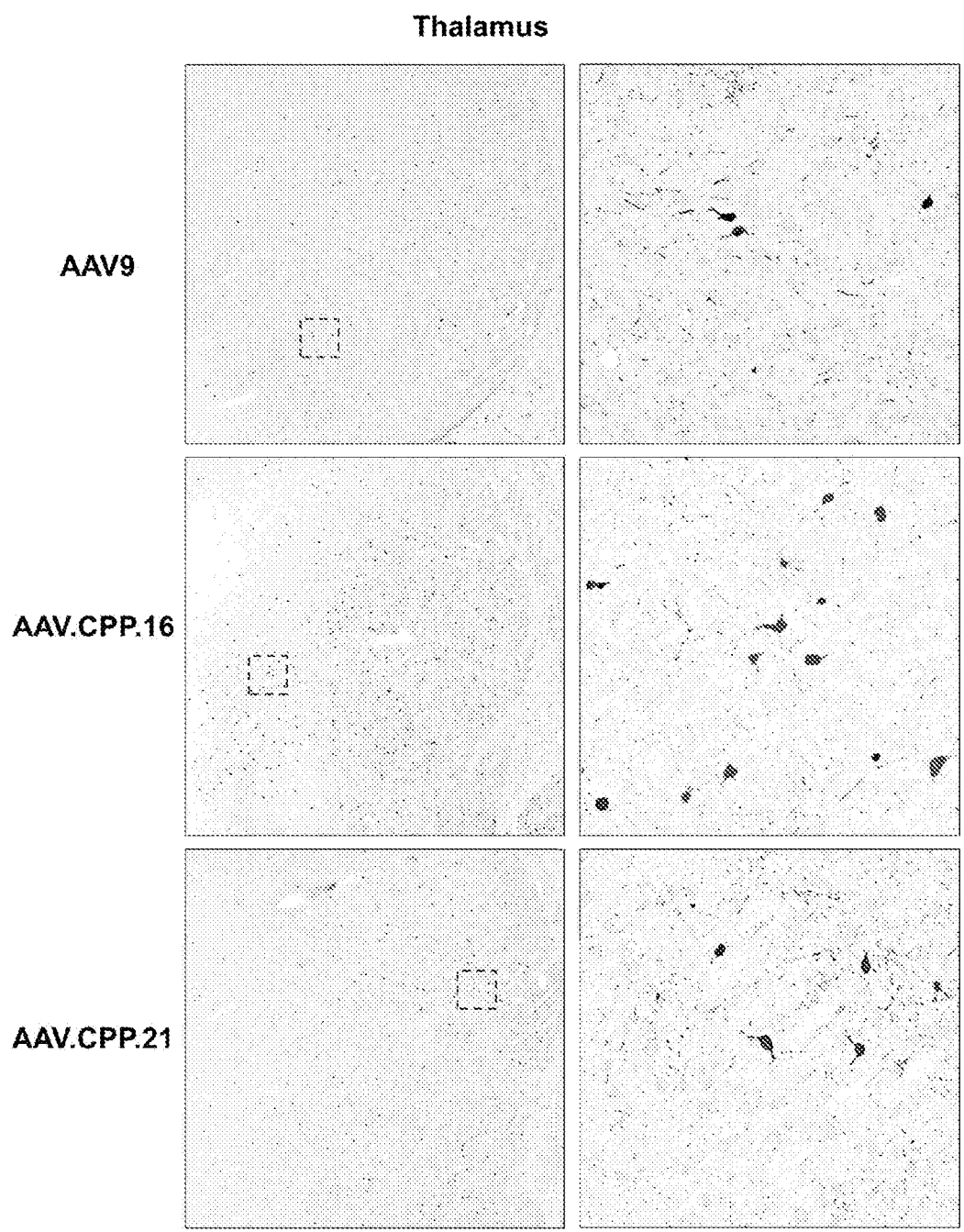

FIG. 10C depicts that AAV.CPP.16 and AAV.CPP.21 show enhanced ability vs. AAV9 to transduce brain cells in thalamus after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.

Figure 10D:
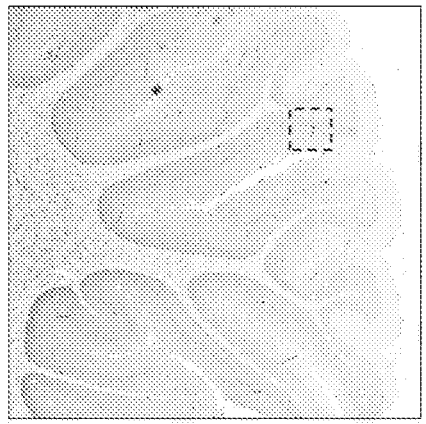
Figure 10D:
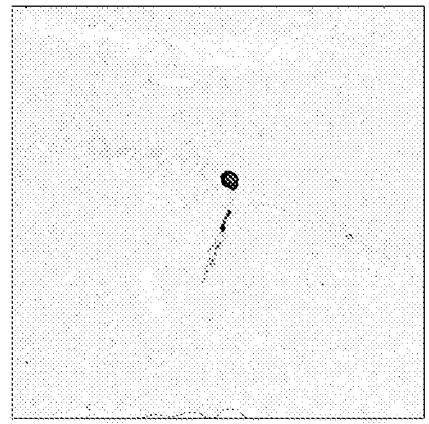
Figure 10D:
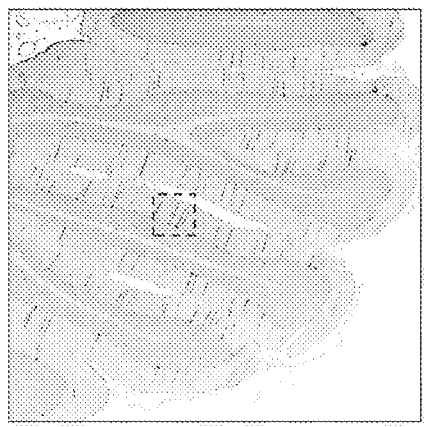
Figure 10D:
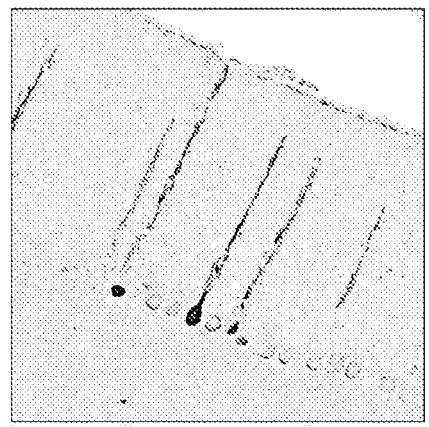
Figure 10D:
Figure 10D:
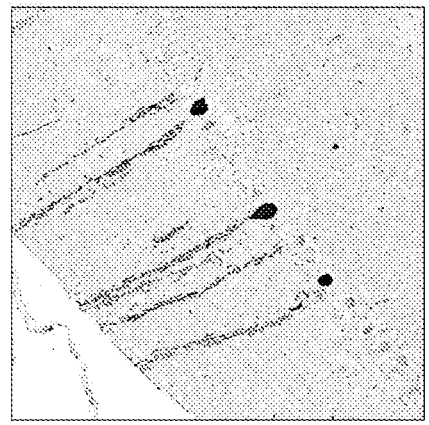

FIG. 10D depicts that AAV.CPP.16 and AAV.CPP.21 show enhanced ability vs. AAV9 to transduce brain cells in cerebellum after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. Both AAV.CPP.16 and AAV.CPP.21 transduced significantly more cells vs. AAV9.

Figure 11A:
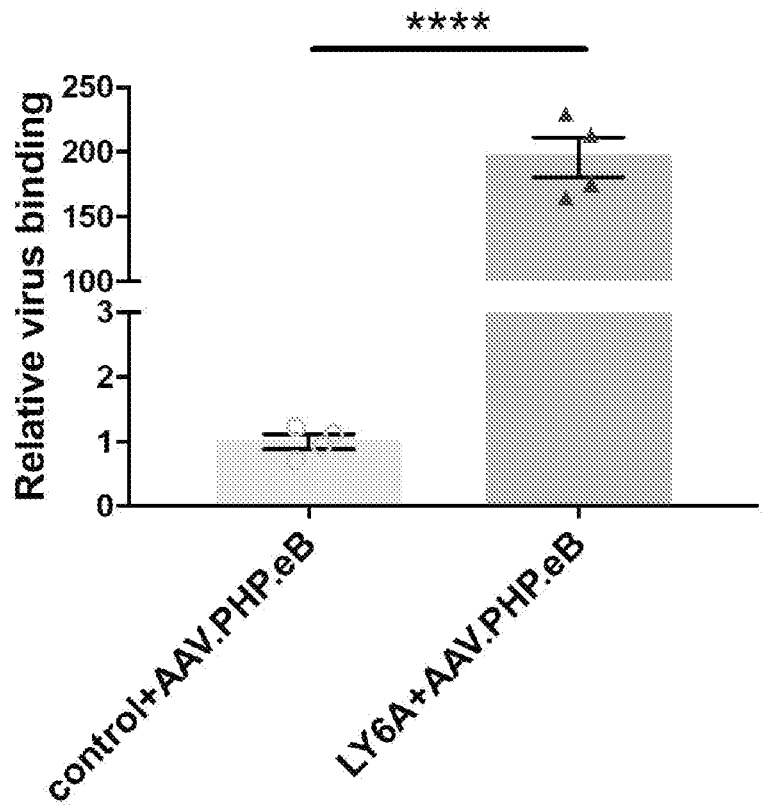
Figure 11B:
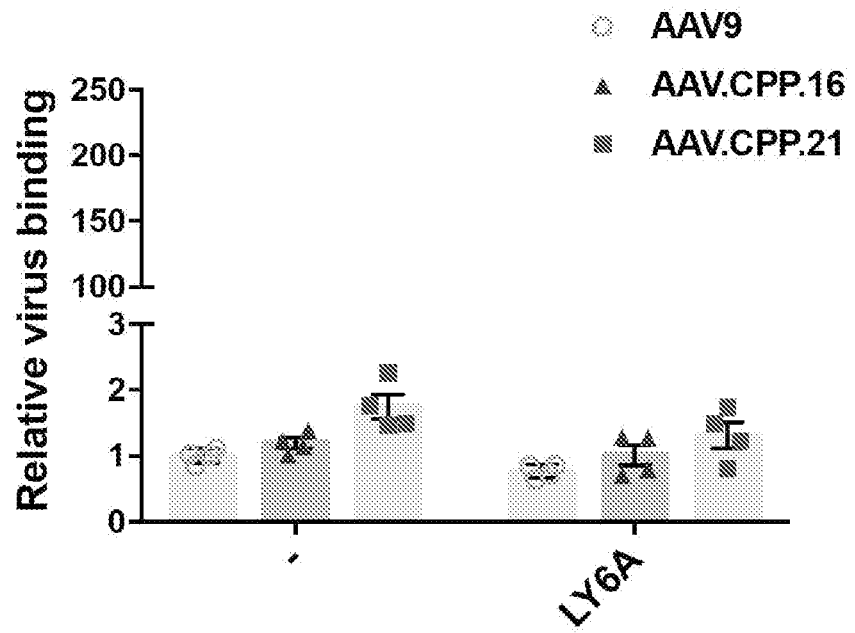

FIGS. 11A-11B depict that AAV.CPP.16 and AAV.CPP.21 do not bind to LY6A. LY6A serves as a receptor for AAV.PHP.B and its variants including AAV.PHP.eB (as in U.S. Pat. No. 9,102,949, US20170166926) and mediates AAV.PHP.eB's robust effect in crossing the BBB in certain mouse strains (Hordeaux et al. Mol Ther 2019 27(5):912-921; Huang et al. 2019, dx.doi.org/10.1101/538421). Overexpressing mouse LY6A in cultured 293 cells significantly increases binding of AAV.PHP.eB to the cell surface (FIG. 11A). On the contrary, over-expressing LY6A does not increase viral binding for AAV9, AAV.CPP.16 or AAV.CPP.21 (FIG. 11B). This suggests AAV.CPP.16 or AAV.CPP.21 does not share LY6A with AAV.PHP.eB as a receptor.

Figure 12A:
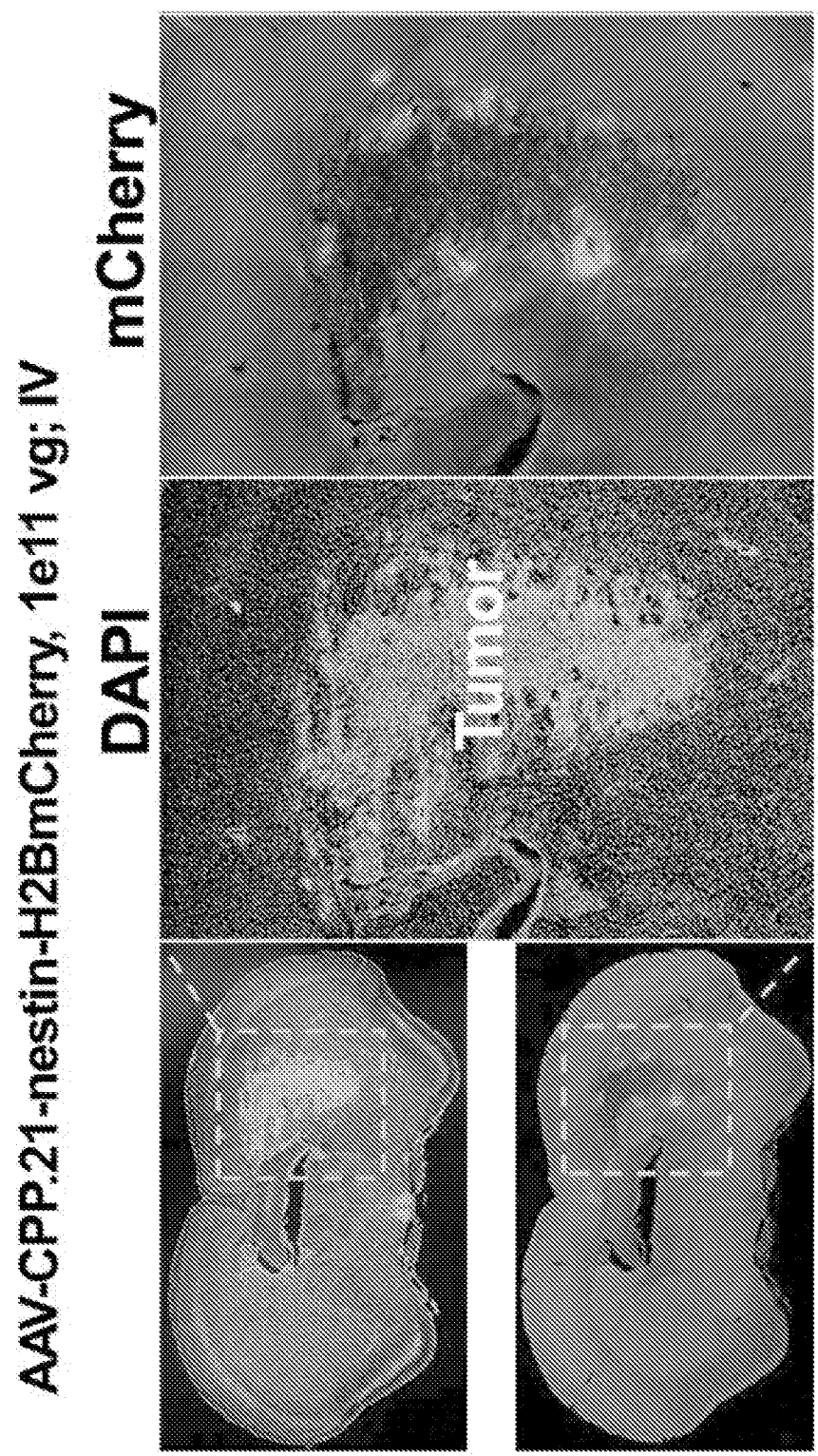
Figure 12B:
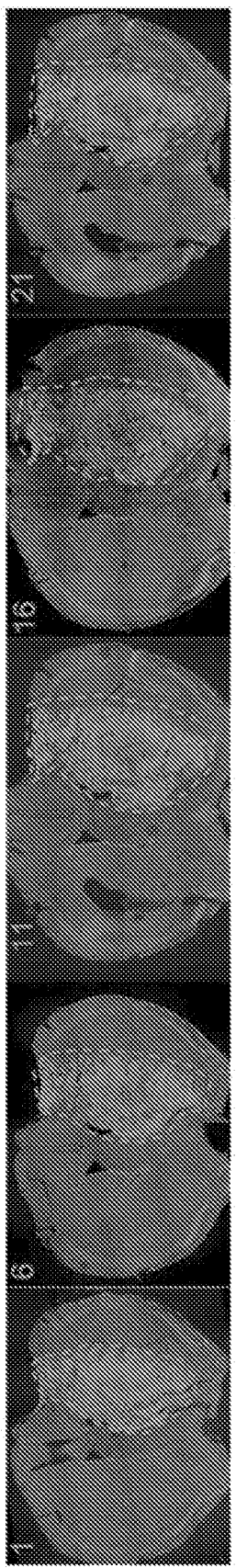
Figure 12B:
Figure 12C:
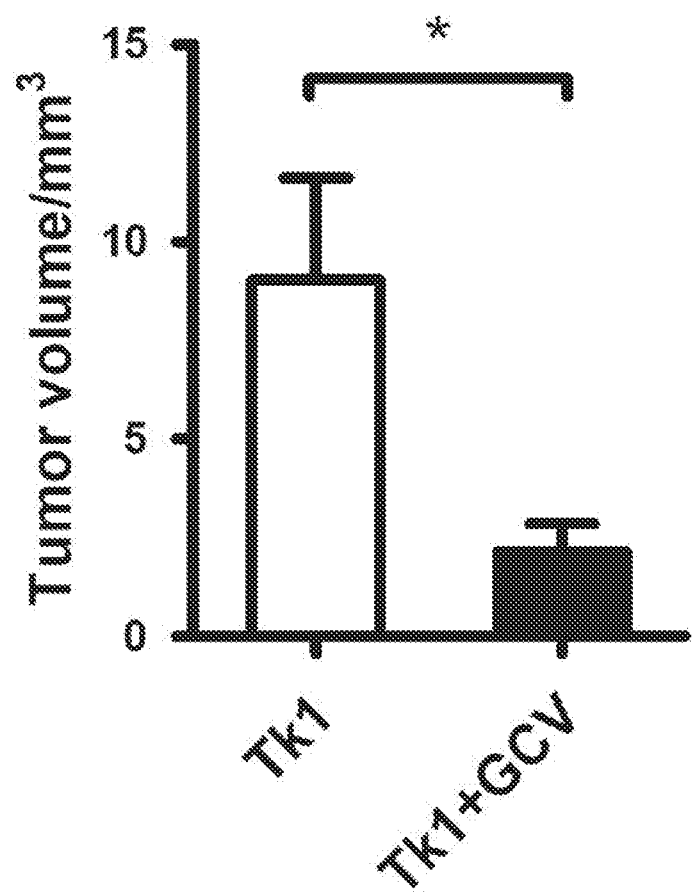

FIGS. 12A-12C depict that AAV.CPP.21 can be used to systemically deliver a therapeutic gene into brain tumor in a mouse mode of glioblastoma (GBM). As in FIG. 11A, intravenously administered AAV.CPP.21-H2BmCherry was shown to target tumor mass, especially the tumor expanding frontier. In FIG. 11B-11C, using AAV.CPP.21 to systemically deliver the "suicide gene" HSV.TK1 results in shrinkage of brain tumor mass, when combined with the pro-drug ganciclovir. HSV.TK1 turns the otherwise "dormant" ganciclovir into a tumor-killing drug. * P<0.05, Student test.

Figure 13:
Figure 13:

FIG. 13 depicts that when injected locally into adult mouse brain, AAV.CPP.21 resulted in more widespread and robust transduction of brain tissue in comparison with AAV9. Intracerebral injection of AAVs ($1\times10^{11}$ vg) was performed in adult mice (>6 weeks old) and brain tissues were harvested and examined 3 weeks after AAV injection. ** P<0.01, Student test.

DETAILED DESCRIPTION

Difficulties associated with delivery across the BBB have hindered development of therapeutic agents to treat brain disorders including cancer and neurodegenerative disorders. Adeno-associated virus (AAV) has emerged as an important research and clinical tool for delivering therapeutic genes to the brain, spinal cord and the eye; see, e.g., U.S. Pat. Nos. 9,102,949; 9,585,971; and US20170166926. However, existing AAVs including AAV9 have either limited efficiency in crossing the BBB, or only work in some non-primate species.

Through rational design and targeted screening on the basis of known cell-penetrating peptides (CPPs) (see, e.g., Gomez et al., *Bax-inhibiting peptides derived from Ku70 and cell-penetrating pentapeptides*. Biochem. Soc. Trans. 2007; 35(Pt 4):797-801), targeting sequences have been discovered that, when engineered into the capsid of an AAV, improved the efficiency of gene delivery to the brain by up to three orders of magnitude. These methods were used to engineer one such AAV vector that dramatically reduced tumor size in an animal model of glioblastoma.

Targeting Sequences

The present methods identified a number of potential targeting peptides that enhance permeation through the BBB, e.g., when inserted into the capsid of an AAV, e.g., AAV1, AAV2, AAV8, or AAV9, or when conjugated to a biological agent, e.g., an antibody or other large biomolecule, either chemically or via expression as a fusion protein.

In some embodiments, the targeting peptides comprise sequences of at least 5 amino acids. In some embodiments, the amino acid sequence comprises at least 4, e.g., 5, contiguous amino acids of the sequences VPALR (SEQ ID NO:1) and VSALK (SEQ ID NO:2).

In some embodiments, the targeting peptides comprise a sequence of $X_1\ X_2\ X_3\ X_4\ X_5$, wherein:

(i) $X_1$, $X_2$, $X_3$, $X_4$ are any four non-identical amino acids of V, A, L, I, G, P, S, T, or M; and (ii) $X_5$ is K, R, H, D, or E (SEQ ID NO:73).

In some embodiments, the targeting peptides comprise sequences of at least 6 amino acids. In some embodiments, the amino acid sequence comprises at least 4, e.g., 5 or 6 contiguous amino acids of the sequences TVPALR (SEQ ID NO:3), TVSALK (SEQ ID NO:4), TVPMLK (SEQ ID NO:12) and TVPTLK (SEQ ID NO:13).

In some embodiments, the targeting peptides comprise a sequence of $X_1 X_2 X_3 X_4 X_5 X_6$, wherein:
  (i) $X_1$ is T;
  (ii) $X_2, X_3, X_4, X_5$ are any four non-identical amino acids of V, A, L, I, G, P, S, T, or M; and
  (iii) $X_6$ is K, R, H, D, or E (SEQ ID NO:74).

In some embodiments, the targeting peptides comprise a sequence of $X_1 X_2 X_3 X_4 X_5 X_6$, wherein:
  (i) $X_1, X_2, X_3, X_4$ are any four non-identical amino acids from V, A, L, I, G, P, S, T, or M;
  (ii) $X_5$ is K, R, H, D, or E; and
  (iii) $X_6$ is E or D (SEQ ID NO:75).

In some embodiments, the targeting peptides comprise sequences of at least 7 amino acids. In some embodiments, the amino acid sequence comprises at least 4, e.g., 5, 6, or 7 contiguous amino acids of the sequences FTVSALK (SEQ ID NO:5), LTVSALK (SEQ ID NO:6), TVSALFK (SEQ ID NO:8), TVPALFR (SEQ ID NO:9), TVPMLFK (SEQ ID NO:10) and TVPTLFK (SEQ ID NO:11). In some other embodiments, the targeting peptides comprise a sequence of $X_1 X_2 X_3 X_4 X_5 X_6 X_7$, wherein:
  (i) $X_1$ is F, L, W, or Y;
  (ii) $X_2$ is T;
  (iii) $X_3, X_4, X_5, X_6$ are any four non-identical amino acids of V, A, L, I, G, P, S, T, or M; and
  (iv) $X_7$ is K, R, H, D, or E (SEQ ID NO:76).

In some embodiments, the targeting peptides comprise a sequence of $X_1 X_2 X_3 X_4 X_5 X_6 X_7$, wherein:
  (i) $X_1$ is T;
  (ii) $X_2, X_3, X_4, X_5$ are any four non-identical amino acids of V, A, L, I, G, P, S, T, or M;
  (iii) $X_6$ is K, R, H, D, or E; and
  (iv) $X_7$ is E or D (SEQ ID NO:77).

In some embodiments, the targeting peptides comprise a sequence of $X_1 X_2 X_3 X_4 X_5 X_6 X_7$, wherein:
  (i) $X_1, X_2, X_3, X_4$ are any four non-identical amino acids of V, A, L, I, G, P, S, T, or M;
  (ii) $X_5$ is K, R, H, D, or E;
  (iii) $X_6$ is E or D; and
  (iv) $X_7$ is A or I (SEQ ID NO:78).

In some embodiments, the targeting peptides comprise a sequence of V[S/p][A/m/t/]L (SEQ ID NO:79), wherein the upper case letters are preferred at that position. In some embodiments, the targeting peptides comprise a sequence of TV[S/p][A/m/t/]L (SEQ ID NO:80). In some embodiments, the targeting peptides comprise a sequence of TV[S/p][A/m/t/]LK (SEQ ID NO:81). In some embodiments, the targeting peptides comprise a sequence of TV[S/p][A/m/t/]LFK. (SEQ ID NO:82).

In some embodiments, the targeting peptide does not consist of VPALR (SEQ ID NO:1) or VSALK (SEQ ID NO:2).

Specific exemplary amino acid sequences that include the above mentioned 5, 6, or 7-amino acid sequences are listed in Table 1.

TABLE 1

Targeting Sequences

| SEQ ID NO: | Targeting Peptide Sequence |
| --- | --- |
| 1. | VPALR |
| 2. | VSALK |
| 3. | TVPALR |
| 4. | TVSALK |
| 5. | FTVSALK |
| 6. | LTVSALK |
| 7. | TFVSALK |
| 8. | TVSALFK |
| 9. | TVPALFR |
| 10. | TVPMLFK |
| 11. | TVPTLFK |
| 12. | TVPMLK |
| 13. | TVPTLK |
| 14. | VPMLK |
| 15. | VPTLK |
| 16. | VPMLKE |
| 17. | VPTLKD |
| 18. | VPALRD |
| 19. | VSALKE |
| 20. | VSALKD |
| 21. | TAVSLK |
| 22. | TALVSK |
| 23. | TVLSAK |
| 24. | TLVSAK |
| 25. | TMVPLK |
| 26. | TMLVPK |
| 27. | TVLPMK |
| 28. | TLVPMK |
| 29. | TTVPLK |
| 30. | TTLVPK |
| 31. | TVLPTK |
| 32. | TLVPTK |
| 33. | TAVPLR |
| 34. | TALVPR |
| 35. | TVLPAR |
| 36. | TLVPAR |
| 37. | TAVSLKE |
| 38. | TALVSKE |
| 39. | TVLSAKE |
| 40. | TLVSAKE |
| 41 | TMVPLKE |
| 42. | TMLVPKE |
| 43. | TVLPMKE |
| 44. | TLVPMKE |
| 45. | TTVPLKD |
| 46. | TTLVPKD |
| 47. | TVLPTKD |
| 48. | TLVPTKD |
| 49. | TAVPLRD |
| 50. | TALVPRD |
| 51. | TVLPARD |
| 52. | TLVPARD |
| 53. | TAVSLFK |
| 54 | TALVSFK |
| 55. | TVLSAFK |
| 56 | TLVSAFK |
| 57. | TMVPLFK |
| 58. | TMLVPFK |
| 59. | TVLPMFK |
| 60. | TLVPMFK |
| 61. | TTVPLFK |
| 62. | TTLVPFK |
| 63. | TVLPTFK |
| 64. | TLVPTFK |
| 65. | TAVPLFR |
| 66. | TALVPFR |
| 67. | TVLPAFR |
| 68. | TLVPAFR |

Targeting peptides including reversed sequences can also be used, e.g., KLASVT (SEQ ID NO:83) and KFLASVT (SEQ ID NO:84).

Targeting peptides disclosed herein can be modified according to the methods known in the art for producing peptidomimetics. See, e.g., Qvit et al., Drug Discov Today.

2017 February; 22(2): 454-462; Farhadi and Hashemian, Drug Des Devel Ther. 2018; 12: 1239-1254; Avan et al., Chem. Soc. Rev., 2014, 43, 3575-3594; Pathak, et al., Indo American Journal of Pharmaceutical Research, 2015. 8; Kazmierski, W. M., ed., Peptidomimetics Protocols, Human Press (Totowa NJ 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as ∀-amino phosphonic acids and ∀-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. Exemplary retro-inverso targeting peptidomimetics include KLASVT and KFLASVT, wherein the sequences include all D-amino acids. These sequences can be modified, e.g., by biotinylation of the amino terminus and amidation of the carboxy terminus.

AAVs

Viral vectors for use in the present methods and compositions include recombinant retroviruses, adenovirus, adeno-associated virus, alphavirus, and lentivirus, comprising the targeting peptides described herein and optionally a transgene for expression in a target tissue.

A preferred viral vector system useful for delivery of nucleic acids in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). There are numerous alternative AAV variants (over 100 have been cloned), and AAV variants have been identified based on desirable characteristics. In some embodiments, the AAV is AAV1, AAV2, AAV4, AAV5, AAV6, AV6.2, AAV7, AAV8, AAV9, rh.10, rh.39, rh.43 or CSp3; for CNS use, in some embodiments the AAV is AAV1, AAV2, AAV4, AAV5, AAV6, AAV8, or AAV9. As one example, AAV9 has been shown to somewhat efficiently cross the blood-brain barrier. Using the present methods, the AAV capsid can be genetically engineered to increase permeation across the BBB, or into a specific tissue, by insertion of a targeting sequence as described herein into the capsid protein, e.g., into the AAV9 capsid protein VP1 between amino acids 588 and 589.

An exemplary wild type AAV9 capsid protein VP1 (Q6JC40-1) sequence is as follows:

(SEQ ID NO: 85)

```
            10          20          30          40          50
    MAADGYLPDW  LEDNLSEGIR  EWWALKPGAP  QPKANQQHQD  NARGLVLPGY 60          70          80          90         100
    KYLGPGNGLD  KGEPVNAADA  AALEHDKAYD  QQLKAGDNPY  LKYNHADAEF 110         120         130         140         150
    QERLKEDTSF  GGNLGRAVFQ  AKKRLLEPLG  LVEEAAKTAP  GKKRPVEQSP 160         170         180         190         200
    QEPDSSAGIG  KSGAQPAKKR  LNFGQTGDTE  SVPDPQPIGE  PPAAPSGVGS 210         220         230         240         250
    LTMASGGGAP  VADNNEGADG  VGSSSGNWHC  DSQWLGDRVI  TTSTRTWALP 260         270         280         290         300
    TYNNHLYKQI  SNSTSGGSSN  DNAYFGYSTP  WGYFDFNRFH  CHESPRDWQR 310         320         330         340         350
    LINNNWGFRP  KRLNFKLFNI  QVKEVTDNNG  VKTIANNLTS  TVQVFTDSDY 360         370         380         390         400
    QLPYVLGSAH  EGCLPPFPAD  VEMIPQYGYL  TLNDGSQAVG  RSSFYCLEYF
```

```
        410        420        430        440        450
PSQMLRTGNN FQFSYEFENV PFHSSYAHSQ SLDRLMNPLI DQYLYYLSKT 460        470        480        490        500
INGSGQNQQT LKFSVAGPSN MAVQGRNYIP GPSYRQQRVS TTVTQNNNSE 510        520        530        540        550
FAWPGASSWA LNGRNSLMNP GPAMASHKEG EDRFFPLSGS LIFGKQGTGR 560        570        580        590        600
DNVDADKVMI TNEEEIKTTN PVATESYGQV ATNHQSAQAQ AQTGWVQNQG 610        620        630        640        650
ILPGMVWQDR DVYLQGPIWA KIPHTDGNFH PSPLMGGFGM KHPPPQILIK 660        670        680        690        700
NTPVPADPPT AFNKDKLNSF ITQYSTGQVS VEIEWELQKE NSKRWNPEIQ 710        720        730
YTSNYYKSNN VEFAVNTEGV YSEPRPIGTR YLTRNL
```

Thus provided herein are AAV that include one or more of the targeting peptide sequences described herein, e.g., an AAV comprising a capsid protein comprising a targeting sequence described herein, e.g., a capsid protein comprising SEQ ID NO:1 wherein a targeting peptide sequence has been inserted into the sequence, e.g., between amino acids 588 and 589.

In some embodiments, the AAV also includes a transgene sequence (i.e., a heterologous sequence), e.g., a transgene encoding a therapeutic agent, e.g., as described herein or as known in the art, or a reporter protein, e.g., a fluorescent protein, an enzyme that catalyzes a reaction yielding a detectable product, or a cell surface antigen. The transgene is preferably linked to sequences that promote/drive expression of the transgene in the target tissue.

Exemplary transgenes for use as therapeutics include neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), amino acid decorboxylase (AADC), aspartoacylase (ASPA), blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble VEGF receptors, soluble interleukin receptors (e.g., soluble IL-1 receptors and soluble type II IL-1 receptors), soluble gamma/delta T cell receptors, ligand-binding fragments of a soluble receptor, and the like; enzymes, such as α-glucosidase, imiglucarase, β-glucocerebrosidase, and alglucerase; enzyme activators, such as tissue plasminogen activator; chemokines, such as IP-10, monokine induced by interferon-gamma (Mig), Groa/IL-8, RANTES, MIP-1α, MIP-10, MCP-1, PF-4, and the like; angiogenic agents, such as vascular endothelial growth factors (VEGFs), e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other examples of protein of interest include ciliary neurotrophic factor (CNTF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

The transgene can also encode an antibody, e.g., an immune checkpoint inhibitory antibody, e.g., to PD-L1, PD-1, CTLA-4 (Cytotoxic T-Lymphocyte-Associated Protein-4; CD152); LAG-3 (Lymphocyte Activation Gene 3; CD223); TIM-3 (T-cell Immunoglobulin domain and Mucin domain 3; HAVCR2); TIGIT (T-cell Immunoreceptor with Ig and ITIM domains); B7-H3 (CD276); VSIR (V-set immunoregulatory receptor, aka VISTA, B7H5, C10orf54); BTLA 30 (B- and T-Lymphocyte Attenuator, CD272); GARP (Glycoprotein A Repetitions; Predominant; PVRIG (PVR related immunoglobulin domain containing; or VTCN1 (Vset domain containing T cell activation inhibitor 1, aka B7-H4).

Other transgenes can include small or inhibitory nucleic acids that alter/reduce expression of a target gene, e.g., siRNA, shRNA, miRNA, antisense oligos, or long non-coding RNAs that alter gene expression (see, e.g., WO2012087983 and US20140142160), or CRISPR Cas9/cas12a and guide RNAs.

The virus can also include one or more sequences that promote expression of a transgene, e.g., one or more promoter sequences; enhancer sequences, e.g., 5' untranslated region (UTR) or a 3' UTR; a polyadenylation site; and/or insulator sequences. In some embodiments, the promoter is a brain tissue specific promoter, e.g., a neuron-specific or glia-specific promoter. In certain embodiments, the promoter is a promoter of a gene selected to from: neuronal nuclei (NeuN), glial fibrillary acidic protein (GFAP), MeCP2, adenomatous polyposis coli (APC), ionized calcium-binding adapter molecule 1 (Iba-1), synapsin I (SYN), calcium/calmodulin-dependent protein kinase II, tubulin alpha I, neuron-specific enolase and platelet-derived growth factor beta chain. In some embodiments, the promoter is a pan-cell type promoter, e.g., cytomegalovirus (CMV), beta glucuronidase, (GUSB), ubiquitin C (UBC), or rous sarcoma virus (RSV) promoter. The woodchuck hepatitis virus post-transcriptional response element (WPRE) can also be used.

In some embodiments, the AAV also has one or more additional mutations that increase delivery to the target tissue, e.g., the CNS, or that reduce off-tissue targeting, e.g., mutations that decrease liver delivery when CNS, heart, or muscle delivery is intended (e.g., as described in Pulicherla et al. (2011) Mol Ther 19:1070-1078); or the addition of other targeting peptides, e.g., as described in Chen et al. (2008) Nat Med 15:1215-1218 or Xu et al., (2005) Virology 341:203-214 or U.S. Pat. Nos. 9,102,949; 9,585,971; and US20170166926. See also Gray and Samulski (2011) "Vector design and considerations for CNS applications," in Gene Vector Design and Application to Treat Nervous System Disorders ed. Glorioso J., editor. (Washington, DC: Society for Neuroscience;) 1-9, available at sfn.org/~/media/SfN/Documents/Short %20Courses/20110%20Short %20Course %20I/2 011_SC1_Gray.ashx.

Targeting Peptides as Tags/Fusions

The targeting peptides described herein can also be used to increase permeation of other (heterologous) molecules across the BBB, e.g., by conjugation to the molecule, or by expression as part of a fusion protein, e.g., with an antibody or other large biomolecule. These can include genome editing proteins or complexes (e.g., TALEs, ZFNs, Base editors, and CRISPR RNPs comprising a gene editing protein such as Cas9 or Cas12a, fused to a peptide described herein (e.g., at the N terminus, C terminus, or internally) and a guide RNA), in addition to therapeutic agents or reporters as described herein as well as those listed in Table 2. The fusions/complexes do not comprise any other sequences from Ku70, e.g., comprise heterologous non-Ku70 sequences, and are not present in nature.

In some embodiments, targeting sequences used as part of a non-AAV fusion protein do not comprise or consist of VPALR (SEQ ID NO:1) or VSALK (SEQ ID NO:2).

Methods of Use

The methods and compositions described herein can be used to deliver any composition, e.g., a sequence of interest to a tissue, e.g., to the central nervous system (brain), heart, muscle, or dorsal root ganglion or spinal cord (peripheral nervous system). In some embodiments, the methods include delivery to specific brain regions, e.g., cortex, cerebellum, hippocampus, substantia nigra, amygdala. In some embodiments, the methods include delivery to neurons, astrocytes, glial cells, or cardiomyocytes.

In some embodiments, the methods and compositions, e.g., AAVs, are used to deliver a nucleic acid sequence to a subject who has a disease, e.g., a disease of the CNS; see, e.g., U.S. Pat. Nos. 9,102,949; 9,585,971; and US20170166926. In some embodiments, the subject has a condition listed in Table 2; in some embodiments, the vectors are used to deliver a therapeutic agent listed in Table 2 for treating the corresponding disease listed in Table 2. The therapeutic agent can be delivered as a nucleic acid, e.g. via a viral vector, wherein the nucleic acid encodes a therapeutic protein or other nucleic acid such as an antisense oligo, siRNA, shRNA, and so on; or as a fusion protein/complex with a targeting peptide as described herein.

TABLE 2

| Diseases | | |
|---|---|---|
| Examples of diseases | Tissue targeted | Therapeutic agent |
| Parkinson's disease | CNS | GDNF, AADC |
| Alzheimer's disease | CNS | Tau antibody, APP antibody |
| Huntington's disease | CNS | miRNA targeting HTT |
| Amyotrophic lateral sclerosis | CNS | shRNA targeting SOD |
| Multiple sclerosis | CNS | IFN-beta |
| Epilepsy | CNS | Neuropeptide Y |
| Stroke | CNS | IGF-1, osteopontin |
| Brain cancer | CNS | HSV.TK1, PD-1/PD-L1 antibody |
| Spinocerebellar ataxia | CNS | RNAi targeting ataxin |
| Canavan disease | CNS | ASPA |
| Metachromatic leukodystrophy | Nervous systems | ARSA, PSAP |
| Spinal muscular atrophy | Neuromuscular system | SMN1 |
| Friedreich's ataxia | Nervous systems, heart | Frataxin |
| X-linked myotubular myopathy | Neuromuscular system | MTM1 |
| Pompe disease | Lysosome (global including CNS) | GAA |
| Barth syndrome | Heart, muscle | TAZ |
| Duchenne muscular dystrophy | Muscle | dystrophin |
| Wilson's disease | Brain, liver | ATP7B |
| Crigler-Najjar syndrome type 1 | Liver | UGT1A1 |

In some embodiments, the compositions and methods are used to treat brain cancer. Brain cancers include gliomas (e.g., glioblastoma multiforme (GBM)), metastases (e.g., from lung, breast, melanoma, or colon cancer), meningiomas, pituitary adenomas, and acoustic neuromas. The compositions include a targeting peptide linked to an anticancer agent, e.g., a "suicide gene" that induces apoptosis in a target cell (e.g., HSV.TK1, Cytosine Deaminase (CD) from Herpes simplex virus or Escherichia coli, or Escherichia coli purine nucleoside phosphorylase (PNP)/fludarabine; see Krohne et al., Hepatology. 2001 September; 34(3):511-8; Dey and Evans, "Suicide Gene Therapy by Herpes Simplex Virus-1 Thymidine Kinase (HSV-TK)" (2011) DOI: 10.5772/18544) an immune checkpoint inhibitory antibody as known in the art or described herein. For example, an AAV vector comprising a targeting peptide as described herein can be used to deliver the "suicide gene" HSV.TK1 to a brain tumor. HSV.TK1 turns the otherwise "dormant" ganciclovir into a tumor-killing drug. Thus the methods can include systemically, e.g., intravenously, administering an AAV (e.g., AAV9) comprising a targeting peptide as described herein and encoding HSV.TK1, and the pro-drug ganciclovir, to a subject who has been diagnosed with brain cancer.

Pharmaceutical Compositions and Methods of Administration

The methods described herein include the use of pharmaceutical compositions comprising the targeting peptides as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intraarterial, subcutaneous, intraperitoneal intramuscular or injection or infusion administration. Delivery can thus be systemic or localized.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a kit, container, pack, or dispenser together with instructions for administration. For example, the compositions comprising an AAV comprising a targeting peptide as described herein and a nucleic acid encoding HSV.TK1 can be provided in a kit with ganciclovir.

EXAMPLES

The invention is further described in the following examples, which do not limit the scope of the invention described in the claims.

Materials and Methods

The following materials and methods were used in the Examples below.

1. Generation of Capsid Variants

To generate the capsid variant plasmids, DNA fragments that encode the cell-penetrating peptides (Table 3) were synthesized (GenScript), and inserted into the backbone of the AAV9 Rep-cap plasmid (pRC9) between amino acid position 588 and 589 (VP1 amino acid numbering), using CloneEZ seamless cloning technology (GenScript). CPPs BIP1(VPALR, SEQ ID NO:1) and BIP2 (VSALK, SEQ ID NO:2), as well as their derivatives such as TVSALK (SEQ ID NO:4) in AAV.CPP.16 and TVSALFK (SEQ ID NO:8) in AAV.CPP.21, are derived from the Ku70 proteins, of which the sequences are provided as below:

```
Human Ku70    MSGWESYYKTEGDEEAEEEQEENLEASGDYKYSGRDSLIFLVDASKAMFESQSEDELTPF   60

Mouse Ku70    MSEWESYYKTEGEEEEE--EESPDTGGEYKYSGRDSLIFLVDASRAMFESQGEDELTPF   58

Rat Ku70      MSEWESYYKTEGEEEEE--EQSPDTNGEYKYSGRDSLIFLVDASRAMFESQGEDELTPF   58
```

-continued

```
Human Ku70   DMSIQCIQSVYISKIISSDRDLLAVVFYGTEKDKNSVNFKNIYVLQELDNPGAKRILELD   120

Mouse Ku70   DMSIQCIQSVYTSKIISSDRDLLAVVFYGTEKDKNSVNFKNIYVLQDLDNPGAKRVLELD   118

Rat Ku70     DMSIQCIQSVYTSKIISSDRDLLAVVFYGTEKDKNSVNFKSIYVLQDLDNPGAKRVLELD   118

Human Ku70   QFKGQQGQKRFQDMMGHGSDYSLSEVLWVCANLFSDVQFKMSHKRIMLFTNEDNPHGNDS   180

Mouse Ku70   QFKGQQGKKHFRDTVGHGSDYSLSEVLWVCANLFSDVQLKMSHKRIMLFTNEDDPHGRDS   178

Rat Ku70     RFKGQQGKKHFRDTIGHGSDYSLSEVLWVCANLFSDVQFKMSHKRIMLFTNEDDPHGNDS   178

Human Ku70   AKASRARTKAGDLRDTGIFLDLMHLKKPGGFDISLFYRDIISIAEDEDLRVHFEESSKLE   240

Mouse Ku70   AKASRARTKASDLRDTGIFLDLMHLKKPGGFDVSVFYRDIITTAEDEDLGVHFEESSKLE   238

Rat Ku70     AKASRARTKASDLRDTGIFLDLMHLKKRGGFDVSLFYRDIISIAEDEDLGVHFEESSKLE   238

Human Ku70   DLLRKVRAKETRKRALSRLKLKLNKDIVISVGIYNLVQKALKPPPIKLYRETNEPVKTKT   300

Mouse Ku70   DLLRKVRAKETKKRVLSRLKFKLGEDVVLMVGIYNLVQKANKPFPVRLYRETNEPVKTKT   298

Rat Ku70     DLLRKVRAKETKKRVLSRLKFKLGKDVALMVGVYNLVQKANKPFPVRLYRETNEPVKTKT   298

Human Ku70   RTFNTSTGGLLLPSDTKRSQIYGSRQIILEKEETEELKRFDDPGLMLMGFKPLVLLKKHH   360

Mouse Ku70   RTFNVNTGSLLLPSDTKRSLTYGTRQIVLEKEETEELKRFDEPGLILMGFKPTVMLKKQH   358

Rat Ku70     RTFNVNTGSLLLPSDTKRSLTFGTRQIVLEKEETEELKRFDEPGLILMGFKPMVMLKNHH   358

Human Ku70   YLRPSLFVYPEESLVIGSSTLFSALLIKCLEKEVAALCRYTPRRNIPPYFVALVPQEEEL   420

Mouse Ku70   YLRPSLEVYPEESLVSGSSTLFSALLTKCVEKEVIAVCRYTPRKNVSPYFVALVPQEEEL   418

Rat Ku70     YLRPSLFLYPEESLVNGSSTLFSALLTKCVEKEVIAVCRYTARKNVSPYFVALVPQEEEL   418

Human Ku70   DDQKIQVTPPGFQLVFLPFADDKRKMPFTEKIMATPEQVGKMKAIVEKLRFTYRSDSFEN   480

Mouse Ku70   DDQNIQVTPGGFQLVFLPYADDKRKVPFTEKVTANQEQIDKMKAIVQKLRFTYRSDSFEN   478

Rat Ku70     DDQNIQVTPAGFQLVFLPYADDKRKVPFTEKVMANPEQIDKMKAIVQKLRFTYRSDSFEN   478

Human Ku70   PVLQQHFRNLEALALDLMEPEQAVDLTLPKVEAMNKRLGSLVDEFKELVYPPDYNPEGKV   540

Mouse Ku70   PVLQQHFRNLEALALDMMESEQVVDLTLPKVEAIKKRLGSLADEFKELVYPPGYNPEGKV   538

Rat Ku70     PVLQQHFRNLEALALDMMESEQVVDLTLPKVEAIKKRLGSLADEFKELVYPPGYNPEGKI   538

Human Ku70   TKRKHDNEGSGSKRPKVEYSEEELKTHISKGTLGKFTVPMLKEACRAYGLKSGLKKQELL   600

Mouse Ku70   AKRKQDDEGSTSKKPKVELSEEEELKAHFRKGTLGKLTVPTLKDICKAHGLKSGPKKQELL   598

Rat Ku70     AKRKADNEGSASKKPKVELSEEEELKDLFAKGTLGKLTVPALRDICKAYGLKSGPKKQELL   598

Human Ku70   EALTKHFQD-   609   (SEQ ID NO: 86)

Mouse Ku70   DALIRHLEKN   608   (SEQ ID NO: 87)

Rat Ku70     EALSRHLEKN   608   (SEQ ID NO: 88)
```

In addition, VP1 protein sequences for AAV9, AAV.CPP.16 and AAV.CPP.21 are provided as below:

```
AAV9         MAADGYLPDWLEDNLSEGIREWWALKPGAPQPKANQQHQDNARGLVLPGYKYLGPGNGLD   60

AAV.CPP16    MAADGYLPDWLEDNLSEGIREWWALKPGAPQPKANQQHQDNARGLVLPGYKYLGPGNGLD   60

AAV.CPP21    MAADGYLPDWLEDNLSEGIREWWALKPGAPQPKANQQHQDNARGLVLPGYKYLGPGNGLD   60

AAV9         KGEPVNAADAAALEHDKAYDQQLKAGDNPYLKYNHADAEFQERLKEDTSFGGNLGRAVEQ   120

AAV.CPP16    KGEPVNAADAAALEHDKAYDQQLKAGDNPYLKYNHADAEFQERLKEDTSFGGNLGRAVFQ   120

AAV.CPP21    KGEPVNAADAAALEHDKAYDQQLKAGDNPYLKYNHADAEFQERLKEDTSFGGNLGRAVEQ   120

AAV9         AKKRLLEPLGLVEEAAKTAPGKKRPVEQSPQEPDSSAGIGKSGAQPAKKRLNFGQTGDTE   180
```

```
                -continued
AAV.CPP16   AKKRLLEPLGLVEEAAKTAPGKKRPVEQSPQEPDSSAGIGKSGAQPAKKRLNFGQTGDTE 180

AAV.CPP21   AKKRLLEPLGLVEEAAKTAPGKKRPVEQSPQEPDSSAGIGKSGAQPAKKRLNFGQTGDTE 180

AAV9        SVPDPQPIGEPPAAPSGVGSLTMASGGGAPVADNNEGADGVGSSSGNWHCDSQWLGDRVI 240

AAV.CPP16   SVPDPQPIGEPPAAPSGVGSLTMASGGGAPVADNNEGADGVGSSSGNWHCDSQWLGDRVI 240

AAV.CPP21   SVPDPQPIGEPPAAPSGVGSLTMASGGGAPVADNNEGADGVGSSSGNWHCDSQWLGDRVI 240

AAV9        TTSTRTWALPTYNNHLYKQISNSTSGGSSNDNAYFGYSTPWGYFDFNRFHCHFSPRDWQR 300

AAV.CPP16   TTSTRTWALPTYNNHLYKQISNSTSGGSSNDNAYFGYSTPWGYFDFNRFHCHFSPRDWQR 300

AAV.CPP21   TTSTRTWALPTYNNHLYKQISNSTSGGSSNDNAYFGYSTPWGYFDFNRFHCHFSPRDWQR 300

AAV9        LINNNWGFRPKRLNFKLFNIQVKEVTDNNGVKTIANNLTSTVQVFTDSDYQLPYVLGSAH 360

AAV.CPP16   LINNNWGFRPKRLNFKLFNIQVKEVTDNNGVKTIANNLTSTVQVFTDSDYQLPYVLGSAH 360

AAV.CPP21   LINNNWGFRPKRLNFKLFNIQVKEVTDNNGVKTIANNLTSTVQVFTDSDYQLPYVLGSAH 360

AAV9        EGCLPPFPADVFMIPQYGYLTLNDGSQAVGRSSFYCLEYFPSQMLRTGNNFQFSYEFENV 420

AAV.CPP16   EGCLPPFPADVFMIPQYGYLTLNDGSQAVGRSSFYCLEYFPSQMLRTGNNFQFSYEFENV 420

AAV.CPP21   EGCLPPFPADVFMIPQYGYLTLNDGSQAVGRSSFYCLEYFPSQMLRTGNNFQFSYEFENV 420

AAV9        PFHSSYAHSQSLDRLMNPLIDQYLYYLSKTINGSGQNQQTLKFSVAGPSNMAVQGRNYIP 480

AAV.CPP16   PFHSSYAHSQSLDRLMNPLIDQYLYYLSKTINGSGQNQQTLKFSVAGPSNMAVQGRNYIP 480

AAV.CPP21   PFHSSYAHSQSLDRLMNPLIDQYLYYLSKTINGSGQNQQTLKFSVAGPSNMAVQGRNYIP 480

AAV9        GPSYRQQRVSTTVTQNNNSEFAWPGASSWALNGRNSLMNPGPAMASHKEGEDRFFPLSGS 540

AAV.CPP16   GPSYRQQRVSTTVTQNNNSEFAWPGASSWALNGRNSLMNPGPAMASHKEGEDRFFPLSGS 540

AAV.CPP21   GPSYRQQRVSTTVTQNNNSEFAWPGASSWALNGRNSLMNPGPAMASHKEGEDRFFPLSGS 540

AAV9        LIFGKQGTGRDNVDADKVMITNEEEIKTTNPVATESYGQVATNHQSAQ-------AQAQT 593

AAV.CPP16   LIFGKQGTGRDNVDADKVMITNEEEIKTTNPVATESYGQVATNHQSAQTVSAL-KAQAQT 599

AAV.CPP21   LIFGKQGTGRDNVDADKVMITNEEEIKTTNPVATESYGQVATNHQSAQTVSALFKAQAQT 600

AAV9        GWVQNQGILPGMVWQDRDVYLQGPIWAKIPHTDGNFHPSPLMGGFGMKHPPPQILIKNTP 653

AAV.CPP16   GWVQNQGILPGMVWQDRDVYLQGPIWAKIPHTDGNFHPSPLMGGFGMKHPPPQILIKNTP 659

AAV.CPP21   GWVQNQGILPGMVWQDRDVYLQGPIWAKIPHTDGNFHPSPLMGGFGMKHPPPQILIKNTP 660

AAV9        VPADPPTAFNKDKLNSFITQYSTGQVSVEIEWELQKENSKRWNPEIQYTSNYYKSNNVEF 713

AAV.CPP16   VPADPPTAFNKDKLNSFITQYSTGQVSVEIEWELQKENSKRWNPEIQYTSNYYKSNNVEF 719

AAV.CPP21   VPADPPTAFNKDKLNSFITQYSTGQVSVEIEWELQKENSKRWNPEIQYTSNYYKSNNVEF 720

AAV9        AVNTEGVYSEPRPIGTRYLTRNL 736  (SEQ ID NO: 85)

AAV.CPP16   AVNTEGVYSEPRPIGTRYLTRNL 742  (SEQ ID NO: 89)

AAV.CPP21   AVNTEGVYSEPRPIGTRYLTRNL 743  (SEQ ID NO: 90)
```

2. Recombinant AAV Production

Recombinant AAVs were packaged using standard three-plasmid co-transfection protocol (pRC plasmid, pHelper plasmid and pAAV plasmid). pRC9 (or its variant), pHelper and pAAV carrying a transgene (e.g. nucleus-directed RFP H2B-mCherry driven by an ubiquitous EF1a promoter) were co-transfected into HEK 293T cells using polyethylenimine (PEI, Polysciences). rAAVs vectors were collected from serum-free medium 72 h and 120 h post transfection and from cell at 120 h post transfection. AAV particles in the medium were concentrated using a PEG-precipitation method with 8% PEG-8000 (wt/vol). Cell pellets containing viral particles were resuspended and lysed through sonication. Combined viral vectors from PEG-precipitation and cell lysates were treated with DNase and RNase at 37° C. for 30 mins and then purified by iodixanol gradient (15%, 25%, 40% and 60%) with ultracentrifugation(VTi 50 rotor, 40,000 r.p.m, 18° C., 1 h). rAAVs were then concentrated using Millipore Amicon filter unit (UFC910008, 100K MWCO) and formulated in Dulbecco's phosphate buffered saline (PBS) containing 0.001% Pluronic F68 (Gibco).

3. AAV Titering

Virus titer was determined by measuring DNase-resistant genome copies using quantitative PCR. pAAV-CAG-GFP was digested with PVUII(NEB) to generate free ends for the plasmid ITRs, and was used for generating a standard curve. Virus samples were incubated with DNase I to eliminate contaminating DNA, followed by sodium hydroxide treatment to dissolve the viral capsid and to release the viral genome. Quantitative PCR was performed using an ITR Forward primer 5'-GGAACCCCTAGTGATGGAGTT (SEQ ID NO:91) and an ITR Reverse primer 5'-CGGCCTCAGTGAGCGA (SEQ ID NO:92). Vector titers were normalized to the rAAV-2 reference standard materials (RSMs, ATCC, cat No:VR-1616, Manassas, VA).

4. Administration of AAV in Mice

For intravenous administration, AAV diluted in sterile saline (0.2 ml) was administered through tail vein injection in adult mice (over 6 weeks of age). Animals then survived for three weeks before being euthanized for tissue harvesting. For intracerebral injection, AAV diluted in PBS (10 μl) was injected using a Hamilton syringe with coordinates from bregma: 1.0 mm right, 0.3 backward, 2.6 mm deep. All animal studies were performed in an AAALAC-accredited facility with IACUC approval.

5. Mouse Tissue Processing

Anesthetized animals were transcardially perfused with cold phosphate buffered saline (PBS) followed by 4% paraformaldehyde (PFA). Tissues were post-fixed in 4% PFA overnight, and then immersed in 30% sucrose solutions for two days prior to embedding and snap-freezing in OCT. Typically, 80 μm thick brain sections were cut for imaging of native fluorescence, 40 μm thick brain sections for IHC.

6. In Vitro Human BBB Spheroid Model

Hot 1% agarose (w/v, 50 μl) was added in a 96-well plate to cool/solidify. Primary human astrocytes (Lonza Bioscience), human brain microvascular pericytes (HBVP, Scien-Cell Research Laboratories) and human cerebral microvascular endothelial cells (hCMEC/D3; Cedarlane) were then seeded onto the agarose gel in a 1:1:1 ratio (1500 cells of each type). Cells were cultured at 37° C. in a 5% C02 incubator for 48-72 hours to allow for spontaneous assembly of multicellular BBB spheroids. A multicellular barrier was reported to form at the periphery of the spheroid, mimicking the BBB. AAVs-H2B-mCherry were added to the culture medium, and 4 days later all spheroids were fixed using 4% PFA, transferred into a Nunc Lab-Tek II thin-glass 8-well chambered coverglass (Thermo Scientific), and imaged using a Zeiss LSM710 confocal microscope. The intensity of RFP signal inside the spheroids was examined and used as a "read-out".

7. AAV Administration in Non-Human Primate (NHP)

All NHP studies were performed by a CRO in an AAALAC-accredited facility with IACUC approval. Cynomolgus monkeys were pre-screened for little or no pre-existing neutralizing antibody against AAV9 (titer of <1:5). AAV diluted in PBS/0.001% F68 was injected intravenously (via cephalic vein or femoral vein) using a peristaltic pump. 3 weeks later, animals were subject to transcardial perfusion with PBS, followed by 4% PFA. Tissues were then collected and processed for paraffin embedding and sectioning.

8. Immunohistochemistry

Floating staining was performed for mouse tissue sections with primary antibodies diluted in PBS containing 10% donkey serum and 2% Triton X-100. Primary antibodies used include: chicken anti-GFP (1:1000); rabbit anti-RFP (1:1000); mouse anti-NeuN (1:500); rat anti-GFAP(1:500); Goat anti-GFAP(1:500); mouse anti-CD31(1:500). Secondary antibodies conjugated to fluorophores of Alexa Fluor 488, Alexa Fluor 555 or Alexa Fluor 647 were applied against the primary antibody's host species at a dilution of 1:200.

For paraffin sections of NHP tissue, DAB staining was performed to visualize cells transduced by AAV-AADC. Rabbit anti-AADC antibody (1:500, Millipore) was used as primary antibody.

9. AAV Binding Assay

HEK293T cells were cultured at 37° C. in a 5% C02 incubator. One day after seeding of HEK293T cells in a 24-well plate at a density of 250,000 cells per well, a cDNA plasmid of LY6A was transiently transfected into the cells using a transfection mixture of 200 μl DMEM (31053028; Gibco), 1 ug DNA plasmid and 3 ug of PEI. 48 hours post transfection, cells were placed on ice to chill down for 10 mins. The medium was then changed with 500 μl ice-cold serum-free DMEM medium containing rAAVs-mCherry at MOI of 10000. After incubating on ice for one hour, cells with presumably AAVs bound to their surface were washed with cold PBS for three times and were then subject to genomic DNA isolation. Cell-binding viral particles were quantified by using qPCR with primers specific to mCherry and normalized to HEK293T genomes using human GCG as reference.

10. Mouse Model of Glioblastoma

All experiments were performed in compliance with protocols approved by the Animal Care and Use Committees (IACUC) at the Brigham and Women's Hospital and Harvard Medical School. Syngeneic immuno-competent C57BL/6 female mice weighing 20+/−1 g (Envigo) were used. GL261-Luc (100,000 mouse glioblastoma cells) resuspended in 2 μL phosphate buffered saline (PBS) was injected intracranially using 10 μl syringe with a 26-gauge needle (80075; Hamilton). A stereotactic frame was used to locate the implantation site (coordinates from bregma in mm: 2 right, 0.5 forward, at a depth of 3.5 into cortex). 7 days later, 200 μl AAV-HSV-TK1 (1E+12 viral genomes, IV) was administered once and ganciclovir (50 mg/kg) was administered daily for 10 days.

Example 1. Modification of AAV9 Capsid

Figure 1A:
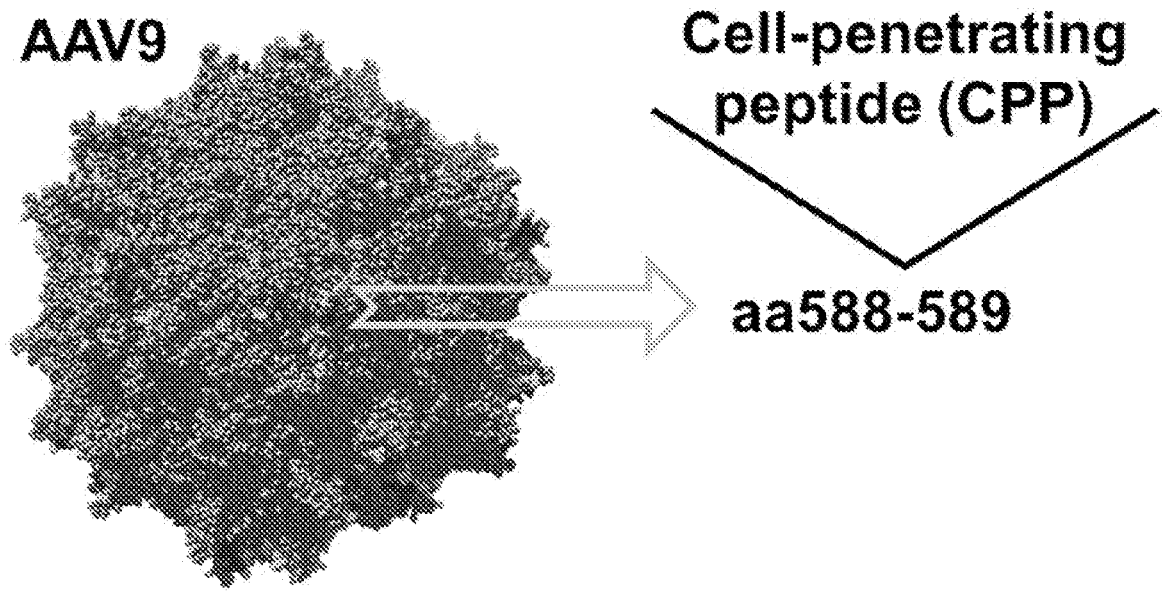
FIGS. 1A-1B depict an exemplary strategy of engineering AAV9 by inserting cell-penetrating peptides (CPPs) into its capsid.
Figure 1B:
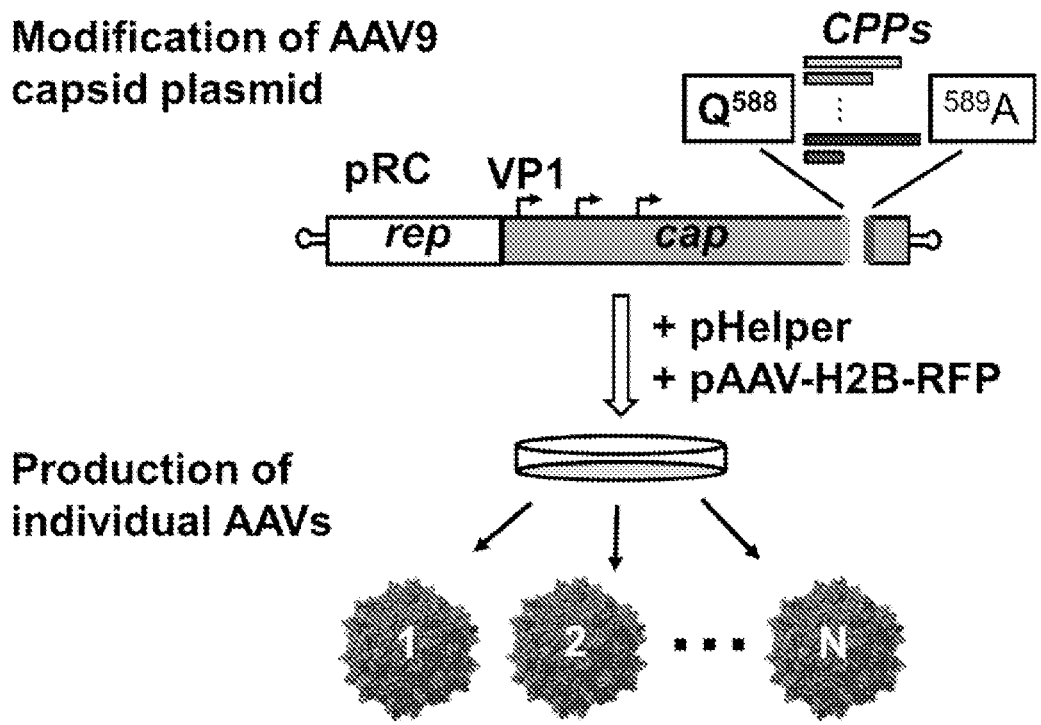

To identify peptide sequences that would enhance permeation of a biomolecule or virus across the blood brain barrier an AAV peptide display technique was used. Individual cell-penetrating peptides, as listed in Table 3, were inserted into the AAV9 capsid between amino acids 588 and 589 (VP1 numbering) as illustrated in FIG. 1A. The insertion was carried out by modifying the RC plasmid, one of the three plasmids co-transfected for AAV packaging; FIG. 1B shows an exemplary schematic of the experiments. Individual AAV variants were produced and screened separately. See Materials and Methods #1-3 for more details.

TABLE 3

|  | AAV | Name of CPP insert | Amino acid sequence of CPP | # | No. of CPP residues | Viral titer |
| --- | --- | --- | --- | --- | --- | --- |
| Initial screening | AAV9 | N/A | N/A |  | N/A | Normal |
|  | AAV.CPP.1 | SynB1 | RGGRLSYSRRRFSTSTGR | 93 | 18 | Low |
|  | AAV.CPP.2 | L-2 | HARIKPTFRRLKWKYKGKFW | 94 | 20 | Low |

TABLE 3-continued

|  | AAV | Name of CPP insert | Amino acid sequence of CPP | # | No. of CPP residues | Viral titer |
|---|---|---|---|---|---|---|
|  | AAV.CPP.3 | PreS2-TLM | PLSSIFSRIGDP | 95 | 12 | Low |
|  | AAV.CPP.4 | Transportan 10 | AGYLLGKINLKALAA LAKKIL | 96 | 21 | Low |
|  | AAV.CPP.5 | SAP | VRLPPPVRLPPPVRLPPP | 97 | 18 | Normal |
|  | AAV.CPP.6 | SAP(E) | VELPPPVELPPPVELPPP | 98 | 18 | Normal |
|  | AAV.CPP.7 | SVM3 | KGTYKKKLMRIPLKGT | 99 | 16 | Low |
|  | AAV.CPP.8 | (PPR)3 | PPRPPRPPR | 100 | 9 | Normal |
|  | AAV.CPP.9 | (PPR)5 | PPRPPRPPRPPRPPR | 101 | 15 | Low |
|  | AAV.CPP.10 | Polyarginine | RRRRRRRR | 102 | 8 | Low |
|  | AAV.CPP.11 | Bip1 | VPALR | 1 | 5 | Normal |
|  | AAV.CPP.12 | Bip2 | VSALK | 2 | 5 | Normal |
|  | AAV.CPP.13 | DPV15 | LRRERQSRLRRERQSR | 103 | 16 | NA |
|  | AAV.CPP.14 | HIV-1 Tat | RKKRRQRRR | 104 | 9 | NA |
| Follow-up screening | AAV.CPP.15 | Bip1.1 | TVPALR (Rat) | 3 | 6 | Normal |
|  | AAV.CPP.16 | Bip2.1 | TVSALK (Syn) | 4 | 6 | Normal |
|  | AAV.CPP.17 | Bip2.2 | FTVSALK (Syn) | 5 | 7 | Normal |
|  | AAV.CPP.18 | Bip2.3 | LTVSALK (Syn) | 6 | 7 | Normal |
|  | AAV.CPP.19 | Bip2.4 | KFTVSALK (Syn) | 72 | 8 | Normal |
|  | AAV.CPP.20 | Bip2.5 | TFVSALK (Syn) | 7 | 7 | Normal |
|  | AAV.CPP.21 | Bip2.6 | TVSALFK (Syn) | 8 | 7 | Normal |
|  | AAV.CPP.22 | Bip2.6Rat | TVPALFR (Rat) | 9 | 7 | Normal |

Example 2. First Round of In Vivo Screening

Figure 2A:
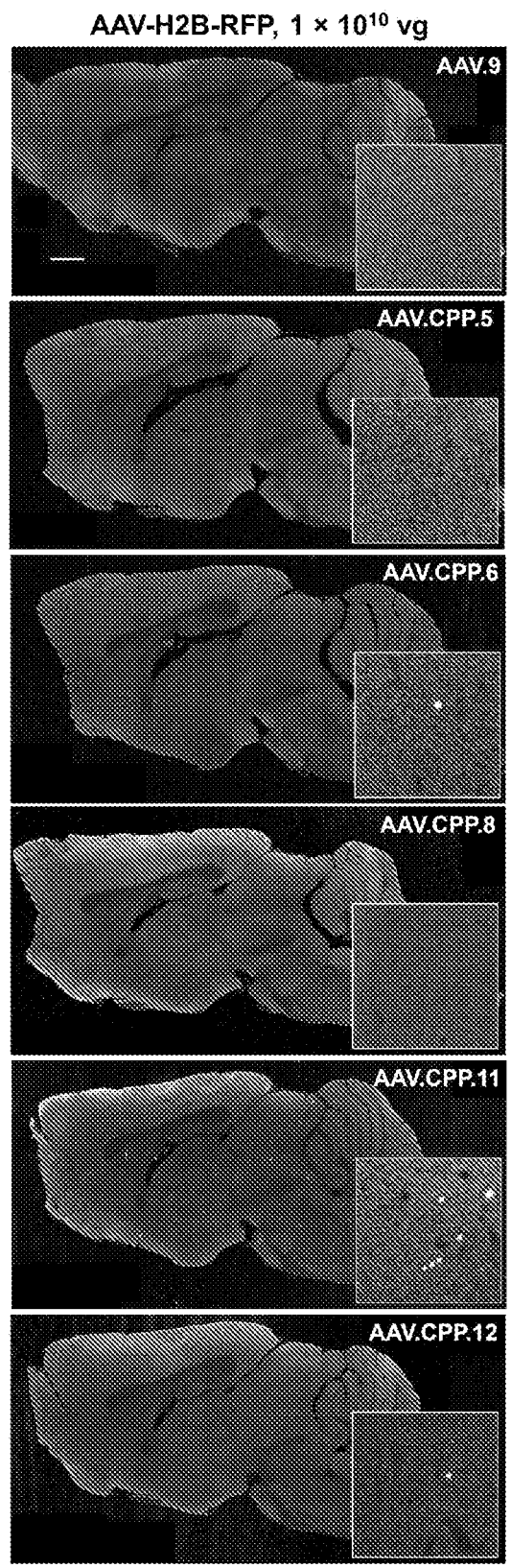
FIGS. 2A-2B depict representative images of mouse brain sections and their quantitative analysis after intravenous administration of low-dose candidate AAVs. Mice with mixed genetic background are used. Candidate AAVs differs in their inserted CPPs (see Table 3), but all express nuclear red fluorescent protein (RFP) as reporter. Candidate AAVs with low production yields are excluded for further screening. The dose of AAV is $1\times10^{10}$ vg (viral genome) per animal. Each white dot in FIG. 2A represents a RFP-labeled cell.
Figure 2B:
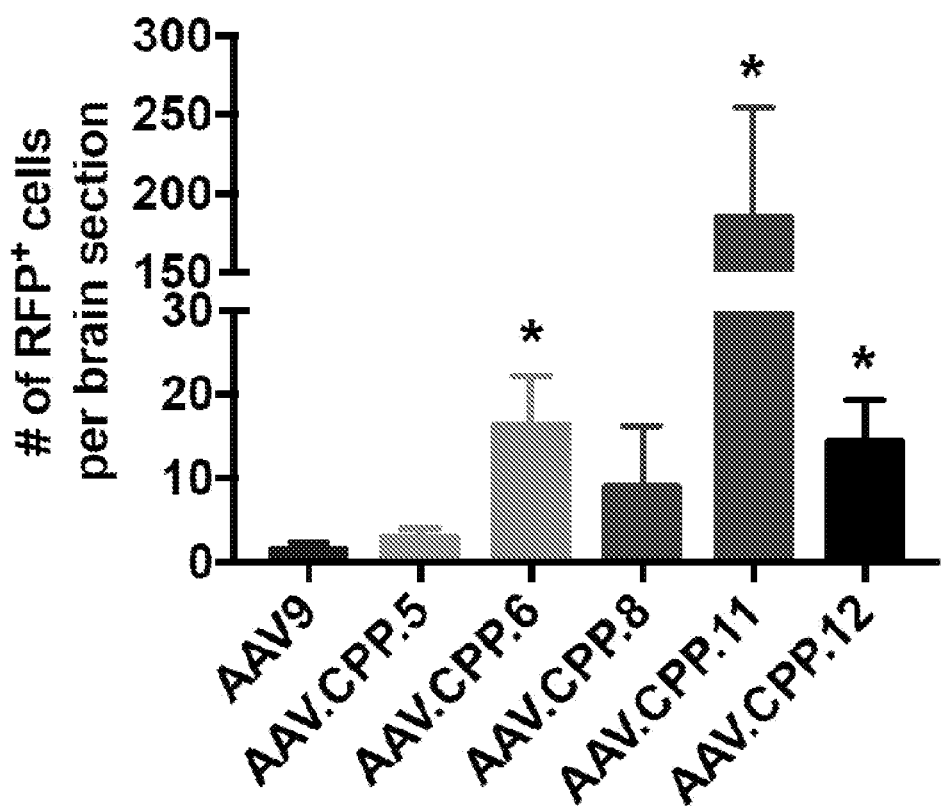
Figure 2C:
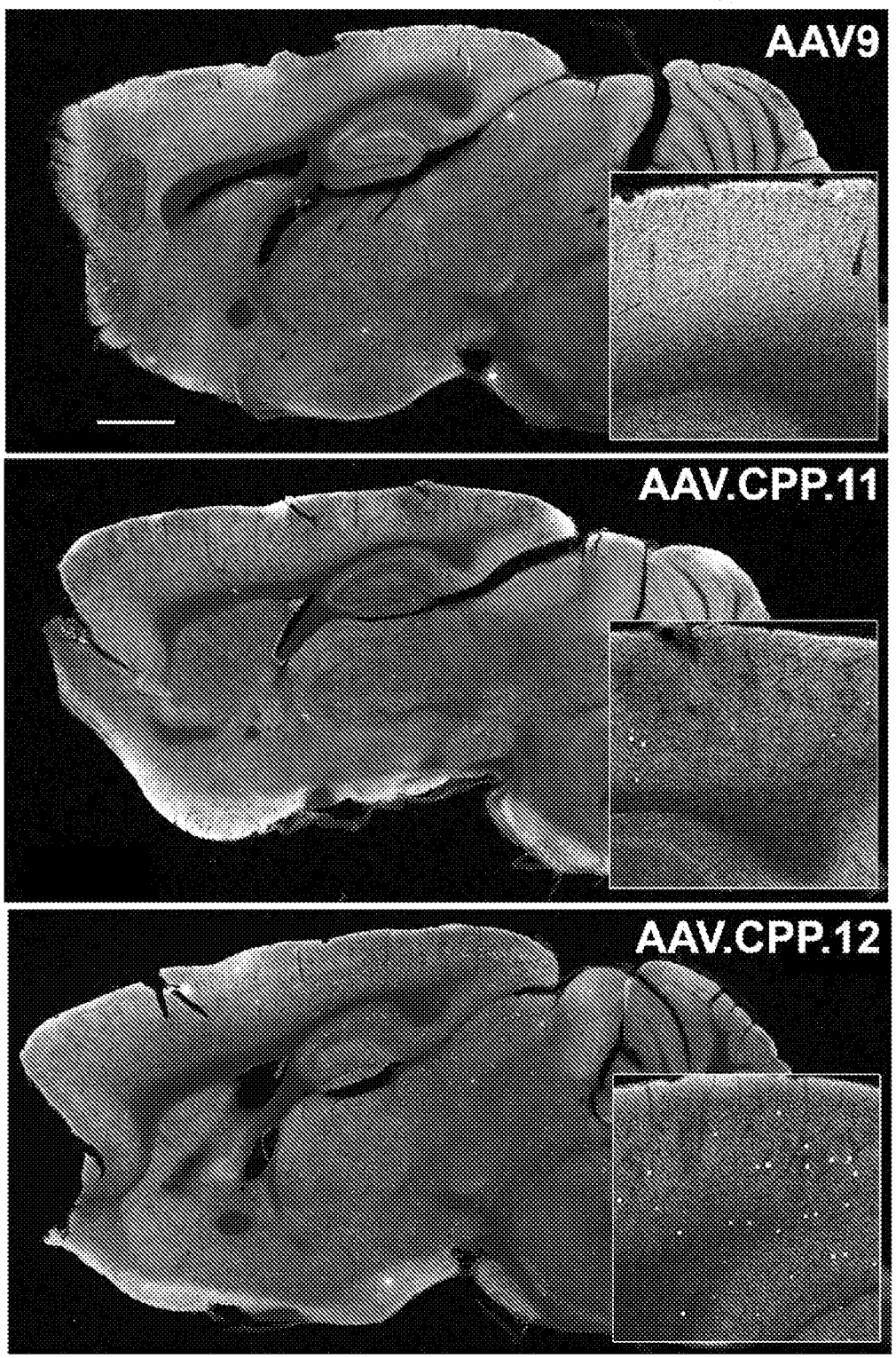
FIGS. 2C-2D depict representative images of mouse brain sections and their quantitative analysis after intravenous administration of AAV.CPP.11 and AAV.CPP.12 in a repeat experiment. AAV.CPP.11 and AAV.CPP.12 contain CPPs BIP1 and BIP2 respectively (see Table 3). The doses of the AAVs are increased to $1\times10^{11}$ vg per animal. Candidate AAVs express nuclear red fluorescent protein (RFP) as reporter. Each white dot in FIG. 2C represents a RFP-labeled cell.
Figure 2D:
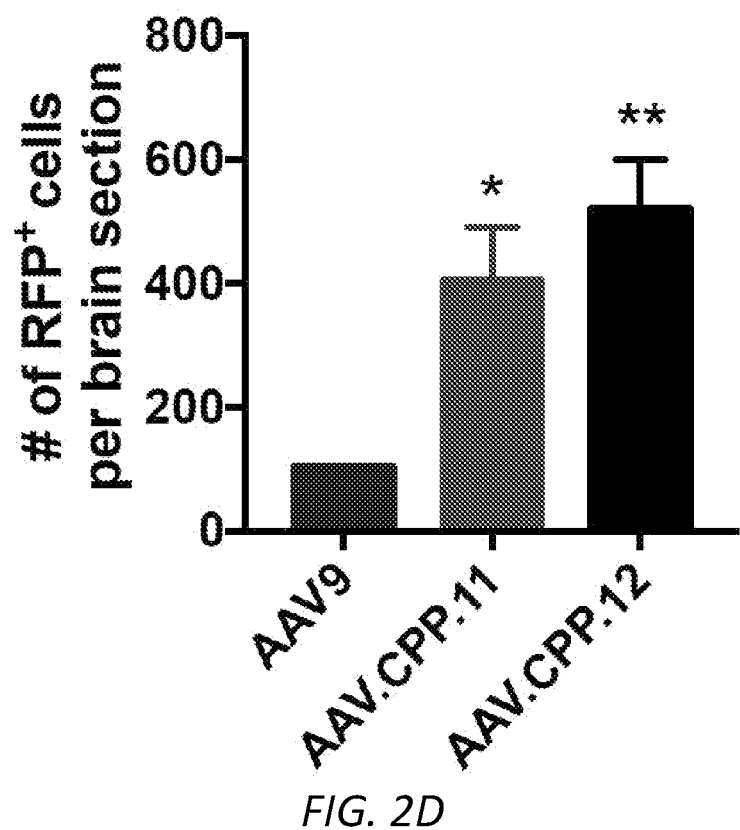

AAVs expressing nuclear RFP (H2B-RFP) were injected intravenously in adult mice with mixed C57B3L/6 and BALB/c genetic background. 3 weeks later, brain tissues were harvested and sectioned to reveal RFP-labelled cells (white dots in FIGS. 2A and 2C, quantified in FIGS. 2B and 2D, respectively). CPPs BIP1 and BTP2 were inserted into the capsids of AAV.CPP.11 and AAV.CPP.12, respectively. See Materials and Methods #4-5 for more details.

Example 3. Optimization of Modified AAV9 Capsids

Figure 3B:
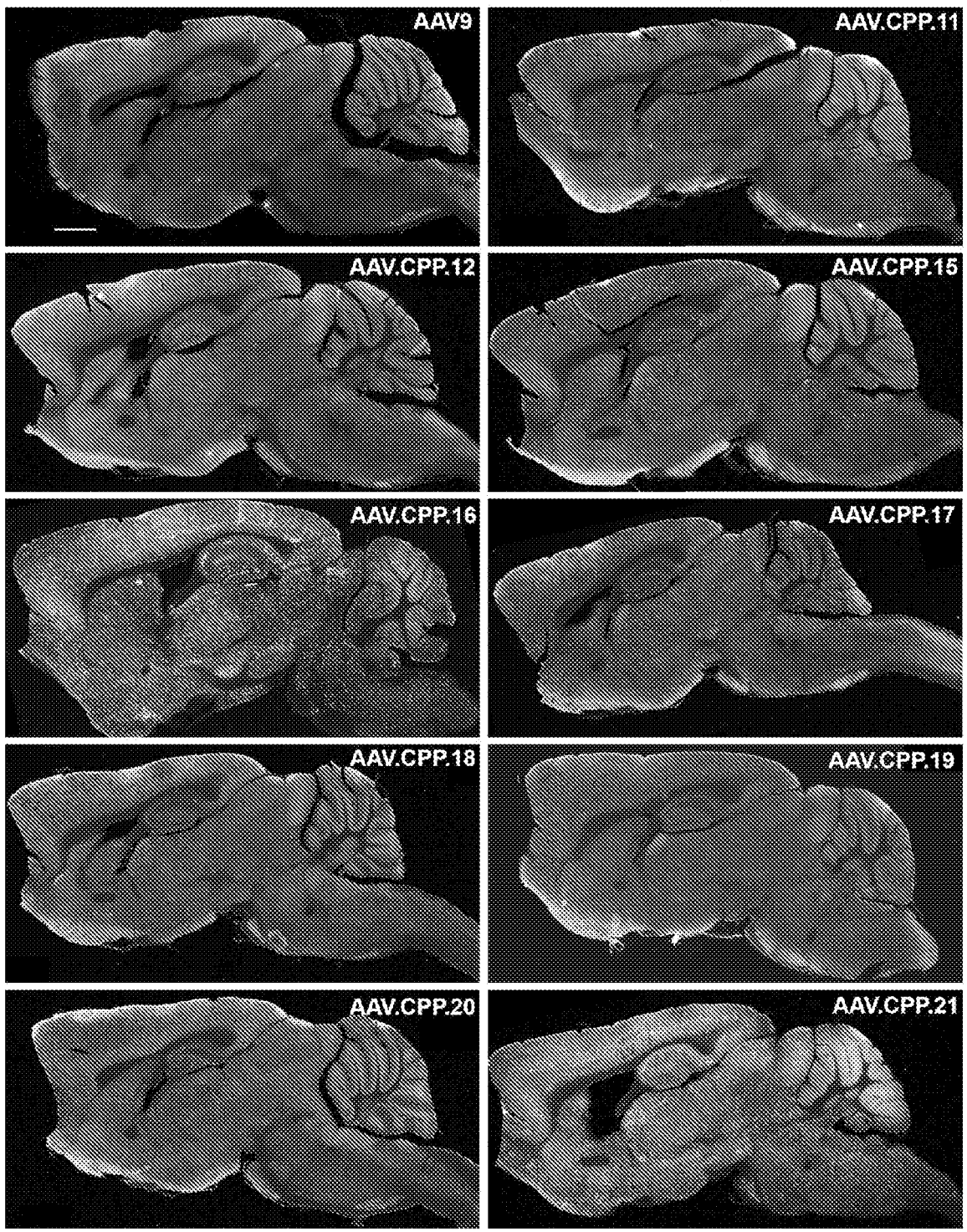
FIGS. 3B-3C depict representative images of mouse brain sections and their quantitative analysis after intravenous administration of more candidate AAVs. All candidate AAVs express nuclear red fluorescent protein (RFP) as reporter. The dose of AAV is $1\times10^{11}$ vg per animal. Each white dot in FIG. 3B represents a RFP-labeled cell. AAV.CPP.16 and AAV.CPP.21 were identified as top hits with their robust and widespread brain transduction.
Figure 3C:
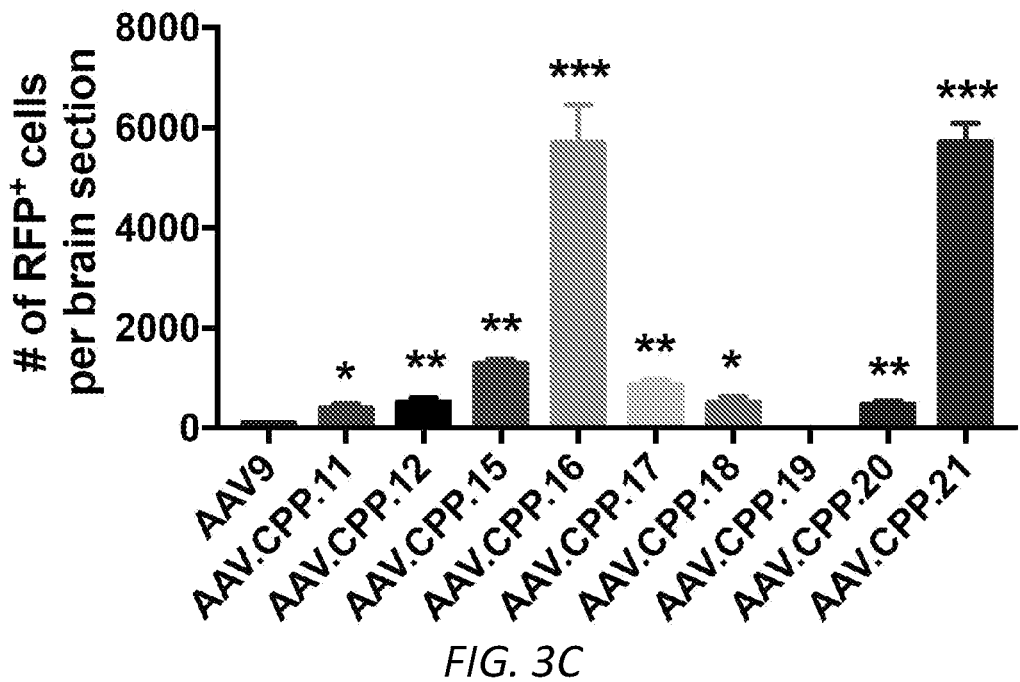
Figure 3D:
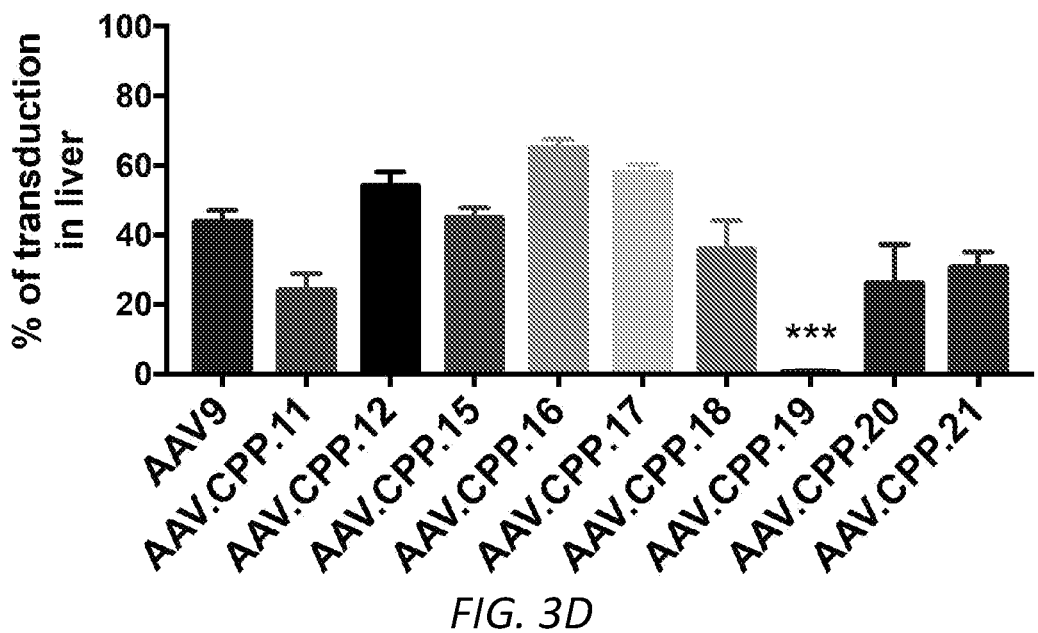
FIG. 3D depicts quantitative analysis of transduction efficiency in the liver after intravenous administration of candidate AAVs. Percentage of transduced liver cells is presented. The dose of AAV is $1\times10^{11}$ vg per animal. *** P<0.001, vs. AAV9, ANOVA.

AAV.CPP.11 and AAV.CPP.12 were further engineered by optimizing the BIP targeting sequences. BIP inserts were derived from the protein Ku70 (See FIG. 3A and Material/Methods #1 for full sequence). The BIP sequence VSALK, which is of "synthetic" origin, was chosen as a study focus to minimize potential species specificity of engineered AAV vectors. AAVs were produced and tested separately for brain transduction efficiency as compared with AAV9 (see FIGS. 3B-C). Percentages of cell transduction in the mouse liver 3 weeks after IV injection of some AAV variants delivering the reporter gene RFP are shown in FIG. 3D. See Materials and Methods #1-5 for more details.

Example 4. In Vitro Model—BBB Permeation Screening

Figure 4A:
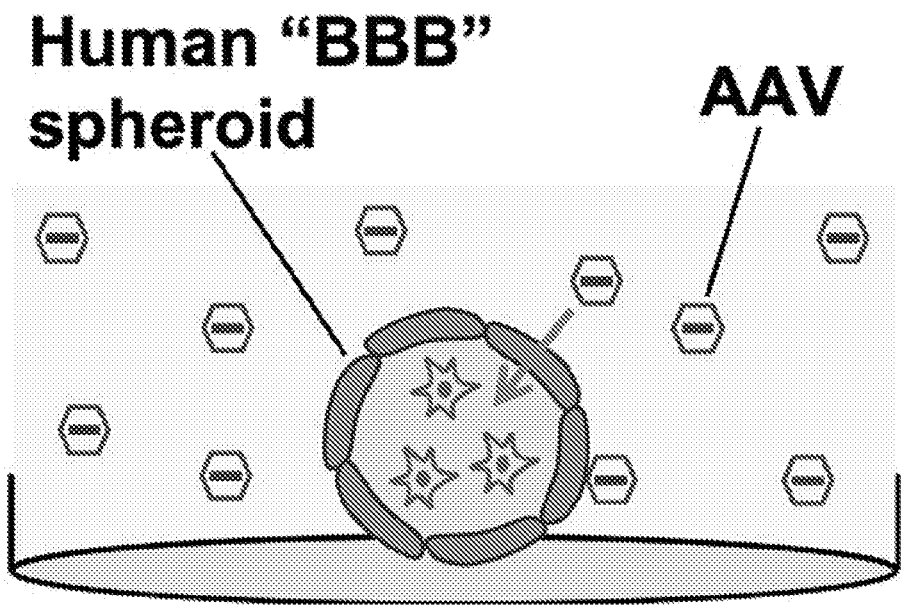
FIGS. 4A-4E depict screening of selected candidate AAVs in an in vitro spheroid model of human blood-brain barrier.
Figure 4B:
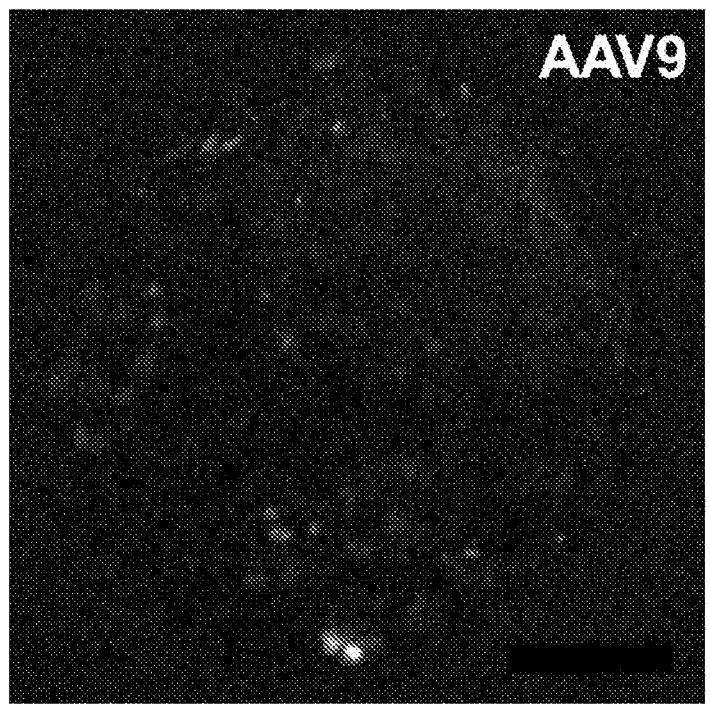
Figure 4C:
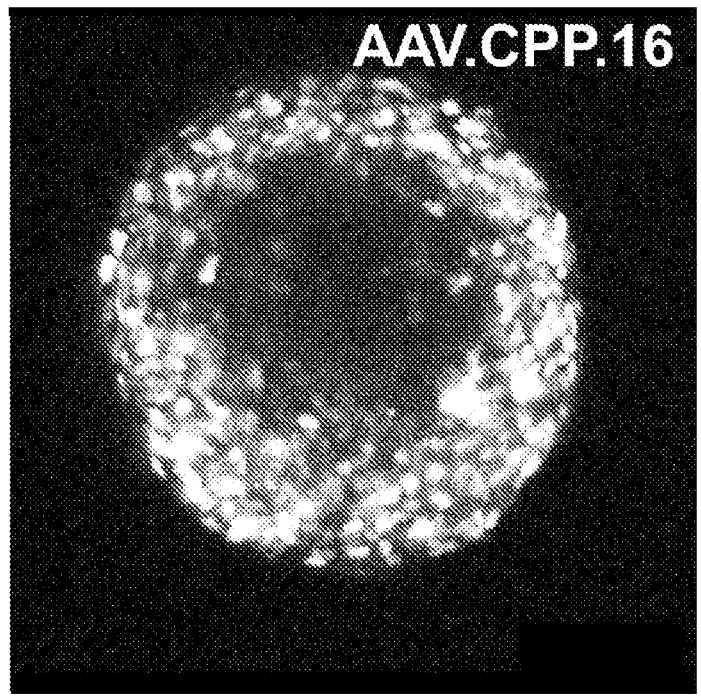
Figure 4D:
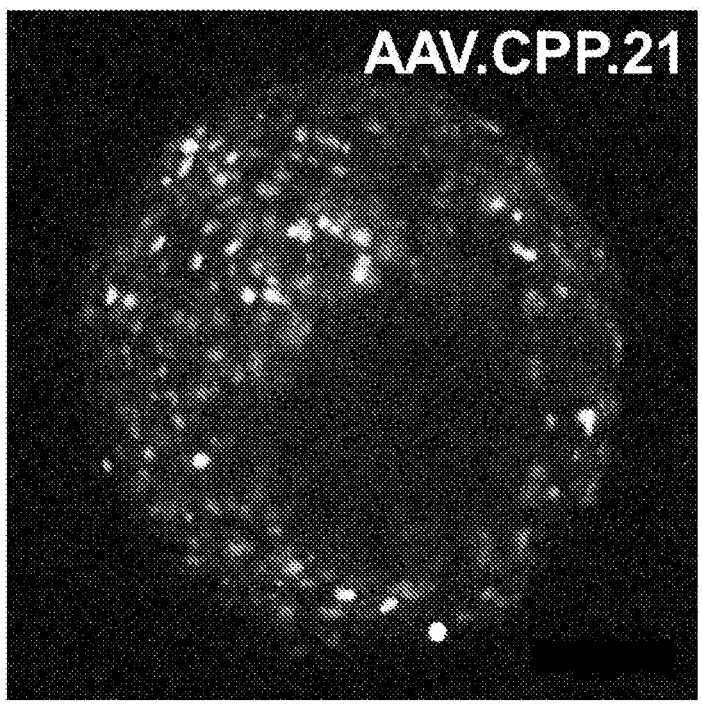
Figure 4E:
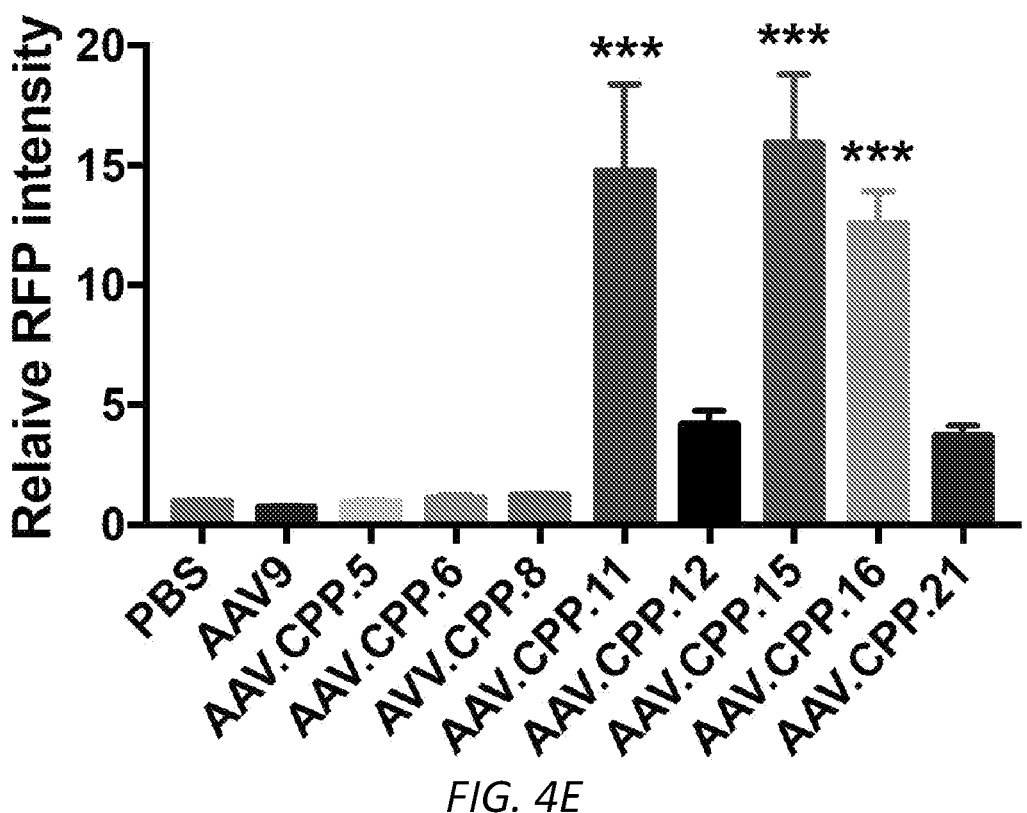

Some of the AAV variants were screened for the ability to cross the human BBB using an in vitro spheroid BBB model. The spheroid contains human microvascular endothelial cells, which form a barrier at the surface, and human pericytes and astrocytes. AAVs carrying nuclear RFP as reporter were assessed for their ability to penetrate from the surrounding medium into the inside of the spheroid and to transduce the cells inside. FIG. 4A shows an experimental schematic. FIGS. 4B-D show results for wt AAV9, AAV.CPP.16, and AAV.CPP.21, respectively, those and other peptides are quantified in FIG. 4E. In this model, peptides 11, 15, 16, and 21 produced the greatest permeation into the spheroids. See Materials and Methods #6 for more details.

Example 5. In Vivo BBB Permeation Screening

Figure 5A:
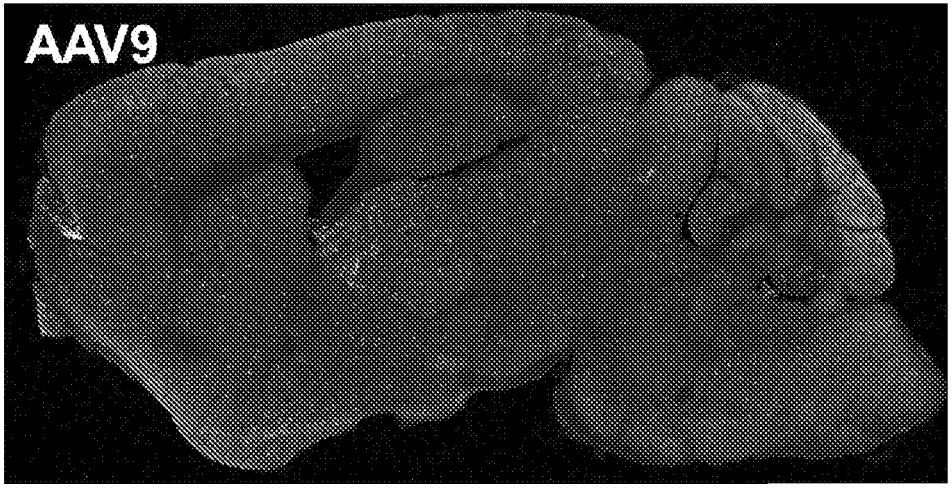
FIGS. 5A-5B depict representative images of brain sections and their quantitative analysis after intravenous administration of AAV9, AAV.CPP.16 and AAV.CPP.21 in C57BL/6J inbred mice. All candidate AAVs express nuclear red fluorescent protein (RFP) as reporter. The dose of AAV is $1\times10^{12}$ vg per animal. Each white dot in FIG. 5A represents a RFP-labeled cell.
Figure 5A:
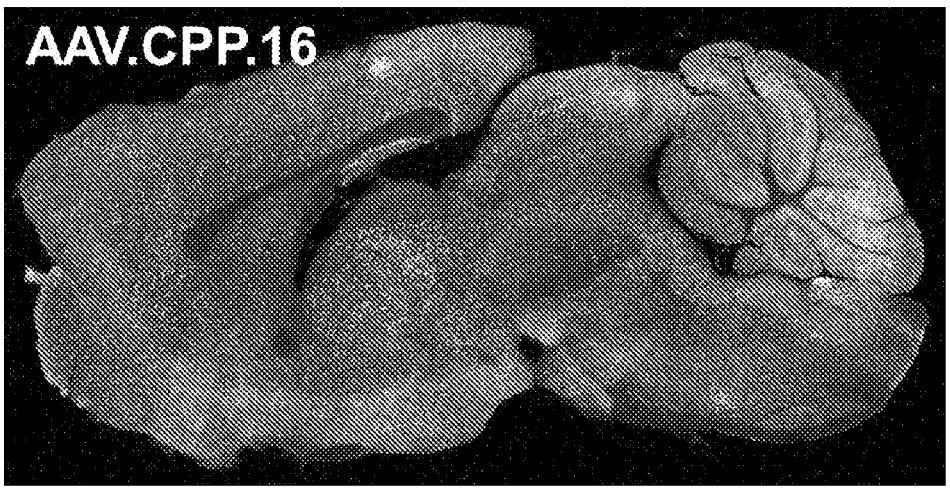
Figure 5A:
Figure 5B:
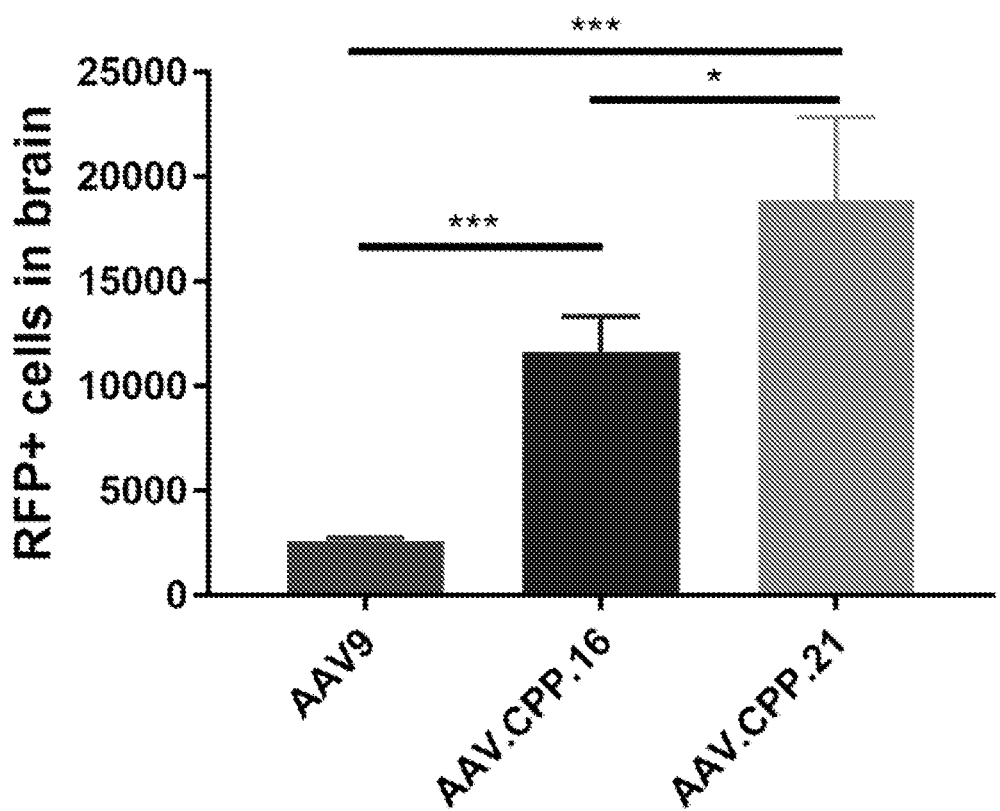
Figure 6A:
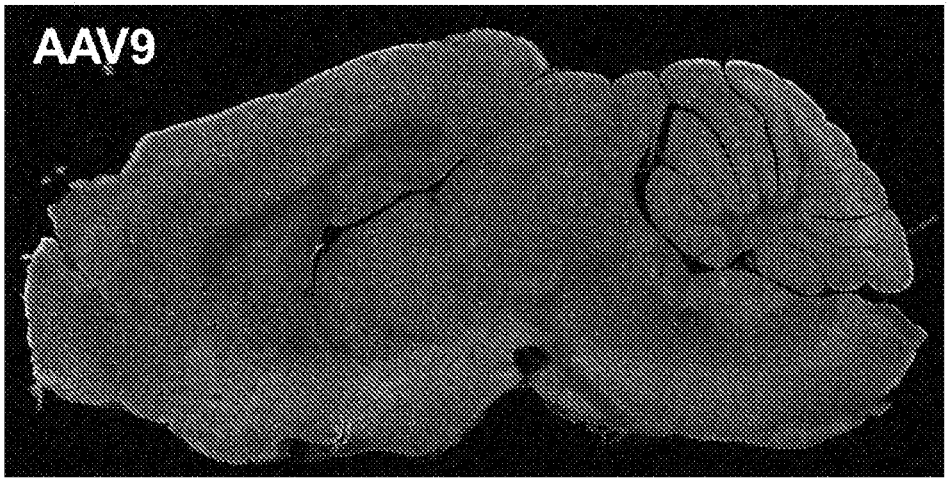
FIGS. 6A-6B depict representative images of brain sections and their quantitative analysis after intravenous administration of AAV9, AAV.CPP.16 and AAV.CPP.21 in BALB/cJ inbred mice. All candidate AAVs express nuclear red fluorescent protein (RFP) as reporter. The dose of AAV is $1\times10^{12}$ vg per animal. Each white dot in FIG. 6A represents a RFP-labeled cell.
Figure 6A:
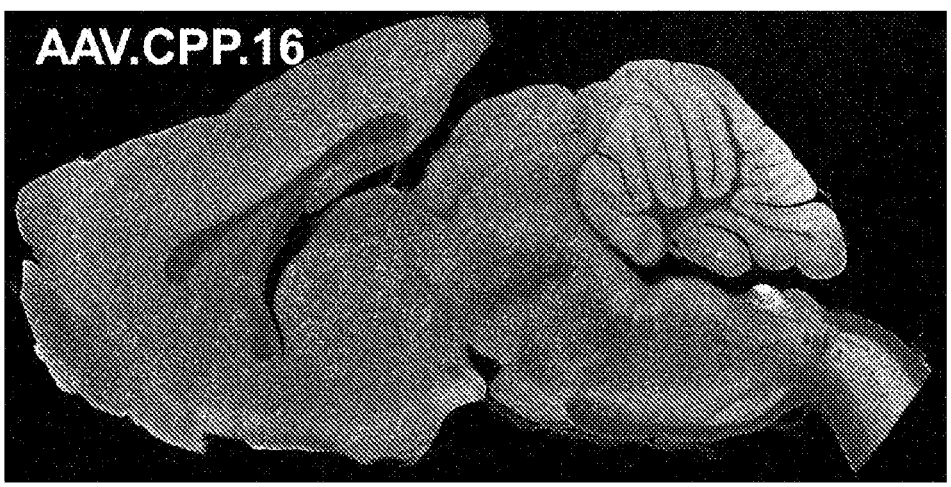
Figure 6A:
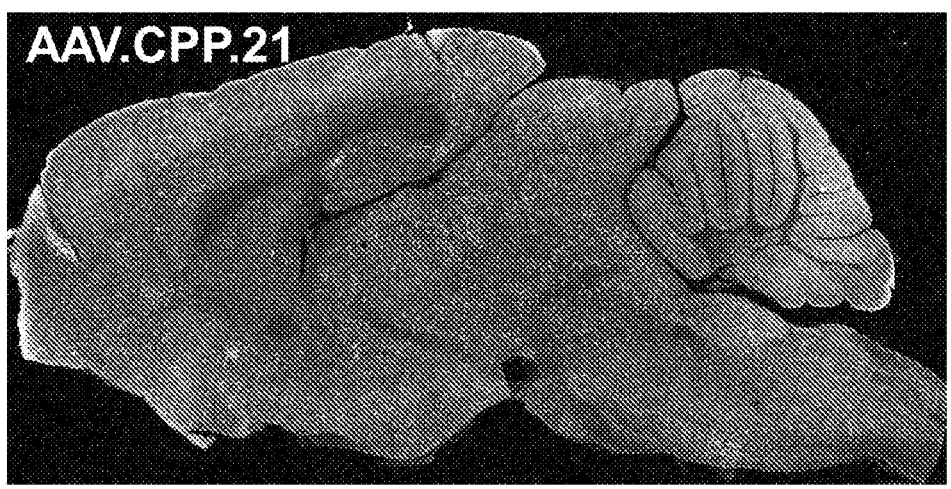
Figure 6B:
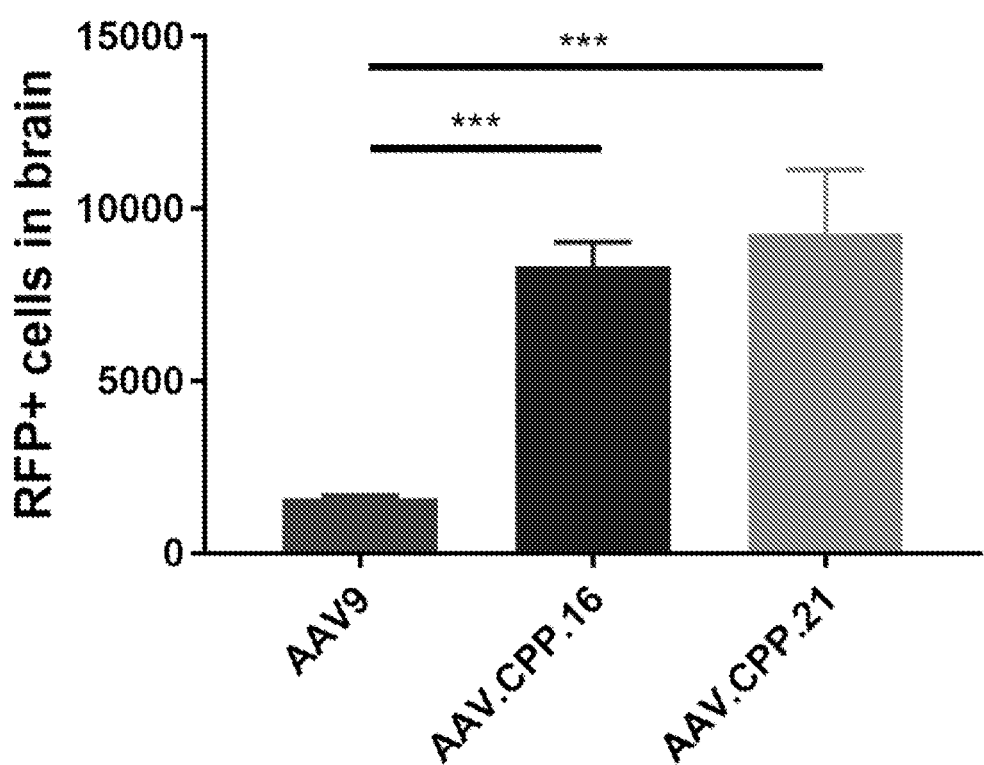

AAV.CPP.16 and AAV.CPP.21 were selected for further evaluation in an in vivo model, in experiments performed as described above for Example 2. All AAVs carried nuclear RFP as reporter. Both showed enhanced ability vs. AAV9 to transduce brain cells after intravenous administration in C57BL/6J adult mice (white dots in brain sections in FIG. 5A, quantified in FIG. 5B) and in BALB/c adult mice (white dots in brain sections in FIG. 6A, quantified in FIG. 6B).

Figure 7A:
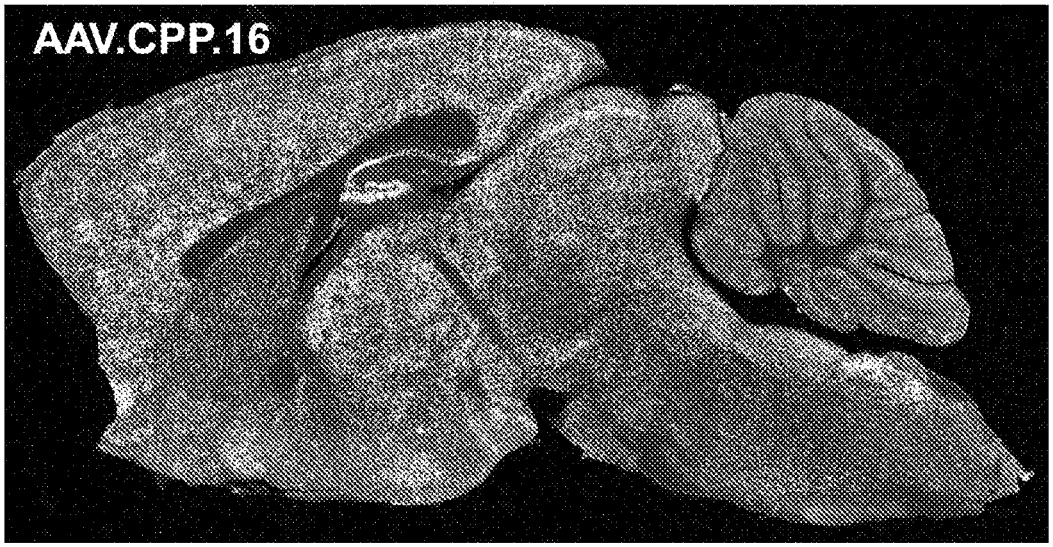
FIGS. 7A-7B depict representative images of brain sections and their quantitative analysis after intravenous administration of high-dose AAV.CPP.16 and AAV.CPP.21 in C57BL/6J inbred mice. Both candidate AAVs express nuclear red fluorescent protein (RFP) as reporter. The dose of AAV is $4\times10^{12}$ vg per animal. Each white dot in FIG. 7A represents a RFP-labeled cell.
Figure 7A:
Figure 7B:
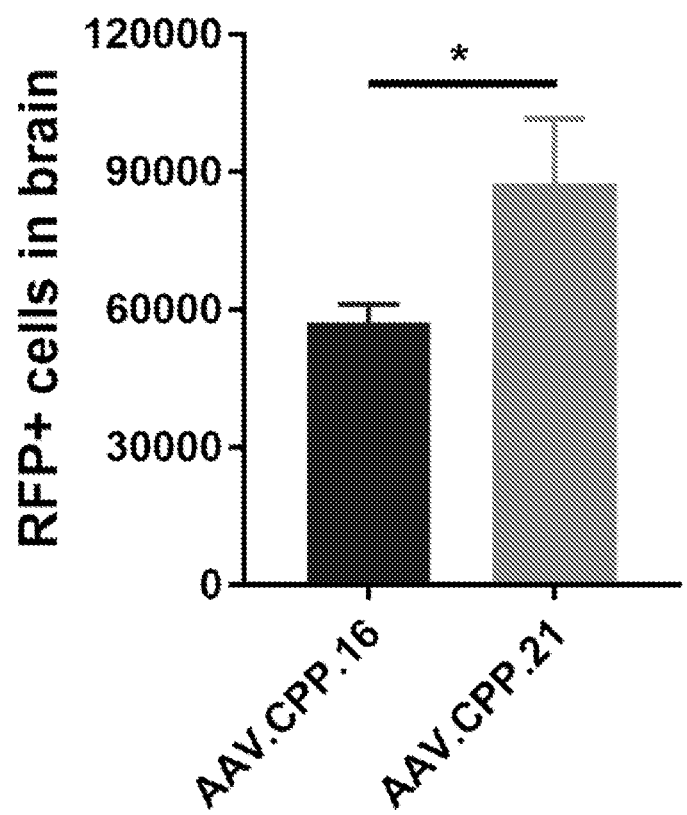

High doses of AAV.CPP.16 and AAV.CPP.21 ($4 \times 10^{12}$ vg per mouse, administered IV) resulted in widespread brain transduction in mice. Both AAVs carried nuclear RFP as reporter (white dots in brain sections in FIG. 7A, quantified in FIG. 7B).

Example 6. In Vivo Distribution of Modified AAVs

Figure 8A:
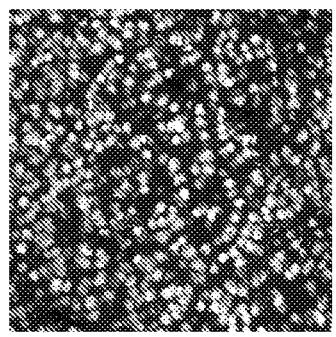
FIG. 8A shows AAV.CPP.16 and AAV.CPP.21 transduce adult neurons (labeled by a NeuN antibody) across multiple brain regions in mice including the cortex, midbrain and hippocampus. Transduced neurons are co-labeled by NeuN antibody and RFP. AAVs of $4\times10^{12}$ vg were administered intravenously in adult C57BL/6J mice (6 weeks old).
Figure 8A:
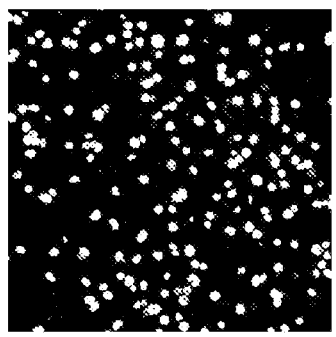
Figure 8A:
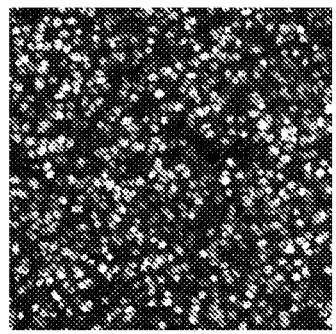
Figure 8A:
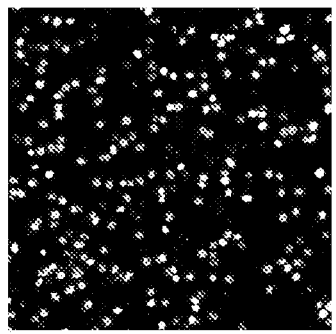
Figure 8A:
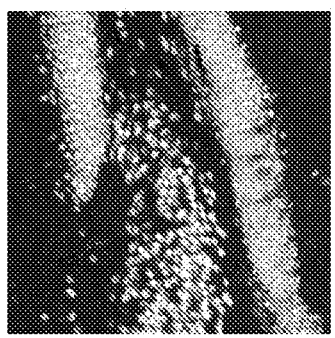
Figure 8A:
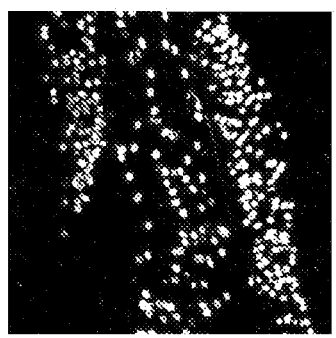

As shown in FIG. 8A, AAV.CPP.16 and AAV.CPP.21 preferentially targeted neurons (labeled by a NeuN antibody) across multiple brain regions in mice including the cortex, midbrain and hippocampus. Both AAVs carried nuclear RFP as a reporter.

Figure 8B:
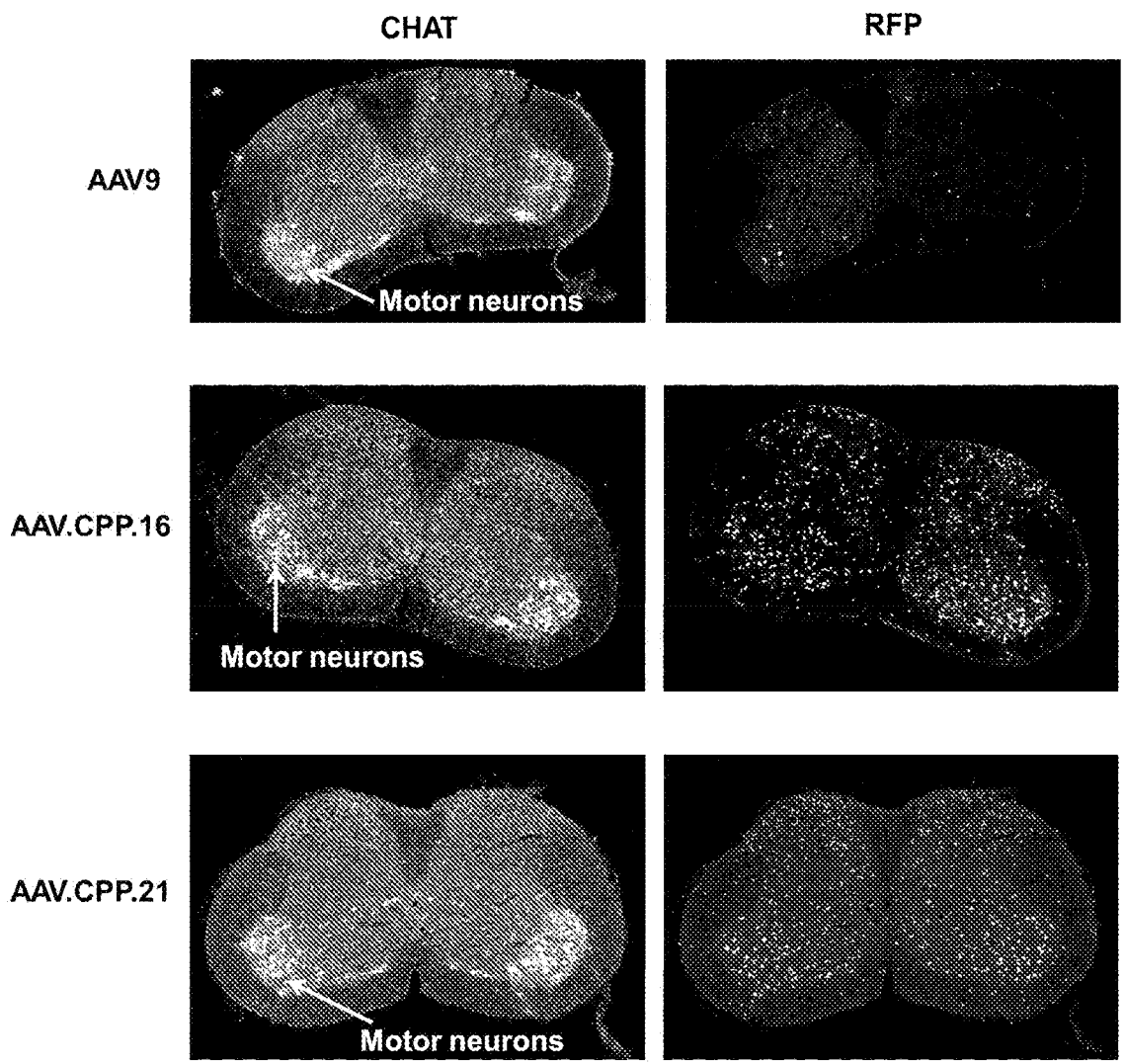
FIG. 8B depicts that AAV.CPP.16 and AAV.CPP.21 show enhanced ability vs. AAV9 in targeting the spinal cord and motor neurons in mice. AAVs of $4\times10^{10}$ vg were administered intravenously into neonate mice (1 day after birth). Motor neurons in the ventral horn of the spinal cord were visualized using CHAT antibody staining. Co-localization of RFP and CHAT signals suggests specific transduction of the motor neurons.

AAV.CPP.16 and AAV.CPP.21 also showed enhanced ability vs. AAV9 in targeting the spinal cord and motor neurons in mice. All AAVs carry nuclear RFP as reporter and were administered intravenously into neonate mice ($4 \times 10^{10}$ vg). Motor neurons were visualized using CHAT antibody staining. Co-localization of RFP and CHAT signals in FIG. 8B suggested specific transduction of the motor neurons.

The relative abilities of AAV-CAG-H2B-RFP and AAV.CPP.16-CAG-H2B-RFP to transduce various tissues in mice was also evaluated. $1 \times 10^{11}$ vg was injected intravenously. The number of cells transduced was normalized to the number of total cells labeled by DAPI nuclear staining. The results showed that AAV.CPP.16 was more efficient than AAV9 in targeting heart (FIG. 9A); skeletal muscle (FIG. 9B), and dorsal root ganglion (FIG. 9C) tissue in mice.

Example 7. BBB Permeation in a Non-Human Primate Model

2×10$^{13}$ vg/kg AAVs-CAG-AADC (as reporter gene) were injected intravenously into 3-month-old cynomolgus monkeys. AAV-transduced cells (shown in black) were visualized using antibody staining against AADC. As shown in FIGS. 10A-D, AAV.CPP.16 and AAV.CPP.21 showed enhanced ability vs. AAV9 to transduce brain cells after intravenous administration in non-human primates. AAV.CPP.16 transduced significantly more cells then wt AAV9 in the primary visual cortex (FIG. 10A), parietal cortex (FIG. 10B), thalamus (FIG. 10C), and cerebellum (FIG. 10D). See Materials and Methods #7-8 for more details.

Example 8. AAV.CPP.16 and AAV.CPP.21 do not Bind to LY6A

LY6A serves as a receptor for AAV.PHP.eB and mediates AAV.PHP.eB's robust effect in crossing the BBB in certain mouse strains. Over-expressing mouse LY6A in cultured 293 cells significantly increased binding of AAV.PIP.eB to the cell surface (see FIG. 11A). On the contrary, over-expressing LY6A does not increase viral binding for AAV9, AAV.CPP.16 or AAV.CPP.21 (see FIG. 11B). This suggests AAV.CPP.16 or AAV.CPP.21 does not share LY6A with AAV.PHP.eB as a receptor. See Materials and Methods #9 for more details.

Example 9. Delivering Therapeutic Proteins to the Brain Using AAV.CPP.21

AAV.CPP.21 was used to systemically deliver the "suicide gene" HSV.TK1 in a mouse model of brain tumor. HSV.TK1 turns the otherwise "dormant" ganciclovir into a tumor-killing drug. Intravenously administered AAV.CPP.21-H2BmCherry (FIG. 12A, bottom left and middle right panel) was shown to target tumor mass, especially the tumor expanding frontier. As shown in FIGS. 12B-C, using AAV.CPP.21 to systemically deliver the "suicide gene" HSV.TK1 resulted in shrinkage of brain tumor mass, when combined with the pro-drug ganciclovir. These results show that AAV.CPP.21 can be used to systemically deliver a therapeutic gene into brain tumor. See Materials and Methods #10 for more details.

Example 10. Intracerebral Administration of AAV.CPP.21

In addition to systemic administration (such as in Example 2), an AAV as described herein was administered locally into the mouse brain. Intracerebral injection of AAV9-H2B-RFP and AAV.CPP.21-H2B-RFP (FIG. 13) resulted in more widespread and higher-intensity RFP signal in AAV.CPP.21-treated brain sections vs. AAV9-treated ones. See Materials and Methods #4 for more details.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An AAV capsid protein comprising a targeting sequence that comprises TVSALFK (SEQ ID NO:8); TVSALK (SEQ ID NO:4); KLASVT (SEQ ID NO:83); or KFLASVT (SEQ ID NO:84), wherein the targeting sequence is inserted in a position corresponding to amino acids 588 and 589 of SEQ ID NO:85.

2. The AAV capsid protein of claim 1, comprising an amino acid sequence that comprises TVSALK (SEQ ID NO:4).

3. The AAV capsid protein of claim 1, comprising an amino acid sequence that comprises TVSALFK (SEQ ID NO:8).

4. The AAV capsid protein of claim 1, wherein the AAV is AAV9.

5. The AAV capsid protein of claim 1, comprising AAV9 VP1.

6. An AAV comprising the capsid protein of claim 1.

7. The AAV of claim 6, further comprising a transgene.

8. The AAV capsid protein of claim 1, comprising an amino acid sequence of SEQ ID NO: 89 or SEQ ID NO: 90.

9. The AAV of claim 7, wherein the transgene is a therapeutic transgene.

10. The AAV of claim 7, wherein the transgene comprises a non-coding RNA.

11. The AAV of claim 7, wherein the transgene encodes an anti-cancer agent.

* * * * *